US007553798B2

(12) United States Patent
Lamberth et al.

(10) Patent No.: US 7,553,798 B2
(45) Date of Patent: Jun. 30, 2009

(54) HETEROCYCLIC CARBOXAMIDES WITH MICROBIOCIDAL ACTIVITY

(75) Inventors: Clemens Lamberth, Basel (CH); Camilla Corsi, Basel (CH); Josef Ehrenfreund, Basel (CH); Hans Tobler, Basel (CH); Harald Walter, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 11/570,796

(22) PCT Filed: Jun. 21, 2005

(86) PCT No.: PCT/EP2005/006688

§ 371 (c)(1), (2), (4) Date: Dec. 18, 2006

(87) PCT Pub. No.: WO2005/123722

PCT Pub. Date: Dec. 29, 2005

(65) Prior Publication Data

US 2008/0132557 A1 Jun. 5, 2008

(30) Foreign Application Priority Data

Jun. 22, 2004 (GB) ................................ 0413970.5

(51) Int. Cl.

| | |
|---|---|
| ***A01N 43/40*** | (2006.01) |
| ***A01N 43/78*** | (2006.01) |
| ***A01N 43/56*** | (2006.01) |
| ***A01N 43/36*** | (2006.01) |
| ***C07D 213/44*** | (2006.01) |
| ***C07D 417/02*** | (2006.01) |
| ***C07D 401/02*** | (2006.01) |
| ***C07D 409/02*** | (2006.01) |
| ***C07D 277/20*** | (2006.01) |
| ***C07D 403/02*** | (2006.01) |
| ***C07D 231/10*** | (2006.01) |

(52) U.S. Cl. ...................... 504/250; 504/251; 504/252; 504/253; 504/266; 504/280; 504/287; 546/262; 546/269.7; 546/275.4; 546/280.4; 548/200; 548/365.1; 548/365.7; 548/364.1; 548/527

(58) Field of Classification Search ................. 514/406; 548/365.7, 365.1, 200, 364.1, 527; 546/262, 546/269.7, 275.4, 280.4; 504/250, 251, 252, 504/253, 266, 280, 287
See application file for complete search history.

(56) References Cited

U.S. PATENT DOCUMENTS

| | | | |
|---|---|---|---|
| 4,567,197 A | 1/1986 | Brewster et al. | |
| 6,001,829 A | 12/1999 | Kramer et al. | |
| 6,255,333 B1 | 7/2001 | Banks | |
| 6,699,818 B1 * | 3/2004 | Walter et al. | 504/287 |

FOREIGN PATENT DOCUMENTS

| | | |
|---|---|---|
| DD | 0283916 | 10/1990 |
| EP | 0234119 | 9/1987 |
| EP | 0350237 | 1/1990 |
| EP | 0609459 | 8/1994 |
| EP | 0776894 | 6/1997 |
| EP | 0846686 | 6/1998 |
| WO | 199804530 | 2/1998 |
| WO | 200140195 | 6/2001 |
| WO | 2001532529 | 7/2001 |
| WO | WO 01/53259 A1 * | 7/2001 |
| WO | 2004018438 | 3/2004 |
| WO | WO 2004/058723 A1 * | 7/2004 |
| WO | WO 2004/099195 A1 * | 11/2004 |
| WO | 2005028485 | 3/2005 |

OTHER PUBLICATIONS

Patent Abstracts of Japan, vol. 2002, No. 02, Apr. 2, 2002; & JP 2001 302605 A (Sumitomo Chem Co. LTD), Oct. 31, 2001, cited in the application, '00121-'00151, abstract.

Database CA 'Online!; Chemical Abstracts Service, Columbus, Ohio, US; Rebstock, Anne-Sophie et al: "Synthesis and deprotonation of 2-(pyridyl)phenols and 2-(pyridyl)anilines"; XP002347738, retrieved fron STN Database accession No. 2003:669328, RN: 634591-08-05, abstract & Organic & Biomolecular Chemistry 1 (17), 3064-3068 Coden: OBCRAK; ISSN: 1477-0520, 2003.

Databasse CA 'Online! Chemical Abstracts Service, Columbus, Ohio, US; Arzel, Erwan et al: "A new synthesis of .alpha.-substituted .delta.-carbolines"; XP002347739, retrieved from STN Database accession No. 1997: 644490, RN; 19177-66-5, abstract, & Journal of Heterocyclic Chemistry, 34(4), 1205-1210 Coden: JHTCAD; ISSN: 0022-152X, 1997.

Database CA 'Online! Chemical Abstracts Service, Columbus, Ohio, US; Rocca, P. et al: "A new covergent synthesis of substituted.beta.-carbolines"; XP002347740, retrieved from STN Database accession No. 1993:472900; RN: 148639-21-8, abstract & Tetrahedron, 49(16), 3325-42 Coden: Tetrab; ISSN: 0040-4020, 1993.

(Continued)

*Primary Examiner*—Kamal A Saeed
*Assistant Examiner*—Kristin Bianchi
(74) *Attorney, Agent, or Firm*—Thomas Hamilton

(57) ABSTRACT

Compounds of the formula (I), in which the substituents are as defined in claim 1 are suitable for use as microbiocides.

(I)

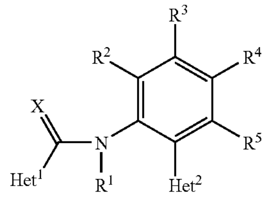

2 Claims, No Drawings

OTHER PUBLICATIONS

Pasquinet, Eric et al: “First Total Synthesis of Phenylpyridine Analogues of the Antimitolic Rhazinilam”, Journal of Organic Chemistry, 66(8), 2654-2661 Coden; Joceah; ISSN; 0022-3263, 2001, XP002345239, compounds 13A, 13B.
Arzel E et al: “A new synthesis of .alpha.-substituted.delta.-carbolines”, Journal of Heterocyclic Chemisty, Heterocroporation, Provo, US, vol. 34, No. 4, 1997, pp. 1205-1210, XP002311557, ISSN: 0022-152X, table I; compound 4I.
Database CA 'Online! Chemical Abstracts Service, Columbus, Ohio, US; Alazard, Jean-Pierre et al: “Compounds interacting with tubulin. Part II, Synthesis of tricyclic lactams with a phenylpyrrole framework, structural analogs of rhazinilam”; XP002347741, retrieved from STN, Database accession No. 1996:421015, RN:139984-62-6, abstract & Bulletin De La Societe Chimique De France, 133(3), 251-266 Coden; BSCFAS, ISSN: 0037-8968, 1996.
Frank, Kristine E. et al: “Cyclizations of Substituted Benzylidene-3-alkenylamines: Synthesis of the Tricyclic Core of the Martinellines”; Journal of Organic Chemistry, 65(3), 655-666 Coden: Joceah; ISSN: 0022-3263, 2000, XP002345240 compounds, 47, 48.
Qazi, Naveed A. et al: “Domino addition of allylzince bromide to nitrile oxides; Synthesis of 5-butenylisoxazolines,” Tetrahedron Letters, 46(25), 4391-4393 Coden: Teleay; ISSN: 0040-4039, May 20, 2005, XP002345241, table 1; compound 4F.
Database CA "Online! Chemical Abstracts Service, Columbus, Ohio, US; Dolman, Sarah J. et al: “Efficient Catalytic Enantioselective Synthesis of Unsaturated Amines: Preparation of Small-and Medium-Ring Cyclic Amines through Mo-Catalyzed Asymmetric Ring-Closing Metathesis in the Absence of Solvent”; XP002347742, retrieved from STN, Database Accession No. 2002:378094; RN: 44375-85-6, abstract, & Journal of the American Chemical Society, 124(24), 6991-6997 Coden: JACSAT; ISSN: 0002-7863, 2002.
Database CA 'Online!; Chemical Abstracts Service, Columbus, Ohio, US; Li, Laisheng et al: “Synthesis of pyrazoles from 1,1,5-trichloropent-1-2n-3-one. I” XP002347743, retrieved from STN Database Accession No. 1997:692843, RN: 198194-98-8, abstract, & Huaxue Shiji, 19(4), 196-199, Coden: HUSHDR; ISSN: 0258-3283, 1997.
Database CA 'Online!; Chemical Abstracts Service, Columbus, Ohio, US; Balsamo, A. et al: “Conformationally restrained .beta.-blocking oxime ethers. 2. Synthesis and .beta.-adrenergic properties of diastereoisomeric anti and syn2-(5'-(3'-aryl-substituted)isoxzolidinyl)-N-alkylethanolamines”, XP002347744, retrieves from STN Database accession No. 1995:319158, RN: 161064-08-0, abstracts, & European Journal of Medicinal Chemistry, 29(11), 855-67, Coden: EJMCA5; ISSN; 0023-5234, 1994.
Database CA "Online! Chemical Abstracts Service, Columbus, Ohio, US; Kim, Jae Nyoung et al: “Regioselectivity and stereoselectivity in nitrile oxide cycloaddition to 1,5-hexadien-3-ol. The study on the hydrogen bonding effect and magnesium chelation effect in nitrile oxide cycloaddition” XP002347745 retrieved from STN Database accession No. 1994:76710 & Synthetic Communications , 23(12), 1673-82 Coden: SYNCAV; ISSN: 0039-7911, 1993.
Database CA "Online! Chemical Abstracts Service, Columbus, Ohio, US; Ebens, Rijko et al: “1-Aryl-2,2-dimethyl-1,3-propanediols as chiral auxiliaries. Acetal formation with .alpha.,.beta.-unsaturated aldehydes and analysis of the stereochemistry of cyclopropanation” XP002347746 retrieved from STN Database accession No. 1991:184829 & Recueil Des Travaux Chimiques Des Pays-Bas ,109(11), 552-60 Coden: RTCPA3; ISSN: 0165-0513, 1990.
Database CA "Online! Chemical Abstracts Service, Columbus, Ohio, US; Kvita, Vratislav: “A new synthesis of 5-vinylpyrimidines” XP002347747 retieved from STN Database accession No. 1987:213887 & Synthesis , (9), 786-8 Coden: SYNTBF; ISSN: 0039-7881, 1986.
Database CA "Online! Chemical Abstracts Service, Columbus, Ohio, US; Tulyaganov, S. R. et al: “Synthesis of some aromatic aminoalcohols and their oxazolidine derivatives” XP002347748 retrieved from STN Database accession No. 1967:10870 & Uzbekskii Khimicheskii Zhurnal , 10(4), 32-5 Coden: UZKZAC, 1966.
Database CA "Online! Chemical Abstracts Service, Columbus, Ohio, US; Brueckner, Sebastien et al: “Cascade Cyclization: An Easy Access to Highly Unsaturated Polycyclic Ring Systems through a Tandem Stille/'4+2! Reaction under Mild Conditions” XP002347749 retrieved from STN Database accession No. 2002:675498 & Organic Letters , 4(20), 3391-3393 Coden: ORLEF7; ISSN: 1523-7060, 2002.
Database Beilstein; Beilstein Crossfire Institut Zur Foerderung Der Chemischen Wissenschaften, DE; BRN 9203038 2003, XP002347750, abstract.
Database Beilstein; Beilstein Crossfire Institut Zur Foerderung Der Chemischen Wissenschaften, DE; BRN 6371788 1994, XP002347751, abstract.
Database Beilstein; Beilstein Crossfire Institut Zur Foerderung Der Chemischen Wissenschaften, DE; BRN 6870548 1994, XP002347752, abstract.
Database Beilstein; Beilstein Crossfire Institut Zur Foerderung Der Chemischen Wissenschaften, DE; BRN 7129334 1995, XP002347753, abstract.
Database Beilstein; Beilstein Crossfire Institut Zur Foerderung Der Chemischen Wissenschaften, DE; BRN 6335945 1994, XP002347754, abstract.
Database Beilstein; Beilstein Crossfire Institut Zur Foerderung Der Chemischen Wissenschaften, DE; BRN 4257117 1992, XP002347755, abstract.
Database Beilstein; Beilstein Crossfire Institut Zur Foerderung Der Chemischen Wissenschaften, DE; BRN 4401758 1994, XP002347756, abstract.
Database Beilstein; Beilstein Crossfire Institut Zur Foerderung Der Chemischen Wissenschaften, DE; BRN 987732 1988, XP002347757, abstract.
Database Beilstein; Beilstein Crossfire Institut Zur Foerderung Der Chemischen Wissenschaften, DE; BRN 552656 1988, XP002347758, abstract.
Database Beilstein; Beilstein Crossfire Institut Zur Foerderung Der Chemischen Wissenschaften, DE; BRN 4003570 1991, XP002347759, abstract.

* cited by examiner

HETEROCYCLIC CARBOXAMIDES WITH MICROBIOCIDAL ACTIVITY

The present invention relates to novel carboxamide derivatives as active ingredients which have microbiocidal activity, in particular fungicidal activity. The invention also relates to preparation of these active ingredients, to novel heterocyclic derivatives used as intermediates in the preparation of these active ingredients, to preparation of these novel intermediates, to agrochemical compositions which comprise at least one of the novel active ingredients, to preparation of these compositions and to use of the active ingredients or compositions in agriculture or horticulture for controlling or preventing infestation of plants by phytopathogenic microorganisms, preferably fungi.

Fungicidally active carboxamide derivatives are disclosed for example in JP2001302605.

The present invention provides a compound of formula (I):

(I)

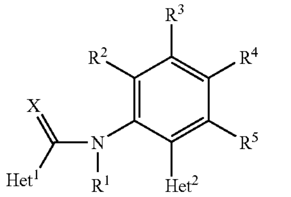

where $Het^1$ and $Het^2$ are each, independently, a 5- or 6-membered heterocyclic ring containing one to three heteroatoms, each independently selected from oxygen, nitrogen and sulphur; $Het^1$ being substituted by one, two or three groups $R^{y1}$ and $Het^2$ being substituted by $R^6$ and being optionally substituted by one, two or three groups $R^{y2}$; $R^1$ is hydrogen, formyl, CO—$C_{1-4}$ alkyl, COO—$C_{1-4}$ alkyl, $C_{1-4}$ alkoxy($C_{1-4}$)alkylene, CO—$C_{1-4}$ alkylenoxy($C_{1-4}$)alkyl, propargyl or allenyl; $R^2$, $R^3$, $R^4$ and $R^5$ are each, independently, hydrogen, halogen, methyl or $CF_3$; $R^6$ is $(Z)_mC{\equiv}C(Y^1)$, $(Z)_mC(Y^1){=}C(Y^2)(Y^3)$ or tri($C_{1-4}$)alkylsilyl; each $R^{y1}$ or each $R^{y2}$ is, independently, halogen, $C_{1-3}$ alkyl, $C_{1-3}$ haloalkyl, $C_{1-3}$ alkoxy($C_{1-3}$) alkylene or cyano; X is O or S; $Y^1$, $Y^2$ and $Y^3$ are each, independently, hydrogen, halogen, $C_{1-6}$ alkyl [optionally substituted by one or more substituents each independently selected from halogen, hydroxy, $C_{1-4}$ alkoxy, $C_{1-4}$ haloalkoxy, $C_{1-4}$ alkylthio, $C_{1-4}$ haloalkylthio, $C_{1-4}$ alkylamino, di($C_{1-4}$) alkylamino, $C_{1-4}$ alkoxycarbonyl, $C_{1-4}$ alkylcarbonyloxy and tri($C_{1-4}$)alkylsilyl], $C_{2-4}$ alkenyl [optionally substituted by one or more substituents each independently selected from halogen], $C_{2-4}$ alkynyl [optionally substituted by one or more substituents each independently selected from halogen], $C_{3-7}$ cycloalkyl [optionally substituted by one or more substituents each independently selected from halogen, $C_{1-4}$ alkyl and $C_{1-4}$ haloalkyl] or tri($C_{1-4}$)alkylsilyl; Z is $C_{1-4}$ alkylene [optionally substituted by one or more substituents each independently selected from hydroxy, cyano, $C_{1-4}$ alkoxy, halogen, $C_{1-4}$ haloalkyl, $C_{1-4}$ haloalkoxy, $C_{1-4}$ alkylthio, COOH and COO—$C_{1-4}$ alkyl]; and m is 0 or 1.

In one particular aspect, the present invention provides a compound of formula (I) as defined above where $R^6$ is $(Z)_mC{\equiv}C(Y^1)$ or $(Z)_mC(Y^1){=}C(Y^2)(Y^3)$; and $Y^1$, $Y^2$ and $Y^3$ are each, independently, hydrogen, halogen, $C_{1-4}$ alkyl [optionally substituted by one or more substituents each independently selected from halogen, hydroxy, $C_{1-4}$ alkoxy, $C_{1-4}$ haloalkoxy, $C_{1-4}$ alkylthio, $C_{1-4}$ haloalkylthio, $C_{1-4}$ alkylamino, di($C_{1-4}$)alkylamino, $C_{1-4}$ alkoxycarbonyl and tri($C_{1-4}$)alkylsilyl], $C_{2-4}$ alkenyl [optionally substituted by one or more substituents each independently selected from halogen], $C_{2-4}$ alkynyl [optionally substituted by one or more substituents each independently selected from halogen], $C_{3-7}$ cycloalkyl [optionally substituted by one or more substituents each independently selected from halogen, $C_{1-4}$ alkyl and $C_{1-4}$ haloalkyl] or tri($C_{1-4}$)alkylsilyl.

In one aspect, the present invention provides a compound of formula (I) as defined above where $R^6$ is $(Z)_mC{\equiv}C(Y^1)$ or $(Z)_mC(Y^1){=}C(Y^2)(Y^3)$; and Z is $C_{1-4}$ alkylene [optionally substituted by one or more substituents each independently selected from hydroxy, cyano, $C_{1-4}$ alkoxy, $C_{1-4}$ haloalkoxy, $C_{1-4}$ alkylthio, COOH and COO—$C_{1-4}$ alkyl].

Halogen is fluorine, chlorine, bromine or iodine [preferably fluorine, chlorine or bromine].

Each alkyl moiety is a straight or branched chain and is, for example, methyl, ethyl, n-propyl, n-butyl, iso-propyl, n-butyl, sec-butyl, iso-butyl or tert-butyl. Likewise, each alkylene moiety is a straight or branched chain.

Haloalkyl moieties are alkyl moieties which are substituted by one or more of the same or different halogen atoms and are, for example, $CF_3$, $CF_2Cl$, $CHF_2$, $CH_2F$, $CCl_3$, $CF_3CH_2$, $CHF_2CH_2$, $CH_2FCH_2$, $CH_3CHF$ or $CH_3CF_2$.

Alkenyl and alkynyl moieties can be in the form of straight or branched chains. The alkenyl moieties, where appropriate, can be of either the (E)- or (Z)-configuration. Examples are vinyl, allyl, ethynyl and propargyl.

Cycloalkyl includes cyclopropyl, cyclobutyl, cyclopentyl, cyclohexyl and cycloheptyl.

In tri($C_{1-4}$)alkylsilyl and in di($C_{1-4}$)alkylamino, each alkyl moiety is selected independently.

Throughout this description, Me stands for methyl and Et stands for ethyl.

It is preferred that $Het^1$ is pyrazole, pyrrole, thiophene, furane, thiazole, isothiazole, oxazole, isoxazole, pyridine, pyrazine, pyrimidine, pyridazine, 5,6-dihydropyran or 5,6-dihydro-1,4-oxathiine [more preferably pyrazole, pyrrole, thiophene, furane, thiazole, oxazole, pyridine, pyrimidine, pyridazine or 5,6-dihydropyran; yet more preferably pyrazole, pyrrole, thiophene, thiazole or pyridine; and even more preferably pyrazole, pyrrole thiazole or pyridine].

It is preferred that $Het^2$ is pyrazole, pyrrole, thiophene, furane, thiazole, isothiazole, oxazole, isoxazole, pyridine, pyrazine, pyrimidine, pyridazine, triazine, oxadiazole, thiadiazole or imidazole. Within this embodiment it is even more preferred that $Het^2$ is pyrazole, pyrrole or thiophene. In another preferred aspect of this embodiment it is preferred that $Het^2$ is pyrazole, thiophene or furane.

Preferably $R^1$ is hydrogen, propargyl, allenyl, formyl, COMe, COEt or $COCH_2OMe$.

More preferably $R^1$ is hydrogen, propargyl, allenyl or COMe.

Even more preferably $R^1$ is hydrogen.

Preferably $R^2$ is hydrogen.

Preferably $R^3$ is hydrogen.

Preferably $R^4$ is hydrogen.

Preferably $R^5$ is hydrogen or halogen.

More preferably $R^5$ is hydrogen or fluorine.

Even more preferably $R^5$ is hydrogen.

In a preferred embodiment of the invention $R^6$ is $(Z)_mC{\equiv}C(Y^1)$ or $(Z)_mC(Y^1){=}C(Y^2)(Y^3)$.

In another preferred embodiment of the invention $R^6$ is $(Z)_mC{\equiv}C(Y^1)$.

In yet another preferred embodiment of the invention $R^6$ is $(Z)_mC(Y^1){=}C(Y^2)(Y^3)$.

In yet another preferred embodiment of the invention $R^6$ is tri($C_{1-4}$)alkylsilyl;

Preferably $Y^1$, $Y^2$ and $Y^3$ are, independently, hydrogen, halogen, $C_{1-6}$ alkyl, $C_{1-3}$ haloalkyl, $C_{1-4}$(haloalkoxy)$C_{1-4}$ alkyl, $C_{1-4}$(haloalkylthio)$C_{1-4}$ alkyl, trimethylsilyl, $C_{2-4}$ alkenyl, $C_{2-4}$ haloalkenyl or $C_{3-6}$ cycloalkyl (optionally substituted by one or more substituents each independently selected from halogen and $C_{1-2}$ alkyl).

Preferably Z is $C_{1-2}$ alkylene [which may be optionally substituted by one or more substituents each independently selected from halogen, $C_{1-4}$ haloalkyl and $C_{1-4}$ haloalkoxy].

Preferably $R^6$ is vinyl [optionally substituted by one to three substituents each independently selected from halogen, $C_{1-4}$ alkyl, $C_{1-3}$ haloalkyl, $C_{3-6}$ cycloalkyl (optionally substituted by one to five substituents each independently selected from halogen, $CH_3$ and $C_{1-2}$ haloalkyl) and trimethylsilyl], ethynyl [optionally substituted by one substituent selected from cyclopropyl, cyclopentyl and cyclohexyl (each optionally substituted by one to five substituents each independently selected from halogen, $CH_3$ and $C_{1-2}$ haloalkyl), halogen, $C_{1-6}$ alkyl, $C_{1-4}$haloalkyl, $C_{2-4}$ alkenyl, $C_{2-4}$ haloalkenyl and tri($C_{1-4}$)alkylsilyl], allyl [optionally substituted by one to three substituents each independently selected from halogen, $CH_3$, $C_{1-2}$ haloalkyl and trimethylsilyl], propargyl [optionally substituted by one to three substituents each independently selected from halogen, $C_{1-4}$ alkyl, $C_{1-2}$ haloalkyl and trimethylsilyl] or tri($C_{1-4}$)alkylsilyl.

Also preferably $R^6$ is vinyl [optionally substituted by one to three substituents each independently selected from halogen, $C_{1-4}$ alkyl, $C_{1-3}$ haloalkyl, $C_{3-6}$ cycloalkyl (optionally substituted by one to five substituents each independently selected from halogen, $CH_3$ and $C_{1-2}$ haloalkyl) and trimethylsilyl], ethynyl [optionally substituted by one substituent selected from cyclopropyl, cyclopentyl and cyclohexyl (each optionally substituted by one to five substituents each independently selected from halogen, $CH_3$ and $C_{1-2}$ haloalkyl), halogen, $C_{1-6}$ alkyl, $C_{1-4}$haloalkyl, $C_{2-4}$ alkenyl, $C_{2-4}$ haloalkenyl and tri($C_{1-4}$)alkylsilyl], allyl [optionally substituted by one to three substituents each independently selected from halogen, $CH_3$, $C_{1-2}$ haloalkyl and trimethylsilyl] or propargyl [optionally substituted by one to three substituents each independently selected from halogen, $C_{1-4}$ alkyl, $C_{1-2}$ haloalkyl and trimethylsilyl].

More preferably $R^6$ is $CH{=}CH_2$, $CH{=}CH(CH_3)$, $CH{=}CHSiMe_3$, $CH{=}CF_2$, $CH{=}CCl_2$, $C(CH_3){=}CCl_2$, $CH{=}CBr_2$, $C(CH_3){=}CBr_2$, $C(CH_3){=}CF_2$, $CH{=}CFCl$, $CH{=}CFBr$, $C(CH_3){=}CFCl$, $C(CH_3){=}CFBr$, $CH{=}CFMe$, $CH{=}CBrMe$, $CH{=}CClMe$, $CH{=}CHBr$, $CH{=}CHF$, $CH{=}CHCl$, $CF{=}CF_2$, $CCl{=}CF_2$, $CCl{=}CH_2$, $CBr{=}CH_2$, $CF{=}CH_2$, $C(CF_3){=}CFBr$, $C(CF_3){=}CFCl$, $C(CF_3){=}CBr_2$, $C(CF_3){=}CCl_2$, $C(CF_3){=}CF_2$, $C(CF_3){=}CH_2$, $CF{=}CHF$, $CH{=}CHCF_3$, $CH{=}CFCF_2Cl$, $CH{=}CClCF_2Cl$, $CH{=}CBrCF_2Cl$, $CH{=}C(CF_3)_2$, $CH{=}CHC_2F_5$, $CH{=}CHCF(CF_3)_2$, $C(CH_3){=}CHCF_3$, $C(CH_3){=}CFCF_3$, $C(CH_3){=}CClCF_3$, $C(CH_3){=}CBrCF_3$, $CH{=}CClCF_3$, $CH{=}CClC_2F_5$, $CH{=}CBrCF_3$, $CH{=}CFC_2F_5$, $CH{=}CFCF_3$, $CH_2CH{=}CH_2$, $CH_2CH{=}CF_2$, $CH_2CH{=}CCl_2$, $CH_2CH{=}CBr_2$, $CH_2CH{=}CFBr$, $CH_2CH{=}CFCl$, $CH_2CH{=}CClCF_3$, $CH_2CH{=}CHSiMe_3$, $C{\equiv}CH$, $C{\equiv}CSiMe_3$, $C{\equiv}CSiEt_3$, $C{\equiv}CSiMe_2C(CH_3)_3$, $C{\equiv}CCl$, $C{\equiv}CBr$, $C{\equiv}CF$, $C{\equiv}CCF_3$, $C{\equiv}CCF_2H$, $C{\equiv}CCF_2Cl$, $C{\equiv}CCF_2Me$, $C{\equiv}CCF_2Et$, $C{\equiv}CCHFCl$, $C{\equiv}CCF_2Br$, $C{\equiv}CC_2F_5$, $C{\equiv}CCF(CF_3)_2$, $C{\equiv}CCF(CF_3)$, $C{\equiv}CCH_2F$, $C{\equiv}CCH(Me)F$, $C{\equiv}CCH(Et)F$, $C{\equiv}CMe$, $C{\equiv}CCH_2Me$, $C{\equiv}CCHMe_2$, $C{\equiv}CCH_2CHMe_2$, $C{\equiv}CCMe_3$, $C{\equiv}CCH_2CMe_3$, $C{\equiv}CCH_2SiMe_3$, $C{\equiv}CCMe_2Cl$, $C{\equiv}CCMe_2F$, $C{\equiv}CCH_2OMe$, $C{\equiv}CCH_2CF_3$, $C{\equiv}CCMe_2OMe$, $C{\equiv}CCMe_2OH$, $C{\equiv}CCMe_2OCOMe$, $C{\equiv}CC(Me){=}CH_2$, $C{\equiv}CCF{=}CF_2$, $C{\equiv}C$(cyclopropyl), $C{\equiv}C$(cyclopentyl), $C{\equiv}C$(1-F-cyclopentyl), $CH_2C{\equiv}CH$, $CF_2C{\equiv}CH$, $CHFC{\equiv}CH$, $CH(CF_3)C{\equiv}CH$, $SiMe_3$, $CH_2C{\equiv}CCMe_3$ or $CH_2C{\equiv}CSiMe_3$.

Within this embodiment of the invention $R^6$ is preferably $CH{=}CH_2$, $CH{=}CH(CH_3)$, $CH{=}CHSiMe_3$, $CH{=}CF_2$, $CH{=}CCl_2$, $C(CH_3){=}CCl_2$, $CH{=}CBr_2$, $C(CH_3){=}CBr_2$, $C(CH_3){=}CF_2$, $CH{=}CFCl$, $CH{=}CFBr$, $C(CH_3){=}CFCl$, $C(CH_3){=}CFBr$, $CH{=}CFMe$, $CH{=}CBrMe$, $CH{=}CClMe$, $CH{=}CHBr$, $CH{=}CHF$, $CH{=}CHCl$, $CF{=}CF_2$, $CCl{=}CF_2$, $CCl{=}CH_2$, $CBr{=}CH_2$, $CF{=}CH_2$, $C(CF_3){=}CFBr$, $C(CP_3){=}CFCl$, $C(CF_3){=}CBr_2$, $C(CF_3){=}CCl_2$, $C(CF_3){=}CF_2$, $C(CF_3){=}CH_2$, $CF{=}CHF$, $CH{=}CHCF_3$, $CH{=}CFCF_2Cl$, $CH{=}CClCF_2Cl$, $CH{=}CBrCF_2Cl$, $CH{=}C(CF_3)_2$, $CH{=}CHC_2F_5$, $CH{=}CHCF(CF_3)_2$, $C(CH_3){=}CHCF_3$, $C(CH_3){=}CFCF_3$, $C(CH_3){=}CClCF_3$, $C(CH_3){=}CBrCF_3$, $CH{=}CClCF_3$, $CH{=}CClC_2F_5$, $CH{=}CBrCF_3$, $CH{=}CFC_2F_5$, $CH{=}CFCF_3$, $CH_2CH{=}CH_2$, $CH_2CH{=}CF_2$, $CH_2CH{=}CCl_2$, $CH_2CH{=}CBr_2$, $CH_2CH{=}CFBr$, $CH_2CH{=}CFCl$, $CH_2CH{=}CClCF_3$, $CH_2CH{=}CHSiMe_3$, $C{\equiv}CH$, $C{\equiv}CSiMe_3$, $C{\equiv}CSiEt_3$, $C{\equiv}CSiMe_2C(CH_3)_3$, $C{\equiv}CCl$, $C{\equiv}CBr$, $C{\equiv}CF$, $C{\equiv}CCF_3$, $C{\equiv}CCF_2H$, $C{\equiv}CCF_2Cl$, $C{\equiv}CCF_2Me$, $C{\equiv}CCF_2Et$, $C{\equiv}CCHFCl$, $C{\equiv}CCF_2Br$, $C{\equiv}CC_2F_5$, $C{\equiv}CCF(CF_3)_2$, $C{\equiv}CCHF(CF_3)$, $C{\equiv}CCH_2F$, $C{\equiv}CCH(Me)F$, $C{\equiv}CCH(Et)F$, $C{\equiv}CMe$, $C{\equiv}CCH_2Me$, $C{\equiv}CCHMe_2$, $C{\equiv}CCH_2CHMe_2$, $C{\equiv}CCMe_3$, $C{\equiv}CCH_2CMe_3$, $C{\equiv}CCH_2SiMe_3$, $C{\equiv}CCMe_2Cl$, $C{\equiv}CCMe_2F$, $C{\equiv}CCH_2OMe$, $C{\equiv}CCH_2CF_3$, $C{\equiv}CCMe_2OMe$, $C{\equiv}CCMe_2OH$, $C{\equiv}CCMe_2OCOMe$, $C{\equiv}CC(Me){=}CH_2$, $C{\equiv}CCF{=}CF_2$, $C{\equiv}C$(cyclopropyl), $C{\equiv}C$(cyclopentyl), $C{\equiv}C$(1-F-cyclopentyl), $CH_2C{\equiv}CH$, $CF_2C{\equiv}CH$, $CHFC{\equiv}CH$, $CH(CF_3)C{\equiv}CH$, $CH_2C{\equiv}CCMe_3$ or $CH_2C{\equiv}CSiMe_3$.

Even more preferably $R^6$ is $CH{=}CF_2$, $CH{=}CCl_2$, $C(CH_3){=}CCl_2$, $CH{=}CBr_2$, $C(CH_3){=}CBr_2$, $C(CH_3){=}CF_2$, $CH{=}CFCl$, $CH{=}CFBr$, $C(CH_3){=}CFCl$, $C(CH_3){=}CFBr$, $CH{=}CHBr$, $CH{=}CHF$, $CH{=}CHCl$, $CCl{=}CH_2$, $CH{=}CHCF_3$, $CH{=}CFCF_2Cl$, $CH{=}CClCP_2Cl$, $CH{=}CBrCF_2Cl$, $CH{=}C(CF_3)_2$, $CH{=}CHC_2F_5$, $CH{=}CHCF(CF_3)_2$, $C(CH_3){=}CHCF_3$, $CH{=}CClCF_3$, $CH{=}CClC_2F_5$, $CH{=}CFC_2F_5$, $CH{=}CBrCF_3$, $CH{=}CFCF_3$, $CH_2CH{=}CClCF_3$, $CH_2CH{=}CCl_2$, $CH_2CH{=}CBr_2$, $C{\equiv}CH$, $C{\equiv}CSiMe_3$, $C{\equiv}CSiEt_3$, $C{\equiv}CSiMe_2C(CH_3)_3$, $C{\equiv}CCl$, $C{\equiv}CCF_3$, $C{\equiv}CCF_2H$, $C{\equiv}CCP_2Cl$, $C{\equiv}CCHFCl$, $C{\equiv}CCF_2Me$, $C{\equiv}CCF_2Et$, $C{\equiv}CCHFEt$, $C{\equiv}CCF_2Br$, $C{\equiv}CCF(CF_3)_2$, $C{\equiv}CCF_2CF_3$, $C{\equiv}CCHF(CF_3)$, $C{\equiv}CCH_2F$, $C{\equiv}CCH(Me)F$, $C{\equiv}CMe$, $C{\equiv}CCHMe_2$, $C{\equiv}CCH_2Me$, $C{\equiv}CCH_2CHMe_2$, $C{\equiv}CCMe_3$, $C{\equiv}CCH_2CMe_3$, $C{\equiv}CCMe_2F$, $C{\equiv}CCH_2CF_3$, $C{\equiv}C$(cyclopropyl), $C{\equiv}C$(cyclopentyl), $C{\equiv}C$(1-F-cyclopentyl), $C{\equiv}CC(Me){=}CH_2$, $C{\equiv}CCF{=}CF_2$, $C{\equiv}CCH_2SiMe_3$, $CH_2C{\equiv}CH$, $CF_2C{\equiv}CH$ or $CHFC{\equiv}CH$.

Yet more preferably $R^6$ is $CH{=}CF_2$, $CH{=}CCl_2$, $CH{=}CBr_2$, $CH{=}CFCl$, $CH{=}CFBr$, $CH{=}CHBr$, $CH{=}CHF$, $CH{=}CHCl$, $CCl{=}CH_2$, $CH{=}CHCF_3$, $CH{=}CFCF_2Cl$, $CH{=}CClCF_2Cl$, $CH{=}CBrCF_2Cl$, $CH{=}C(CF_3)_2$, $CH{=}CHC_2F_5$, $CH{=}CClCF_3$, $CH{=}CBrCF_3$, $CH{=}CFCF_3$, $C{\equiv}CH$, $C{\equiv}CSiMe_3$, $C{\equiv}CCl$, $C{\equiv}CCF_3$, $C{\equiv}CCF_2H$, $C{\equiv}CCHFCl$, $C{\equiv}CCHF(CF_3)$, $C{\equiv}CCF_2Cl$, $C{\equiv}CCF_2Me$, $C{\equiv}CCF_2Br$, $C{\equiv}CCF_2CF_3$, $C{\equiv}CCH_2F$, $C{\equiv}CCH(Me)F$, $C{\equiv}CMe$, $C{\equiv}CCHMe_2$, $C{\equiv}CCH_2CHMe_2$, $C{\equiv}CCMe_3$, $C{\equiv}CCCH_2CMe_3$, $C{\equiv}CCMe_2F$, $C{\equiv}CCH_2CF_3$, $C{\equiv}C$(cyclopropyl), $C{\equiv}C$(cyclopentyl), $C{\equiv}C$(1-F-cyclopentyl), $CH_2C{\equiv}CH$, $CF_2C{\equiv}CH$, $CHFC{\equiv}CH$ or $C{\equiv}CCH_2Me$.

Most preferably $R^6$ is $C{\equiv}CCMe_3$.

Preferably nitrogen atoms in $Het^1$ are, independently, either unsubstituted or substituted by $R^{y1}$.

When $R^{y1}$ is a substituent on a nitrogen atom it is preferably $C_{1-3}$ alkyl, $C_{1-3}$ haloalkyl or methoxymethylene; more preferably $C_{1-2}$ alkyl, $CF_3$, $CF_2Cl$, $CHF_2$, $CH_2F$ or methoxymethylene; even more preferably methyl, $CHF_2$ or methoxymethylene; yet more preferably methyl or methoxymethylene; and most preferably methyl.

Preferably carbon atoms in $Het^1$ which are not bonded to the atom substituted by $CXNR^1$ are, independently, either unsubstituted or substituted by $R^{y1}$.

When $R^{y1}$ is a substituent on a carbon atom which is not bonded to the atom substituted by $CXNR^1$ it is preferably halogen, $C_{1-3}$ alkyl, $C_{1-3}$ haloalkyl or methoxymethylene; more preferably chloro, methoxymethylene, $CH_3$, $CHF_2$ or $CF_3$; yet more preferably chloro, $CH_3$, $CHF_2$ or $CF_3$; and even more preferably $CH_3$ or $CF_3$.

There may be one or two carbon atoms in the $Het^1$ ring bonded to the atom substituted by $CXNR^1$; preferably such carbon atoms are, independently, either unsubstituted or substituted by $R^{y1}$.

When $R^{y1}$ is a substituent on a carbon atom bonded in the $Het^1$ ring to the atom substituted by $CXNR^1$ it is preferably halogen, $C_{1-3}$ alkyl or $C_{1-3}$ haloalkyl; more preferably chloro, fluoro, bromo, $C_{1-2}$ alkyl, $CF_3$, $CF_2Cl$, $CHF_2$, $CH_2F$; and even more preferably chloro, fluoro, bromo, methyl, $CF_3$, $CHF_2$ or $CH_2F$.

More preferably, when there is only one carbon atom in $Het^1$ bonded to the atom substituted by $CXNR^1$ that carbon atom is substituted by $R^{y1}$.

More preferably, when there are two carbon atoms in $Het^1$ bonded to the atom substituted by $CXNR^1$ one such carbon atom is substituted by $R^{y1}$ and the other carbon atom is either unsubstituted or is substituted by fluoro, chloro or methyl.

Preferably carbon atoms and heteroatoms in $Het^2$ which are not bound to $R^6$ are, independently, either unsubstituted or are substituted by $R^2$. When a carbon atom or a heteroatom in $Het^2$ is substituted by $R^{y2}$, $R^{y2}$ is preferably halogen, $C_{1-3}$ alkyl, $C_{1-3}$ haloalkyl or cyano; more preferably fluoro, chloro, $CH_3$ or $CF_3$; and even more preferably chloro or $CF_3$.

In a preferred embodiment of the invention $Het^2$ is only substituted by $R^6$ and not further substituted by any $R^{y2}$.

Preferably m is 0.

Preferably X is O.

Compounds of formula (II):

(II)

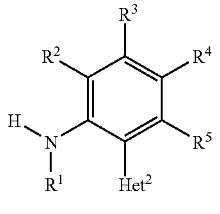

where $R^1$, $R^2$, $R^3$, $R^4$, $R^5$ and $Het^2$ are as defined above for a compound of formula (I), are also novel and are useful as intermediates in the preparation of compounds of formula (I).

Therefore, in another aspect the present invention provides a compound of formula (II), where $R^1$, $R^2$, $R^3$, $R^4$, $R^5$ and $Het^2$ are as defined above for a compound of formula (I).

The preferred values for $R^1$, $R^2$, $R^3$, $R^4$, $R^5$ and $Het^2$ for a compound of formula (II) are as defined above for a compound of formula (I).

Compounds of formula (III):

(III)

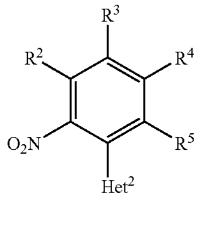

where $R^2$, $R^3$, $R^4$, $R^5$ and $Het^2$ are as defined above for a compound of formula (I) are also novel and are useful as intermediates in the preparation of compounds of formula (II).

Therefore, in another aspect the present invention provides a compound of formula (III), where $R^2$, $R^3$, $R^4$, $R^5$ and $Het^2$ are as defined above for a compound of formula (I).

The preferred values for $R^2$, $R^3$, $R^4$, $R^5$ and $Het^2$ for a compound of formula (III) are as defined above for a compound of formula (I).

Compounds of formula (IV):

(IV)

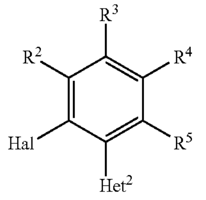

where $R^2$, $R^3$, $R^4$, $R^5$ and $Het^2$ are as defined above for a compound of formula (I) and Hal is bromo, chloro or iodo are also novel and are useful as intermediates in the preparation of compounds of formula (I).

Therefore, in another aspect the present invention provides a compound of formula (IV), where $R^2$, $R^3$, $R^4$, $R^5$ and $Het^2$ are as defined above for a compound of formula (I) and Hal is bromo, chloro or iodo.

The preferred values for $R^2$, $R^3$, $R^4$, $R^5$ and $Het^2$ for a compound of formula (IV) are as defined above for a compound of formula (I).

The compounds of formulae (I), (II), (III) and (IV) may exist as different geometric or optical isomers or in different tautomeric forms. For each formula, this invention covers all such isomers and tautomers and mixtures thereof in all proportions as well as isotopic forms such as deuterated compounds.

The compounds in Tables 1 to 7 below illustrate compounds of the invention.

Table 1X represents Table 1aa (when X is aa), represents Table 1ab (when X is ab), represents Table 1ac (when X is ac), represents Table 1ad (when X is ad), represents Table 1ae (when X is ae), represents Table 1af (when X is af), represents Table 1ag (when X is ag), represents Table 1ah (when X is ah), represents Table 1ai (when X is ai), represents Table 1aj (when X is aj), represents Table 1ak (when X is ak), represents Table 1al (when X is al), represents Table 1am (when X is am), represents Table 1an (when X is an), represents Table 1ao (when X is ao), represents Table 1ap (when X is ap), represents Table 1aq (when X is aq), represents Table 1ar (when X is ar), represents Table 1as (when X is as), represents Table 1at (when X is at), represents Table 1au (when X is au), represents Table 1av (when X is av), represents Table 1aw (when X is aw) and represents Table 1ax (when X is ax).

TABLE 1X

| Compound No. | $R^1$ | $R^6$ | $R^7$ | $R^8$ | $R^9$ | X |
|---|---|---|---|---|---|---|
| 1X.001 | H | C≡CH | H | Me | $CF_3$ | O |
| 1X.002 | H | C≡CH | H | Me | $CF_2H$ | O |
| 1X.003 | H | C≡CH | F | Me | Me | O |
| 1X.004 | H | C≡CH | H | Me | $CF_3$ | S |
| 1X.005 | H | C≡CH | H | Me | $CF_2H$ | S |
| 1X.006 | propargyl | C≡CH | H | Me | $CF_3$ | O |
| 1X.007 | allenyl | C≡CH | H | Me | $CF_3$ | O |
| 1X.008 | COMe | C≡CH | H | Me | $CF_3$ | O |
| 1X.009 | H | C≡CF | H | Me | $CF_3$ | O |
| 1X.010 | H | C≡CF | H | Me | $CF_2H$ | O |
| 1X.011 | H | C≡CF | F | Me | Me | O |
| 1X.012 | H | C≡CCl | H | Me | $CF_3$ | O |
| 1X.013 | H | C≡CCl | H | Me | $CF_2H$ | O |
| 1X.014 | H | C≡CCl | F | Me | Me | O |
| 1X.015 | H | C≡CBr | H | Me | $CF_3$ | O |
| 1X.016 | H | C≡CBr | H | Me | $CF_2H$ | O |
| 1X.017 | H | C≡CBr | F | Me | Me | O |
| 1X.018 | H | C≡CMe | H | Me | $CF_3$ | O |
| 1X.019 | H | C≡CMe | H | Me | $CF_2H$ | O |
| 1X.020 | H | C≡CMe | F | Me | Me | O |
| 1X.021 | H | C≡CCH$_2$OMe | H | Me | $CF_3$ | O |
| 1X.022 | H | C≡CCH$_2$OMe | H | Me | $CF_2H$ | O |
| 1X.023 | H | C≡CCH$_2$OMe | F | Me | Me | O |
| 1X.024 | H | C≡CCH$_2$F | H | Me | $CF_3$ | O |
| 1X.025 | H | C≡CCH$_2$F | H | Me | $CF_2H$ | O |
| 1X.026 | H | C≡CCH$_2$F | F | Me | Me | O |
| 1X.027 | H | C≡CCF$_2$H | H | Me | $CF_3$ | O |
| 1X.028 | H | C≡CCF$_2$H | H | Me | $CF_2H$ | O |
| 1X.029 | H | C≡CCF$_2$H | F | Me | Me | O |
| 1X.030 | H | C≡CCHFCl | H | Me | $CF_3$ | O |
| 1X.031 | H | C≡CCHFCl | H | Me | $CF_2H$ | O |
| 1X.032 | H | C≡CCHFCl | F | Me | Me | O |
| 1X.033 | H | C≡CCF$_2$Cl | H | Me | $CF_3$ | O |
| 1X.034 | H | C≡CCF$_2$Cl | H | Me | $CF_2H$ | O |
| 1X.035 | H | C≡CCF$_2$Cl | F | Me | Me | O |
| 1X.036 | H | C≡CCF$_2$Br | H | Me | $CF_3$ | O |
| 1X.037 | H | C≡CCF$_2$Br | H | Me | $CF_2H$ | O |
| 1X.038 | H | C≡CCF$_2$Br | F | Me | Me | O |
| 1X.039 | H | C≡CCF$_3$ | H | Me | $CF_3$ | O |
| 1X.040 | H | C≡CCF$_3$ | H | Me | $CF_2H$ | O |
| 1X.041 | H | C≡CCF$_3$ | F | Me | Me | O |
| 1X.042 | H | C≡CCF$_3$ | H | Me | $CF_3$ | S |
| 1X.043 | H | C≡CCF$_3$ | H | Me | $CF_2H$ | S |
| 1X.044 | propargyl | C≡CCF$_3$ | H | Me | $CF_3$ | O |
| 1X.045 | allenyl | C≡CCF$_3$ | H | Me | $CF_3$ | O |
| 1X.046 | COMe | C≡CCF$_3$ | H | Me | $CF_3$ | O |
| 1X.047 | H | C≡CCH$_2$CH$_3$ | H | Me | $CF_3$ | O |
| 1X.048 | H | C≡CCH$_2$CH$_3$ | H | Me | $CF_2H$ | O |
| 1X.049 | H | C≡CCH$_2$CH$_3$ | F | Me | Me | O |
| 1X.050 | H | C≡CCH(Me)F | H | Me | $CF_3$ | O |
| 1X.051 | H | C≡CCH(Me)F | H | Me | $CF_2H$ | O |
| 1X.052 | H | C≡CCH(Me)F | F | Me | Me | O |
| 1X.053 | H | C≡CCF$_2$Me | H | Me | $CF_3$ | O |
| 1X.054 | H | C≡CCF$_2$Me | H | Me | $CF_2H$ | O |
| 1X.055 | H | C≡CCF$_2$Me | F | Me | Me | O |
| 1X.056 | H | C≡CCH$_2$CF$_3$ | H | Me | $CF_3$ | O |
| 1X.057 | H | C≡CCH$_2$CF$_3$ | H | Me | $CF_2H$ | O |
| 1X.058 | H | C≡CCH$_2$CF$_3$ | F | Me | Me | O |
| 1X.059 | H | C≡CC$_2$F$_5$ | H | Me | $CF_3$ | O |
| 1X.060 | H | C≡CC$_2$F$_5$ | H | Me | $CF_2H$ | O |
| 1X.061 | H | C≡CC$_2$F$_5$ | F | Me | Me | O |
| 1X.062 | H | C≡CCF═CF$_2$ | H | Me | $CF_3$ | O |
| 1X.063 | H | C≡CCF═CF$_2$ | H | Me | $CF_2H$ | O |
| 1X.064 | H | C≡CCF═CF$_2$ | F | Me | Me | O |
| 1X.065 | H | C≡CCH$_2$CH$_2$CH$_3$ | H | Me | $CF_3$ | O |
| 1X.066 | H | C≡CCH$_2$CH$_2$CH$_3$ | H | Me | $CF_2H$ | O |
| 1X.067 | H | C≡CCH$_2$CH$_2$CH$_3$ | F | Me | Me | O |
| 1X.068 | H | C≡CCHFCH$_2$CH$_3$ | H | Me | $CF_3$ | O |
| 1X.069 | H | C≡CCHFCH$_2$CH$_3$ | H | Me | $CF_2H$ | O |
| 1X.070 | H | C≡CCHFCH$_2$CH$_3$ | F | Me | Me | O |
| 1X.071 | H | C≡CCF$_2$CH$_2$CH$_3$ | H | Me | $CF_3$ | O |
| 1X.072 | H | C≡CCF$_2$CH$_2$CH$_3$ | H | Me | $CF_2H$ | O |

TABLE 1X-continued

| Compound No. | $R^1$ | $R^6$ | $R^7$ | $R^8$ | $R^9$ | X |
|---|---|---|---|---|---|---|
| 1X.073 | H | C≡CCF$_2$CH$_2$CH$_3$ | F | Me | Me | O |
| 1X.074 | H | C≡CCH(Me)$_2$ | H | Me | $CF_3$ | O |
| 1X.075 | H | C≡CCH(Me)$_2$ | H | Me | $CF_2H$ | O |
| 1X.076 | H | C≡CCH(Me)$_2$ | F | Me | Me | O |
| 1X.077 | H | C≡CCMe$_2$OMe | H | Me | $CF_3$ | O |
| 1X.078 | H | C≡CCMe$_2$OMe | H | Me | $CF_2H$ | O |
| 1X.079 | H | C≡CCMe$_2$OMe | F | Me | Me | O |
| 1X.080 | H | C≡CC(Me)$_2$F | H | Me | $CF_3$ | O |
| 1X.081 | H | C≡CC(Me)$_2$F | H | Me | $CF_2H$ | O |
| 1X.082 | H | C≡CC(Me)$_2$F | F | Me | Me | O |
| 1X.083 | H | C≡CCF(CF$_3$)$_2$ | H | Me | $CF_3$ | O |
| 1X.084 | H | C≡CCF(CF$_3$)$_2$ | H | Me | $CF_2H$ | O |
| 1X.085 | H | C≡CCF(CF$_3$)$_2$ | F | Me | Me | O |
| 1X.086 | H | C≡CC(Me)═CH$_2$ | H | Me | $CF_3$ | O |
| 1X.087 | H | C≡CC(Me)═CH$_2$ | H | Me | $CF_2H$ | O |
| 1X.088 | H | C≡CC(Me)═CH$_2$ | F | Me | Me | O |
| 1X.089 | H | C≡C(cyclopropyl) | H | Me | $CF_3$ | O |
| 1X.090 | H | C≡C(cyclopropyl) | H | Me | $CHF_2$ | O |
| 1X.091 | H | C≡C(cyclopropyl) | F | Me | Me | O |
| 1X.092 | H | C≡CCH$_2$CH(Me)$_2$ | H | Me | $CF_3$ | O |
| 1X.093 | H | C≡CCH$_2$CH(Me)$_2$ | H | Me | $CF_2H$ | O |
| 1X.094 | H | C≡CCH$_2$CH(Me)$_2$ | F | Me | Me | O |
| 1X.095 | H | C≡CCH(Me)CH$_2$CH$_3$ | H | Me | $CF_3$ | O |
| 1X.096 | H | C≡CCH(Me)CH$_2$CH$_3$ | H | Me | $CF_2H$ | O |
| 1X.097 | H | C≡CCH(Me)CH$_2$CH$_3$ | F | Me | Me | O |
| 1X.098 | H | C≡CCMe$_3$ | H | Me | $CF_3$ | O |
| 1X.099 | H | C≡CCMe$_3$ | H | Me | $CF_2H$ | O |
| 1X.100 | H | C≡CCMe$_3$ | F | Me | Me | O |
| 1X.101 | H | C≡CCMe$_3$ | H | Me | $CF_3$ | S |
| 1X.102 | H | C≡CCMe$_3$ | H | Me | $CF_2H$ | S |
| 1X.103 | propargyl | C≡CCMe$_3$ | H | Me | $CF_3$ | O |
| 1X.104 | allenyl | C≡CCMe$_3$ | H | Me | $CF_3$ | O |
| 1X.105 | COMe | C≡CCMe$_3$ | H | Me | $CF_3$ | O |
| 1X.106 | H | C≡CSiMe$_3$ | H | Me | $CF_3$ | O |
| 1X.107 | H | C≡CSiMe$_3$ | H | Me | $CF_2H$ | O |
| 1X.108 | H | C≡CSiMe$_3$ | F | Me | Me | O |
| 1X.109 | H | C≡CCH$_2$C(Me)$_3$ | H | Me | $CF_3$ | O |
| 1X.110 | H | C≡CCH$_2$C(Me)$_3$ | H | Me | $CF_2H$ | O |
| 1X.111 | H | C≡CCH$_2$C(Me)$_3$ | F | Me | Me | O |
| 1X.112 | H | C≡CCH$_2$SiMe$_3$ | H | Me | $CF_3$ | O |
| 1X.113 | H | C≡CCH$_2$SiMe$_3$ | H | Me | $CF_2H$ | O |
| 1X.114 | H | C≡CCH$_2$SiMe$_3$ | F | Me | Me | O |
| 1X.115 | H | C≡C(1-F-cyclopentyl) | H | Me | $CF_3$ | O |
| 1X.116 | H | C≡C(1-F-cyclopentyl) | H | Me | $CHF_2$ | O |
| 1X.117 | H | C≡C(1-F-cyclopentyl) | F | Me | Me | O |
| 1X.118 | H | C≡CSi(Me$_2$)CMe$_3$ | H | Me | $CF_3$ | O |
| 1X.119 | H | C≡CSi(Me$_2$)CMe$_3$ | H | Me | $CF_2H$ | O |
| 1X.120 | H | C≡CSi(Me$_2$)CMe$_3$ | F | Me | Me | O |
| 1X.121 | H | CH$_2$C≡CH | H | Me | $CF_3$ | O |
| 1X.122 | H | CH$_2$C≡CH | H | Me | $CF_2H$ | O |
| 1X.123 | H | CH$_2$C≡CH | F | Me | Me | O |
| 1X.124 | H | CHFC≡CH | H | Me | $CF_3$ | O |
| 1X.125 | H | CHFC≡CH | H | Me | $CF_2H$ | O |
| 1X.126 | H | CHFC≡CH | F | Me | Me | O |
| 1X.127 | H | CF$_2$C≡CH | H | Me | $CF_3$ | O |
| 1X.128 | H | CF$_2$C≡CH | H | Me | $CF_2H$ | O |
| 1X.129 | H | CF$_2$C≡CH | F | Me | Me | O |
| 1X.130 | H | CHMeC≡CH | H | Me | $CF_3$ | O |
| 1X.131 | H | CHMeC≡CH | H | Me | $CF_2H$ | O |
| 1X.132 | H | CHMeC≡CH | F | Me | Me | O |
| 1X.133 | H | CH(CF$_3$)C≡CH | H | Me | $CF_3$ | O |
| 1X.134 | H | CH(CF$_3$)C≡CH | H | Me | $CF_2H$ | O |
| 1X.135 | H | CH(CF$_3$)C≡CH | F | Me | Me | O |
| 1X.136 | H | CMe$_2$C≡CH | H | Me | $CF_3$ | O |
| 1X.137 | H | CMe$_2$C≡CH | H | Me | $CF_2H$ | O |
| 1X.138 | H | CMe$_2$C≡CH | F | Me | Me | O |
| 1X.139 | H | CH$_2$C≡CMe | H | Me | $CF_3$ | O |
| 1X.140 | H | CH$_2$C≡CMe | H | Me | $CF_2H$ | O |
| 1X.141 | H | CH$_2$C≡CMe | F | Me | Me | O |
| 1X.142 | H | CF$_2$C≡CMe | H | Me | $CF_3$ | O |
| 1X.143 | H | CF$_2$C≡CMe | H | Me | $CF_2H$ | O |
| 1X.144 | H | CF$_2$C≡CMe | F | Me | Me | O |
| 1X.145 | H | CH$_2$C≡CCF$_3$ | H | Me | $CF_3$ | O |
| 1X.146 | H | CH$_2$C≡CCF$_3$ | H | Me | $CF_2H$ | O |
| 1X.147 | H | CH$_2$C≡CCF$_3$ | F | Me | Me | O |
| 1X.148 | H | CF$_2$C≡CCF$_3$ | H | Me | $CF_3$ | O |

TABLE 1X-continued

| Compound No. | $R^1$ | $R^6$ | $R^7$ | $R^8$ | $R^9$ | X |
|---|---|---|---|---|---|---|
| 1X.149 | H | $CF_2C\equiv CCF_3$ | H | Me | $CF_2H$ | O |
| 1X.150 | H | $CF_2C\equiv CCF_3$ | F | Me | Me | O |
| 1X.151 | H | $CH_2C\equiv CCMe_3$ | H | Me | $CF_3$ | O |
| 1X.152 | H | $CH_2C\equiv CCMe_3$ | H | Me | $CF_2H$ | O |
| 1X.153 | H | $CH_2C\equiv CCMe_3$ | F | Me | Me | O |
| 1X.154 | H | $CF_2C\equiv CCMe_3$ | H | Me | $CF_3$ | O |
| 1X.155 | H | $CF_2C\equiv CCMe_3$ | H | Me | $CF_2H$ | O |
| 1X.156 | H | $CF_2C\equiv CCMe_3$ | F | Me | Me | O |
| 1X.157 | H | $CH_2C\equiv CSiMe_3$ | H | Me | $CF_3$ | O |
| 1X.158 | H | $CH_2C\equiv CSiMe_3$ | H | Me | $CF_2H$ | O |
| 1X.159 | H | $CH_2C\equiv CSiMe_3$ | F | Me | Me | O |
| 1X.160 | H | $CF_2C\equiv CSiMe_3$ | H | Me | $CF_3$ | O |
| 1X.161 | H | $CF_2C\equiv CSiMe_3$ | H | Me | $CF_2H$ | O |
| 1X.162 | H | $CF_2C\equiv CSiMe_3$ | F | Me | Me | O |
| 1X.163 | H | $CH{=}CH_2$ | H | Me | $CF_3$ | O |
| 1X.164 | H | $CH{=}CH_2$ | H | Me | $CF_2H$ | O |
| 1X.165 | H | $CH{=}CH_2$ | F | Me | Me | O |
| 1X.166 | H | $CH{=}CH_2$ | H | Me | $CF_3$ | S |
| 1X.167 | H | $CH{=}CH_2$ | H | Me | $CF_2H$ | S |
| 1X.168 | propargyl | $CH{=}CH_2$ | H | Me | $CF_3$ | O |
| 1X.169 | allenyl | $CH{=}CH_2$ | H | Me | $CF_3$ | O |
| 1X.170 | COMe | $CH{=}CH_2$ | H | Me | $CF_3$ | O |
| 1X.171 | H | $CH{=}CHF$ | H | Me | $CF_3$ | O |
| 1X.172 | H | $CH{=}CHF$ | H | Me | $CF_2H$ | O |
| 1X.173 | H | $CH{=}CHF$ | F | Me | Me | O |
| 1X.174 | H | $CH{=}CHCl$ | H | Me | $CF_3$ | O |
| 1X.175 | H | $CH{=}CHCl$ | H | Me | $CF_2H$ | O |
| 1X.176 | H | $CH{=}CHCl$ | F | Me | Me | O |
| 1X.177 | H | $CH{=}CHBr$ | H | Me | $CF_3$ | O |
| 1X.178 | H | $CH{=}CHBr$ | H | Me | $CF_2H$ | O |
| 1X.179 | H | $CH{=}CHBr$ | F | Me | Me | O |
| 1X.180 | H | $CH{=}CF_2$ | H | Me | $CF_3$ | O |
| 1X.181 | H | $CH{=}CF_2$ | H | Me | $CF_2H$ | O |
| 1X.182 | H | $CH{=}CF_2$ | F | Me | Me | O |
| 1X.183 | H | $CH{=}CFCl$ | H | Me | $CF_3$ | O |
| 1X.184 | H | $CH{=}CFCl$ | H | Me | $CF_2H$ | O |
| 1X.185 | H | $CH{=}CFCl$ | F | Me | Me | O |
| 1X.186 | H | $CH{=}CFBr$ | H | Me | $CF_3$ | O |
| 1X.187 | H | $CH{=}CFBr$ | H | Me | $CF_2H$ | O |
| 1X.188 | H | $CH{=}CFBr$ | F | Me | Me | O |
| 1X.189 | H | $CH{=}CCl_2$ | H | Me | $CF_3$ | O |
| 1X.190 | H | $CH{=}CCl_2$ | H | Me | $CF_2H$ | O |
| 1X.191 | H | $CH{=}CCl_2$ | F | Me | Me | O |
| 1X.192 | H | $CH{=}CBr_2$ | H | Me | $CF_3$ | O |
| 1X.193 | H | $CH{=}CBr_2$ | H | Me | $CF_2H$ | O |
| 1X.194 | H | $CH{=}CBr_2$ | F | Me | Me | O |
| 1X.195 | H | $CF{=}CH_2$ | H | Me | $CF_3$ | O |
| 1X.196 | H | $CF{=}CH_2$ | H | Me | $CF_2H$ | O |
| 1X.197 | H | $CF{=}CH_2$ | F | Me | Me | O |
| 1X.198 | H | $CF{=}CHF$ | H | Me | $CF_3$ | O |
| 1X.199 | H | $CF{=}CHF$ | H | Me | $CF_2H$ | O |
| 1X.200 | H | $CF{=}CHF$ | F | Me | Me | O |
| 1X.201 | H | $CF{=}CF_2$ | H | Me | $CF_3$ | O |
| 1X.202 | H | $CF{=}CF_2$ | H | Me | $CF_2H$ | O |
| 1X.203 | H | $CF{=}CF_2$ | F | Me | Me | O |
| 1X.204 | H | $CF{=}CFCl$ | H | Me | $CF_3$ | O |
| 1X.205 | H | $CF{=}CFCl$ | H | Me | $CF_2H$ | O |
| 1X.206 | H | $CF{=}CFCl$ | F | Me | Me | O |
| 1X.207 | H | $CF{=}CFBr$ | H | Me | $CF_3$ | O |
| 1X.208 | H | $CF{=}CFBr$ | H | Me | $CF_2H$ | O |
| 1X.209 | H | $CF{=}CFBr$ | F | Me | Me | O |
| 1X.210 | H | $CF{=}CCl_2$ | H | Me | $CF_3$ | O |
| 1X.211 | H | $CF{=}CCl_2$ | H | Me | $CF_2H$ | O |
| 1X.212 | H | $CF{=}CCl_2$ | F | Me | Me | O |
| 1X.213 | H | $CCl{=}CH_2$ | H | Me | $CF_3$ | O |
| 1X.214 | H | $CCl{=}CH_2$ | H | Me | $CF_2H$ | O |
| 1X.215 | H | $CCl{=}CH_2$ | F | Me | Me | O |
| 1X.216 | H | $CCl{=}CF_2$ | H | Me | $CF_3$ | O |
| 1X.217 | H | $CCl{=}CF_2$ | H | Me | $CF_2H$ | O |
| 1X.218 | H | $CCl{=}CF_2$ | F | Me | Me | O |
| 1X.219 | H | $CBr{=}CH_2$ | H | Me | $CF_3$ | O |
| 1X.220 | H | $CBr{=}CH_2$ | H | Me | $CF_2H$ | O |
| 1X.221 | H | $CBr{=}CH_2$ | F | Me | Me | O |
| 1X.222 | H | $CBr{=}CF_2$ | H | Me | $CF_3$ | O |
| 1X.223 | H | $CBr{=}CF_2$ | H | Me | $CF_2H$ | O |
| 1X.224 | H | $CBr{=}CF_2$ | F | Me | Me | O |

TABLE 1X-continued

| Compound No. | $R^1$ | $R^6$ | $R^7$ | $R^8$ | $R^9$ | X |
|---|---|---|---|---|---|---|
| 1X.225 | H | $CH{=}CHCF_3$ | H | Me | $CF_3$ | O |
| 1X.226 | H | $CH{=}CHCF_3$ | H | Me | $CF_2H$ | O |
| 1X.227 | H | $CH{=}CHCF_3$ | F | Me | Me | O |
| 1X.228 | H | $CH{=}CFCF_3$ | H | Me | $CF_3$ | O |
| 1X.229 | H | $CH{=}CFCF_3$ | H | Me | $CF_2H$ | O |
| 1X.230 | H | $CH{=}CFCF_3$ | F | Me | Me | O |
| 1X.231 | H | $CH{=}CClCF_3$ | H | Me | $CF_3$ | O |
| 1X.232 | H | $CH{=}CClCF_3$ | H | Me | $CF_2H$ | O |
| 1X.233 | H | $CH{=}CClCF_3$ | F | Me | Me | O |
| 1X.234 | H | $CH{=}CBrCF_3$ | H | Me | $CF_3$ | O |
| 1X.235 | H | $CH{=}CBrCF_3$ | H | Me | $CF_2H$ | O |
| 1X.236 | H | $CH{=}CBrCF_3$ | F | Me | Me | O |
| 1X.237 | H | $CH{=}CFCF_2Cl$ | H | Me | $CF_3$ | O |
| 1X.238 | H | $CH{=}CFCF_2Cl$ | H | Me | $CF_2H$ | O |
| 1X.239 | H | $CH{=}CFCF_2Cl$ | F | Me | Me | O |
| 1X.240 | H | $CH{=}CClCF_2Cl$ | H | Me | $CF_3$ | O |
| 1X.241 | H | $CH{=}CClCF_2Cl$ | H | Me | $CF_2H$ | O |
| 1X.242 | H | $CH{=}CClCF_2Cl$ | F | Me | Me | O |
| 1X.243 | H | $CF{=}CHCF_3$ | H | Me | $CF_3$ | O |
| 1X.244 | H | $CF{=}CHCF_3$ | H | Me | $CF_2H$ | O |
| 1X.245 | H | $CF{=}CHCF_3$ | F | Me | Me | O |
| 1X.246 | H | $CF{=}CFCF_3$ | H | Me | $CF_3$ | O |
| 1X.247 | H | $CF{=}CFCF_3$ | H | Me | $CF_2H$ | O |
| 1X.248 | H | $CF{=}CFCF_3$ | F | Me | Me | O |
| 1X.249 | H | $CH{=}CHC_2F_5$ | H | Me | $CF_3$ | O |
| 1X.250 | H | $CH{=}CHC_2F_5$ | H | Me | $CF_2H$ | O |
| 1X.251 | H | $CH{=}CHC_2F_5$ | F | Me | Me | O |
| 1X.252 | H | $CH{=}CFC_2F_5$ | H | Me | $CF_3$ | O |
| 1X.253 | H | $CH{=}CFC_2F_5$ | H | Me | $CF_2H$ | O |
| 1X.254 | H | $CH{=}CFC_2F_5$ | F | Me | Me | O |
| 1X.255 | H | $CH{=}CClC_2F_5$ | H | Me | $CF_3$ | O |
| 1X.256 | H | $CH{=}CClC_2F_5$ | H | Me | $CF_2H$ | O |
| 1X.257 | H | $CH{=}CClC_2F_5$ | F | Me | Me | O |
| 1X.258 | H | $CH{=}C(CF_3)_2$ | H | Me | $CF_3$ | O |
| 1X.259 | H | $CH{=}C(CF_3)_2$ | H | Me | $CF_2H$ | O |
| 1X.260 | H | $CH{=}C(CF_3)_2$ | F | Me | Me | O |
| 1X.261 | H | $CF{=}C(CF_3)_2$ | H | Me | $CF_3$ | O |
| 1X.262 | H | $CF{=}C(CF_3)_2$ | H | Me | $CF_2H$ | O |
| 1X.263 | H | $CF{=}C(CF_3)_2$ | F | Me | Me | O |
| 1X.264 | H | $CH{=}CHSiMe_3$ | H | Me | $CF_3$ | O |
| 1X.265 | H | $CH{=}CHSiMe_3$ | H | Me | $CF_2H$ | O |
| 1X.266 | H | $CH{=}CHSiMe_3$ | F | Me | Me | O |
| 1X.267 | H | $CMe{=}CF_2$ | H | Me | $CF_3$ | O |
| 1X.268 | H | $CMe{=}CF_2$ | H | Me | $CF_2H$ | O |
| 1X.269 | H | $CMe{=}CF_2$ | F | Me | Me | O |
| 1X.270 | H | $CMe{=}CFCl$ | H | Me | $CF_3$ | O |
| 1X.271 | H | $CMe{=}CFCl$ | H | Me | $CF_2H$ | O |
| 1X.272 | H | $CMe{=}CFCl$ | F | Me | Me | O |
| 1X.273 | H | $CMe{=}CFBr$ | H | Me | $CF_3$ | O |
| 1X.274 | H | $CMe{=}CFBr$ | H | Me | $CF_2H$ | O |
| 1X.275 | H | $CMe{=}CFBr$ | F | Me | Me | O |
| 1X.276 | H | $CMe{=}CCl_2$ | H | Me | $CF_3$ | O |
| 1X.277 | H | $CMe{=}CCl_2$ | H | Me | $CF_2H$ | O |
| 1X.278 | H | $CMe{=}CCl_2$ | F | Me | Me | O |
| 1X.279 | H | $CMe{=}CBr_2$ | H | Me | $CF_3$ | O |
| 1X.280 | H | $CMe{=}CBr_2$ | H | Me | $CF_2H$ | O |
| 1X.281 | H | $CMe{=}CBr_2$ | F | Me | Me | O |
| 1X.282 | H | $CMe{=}CHCF_3$ | H | Me | $CF_3$ | O |
| 1X.283 | H | $CMe{=}CHCF_3$ | H | Me | $CF_2H$ | O |
| 1X.284 | H | $CMe{=}CHCF_3$ | F | Me | Me | O |
| 1X.285 | H | $CMe{=}CFCF_3$ | H | Me | $CF_3$ | O |
| 1X.286 | H | $CMe{=}CFCF_3$ | H | Me | $CF_2H$ | O |
| 1X.287 | H | $CMe{=}CFCF_3$ | F | Me | Me | O |
| 1X.288 | H | $CMe{=}CClCF_3$ | H | Me | $CF_3$ | O |
| 1X.289 | H | $CMe{=}CClCF_3$ | H | Me | $CF_2H$ | O |
| 1X.290 | H | $CMe{=}CClCF_3$ | F | Me | Me | O |
| 1X.291 | H | $CCF_3{=}CH_2$ | H | Me | $CF_3$ | O |
| 1X.292 | H | $CCF_3{=}CH_2$ | H | Me | $CF_2H$ | O |
| 1X.293 | H | $CCF_3{=}CH_2$ | F | Me | Me | O |
| 1X.294 | H | $CCF_3{=}CHF$ | H | Me | $CF_3$ | O |
| 1X.295 | H | $CCF_3{=}CHF$ | H | Me | $CF_2H$ | O |
| 1X.296 | H | $CCF_3{=}CHF$ | F | Me | Me | O |
| 1X.297 | H | $CCF_3{=}CHCl$ | H | Me | $CF_3$ | O |
| 1X.298 | H | $CCF_3{=}CHCl$ | H | Me | $CF_2H$ | O |
| 1X.299 | H | $CCF_3{=}CHCl$ | F | Me | Me | O |
| 1X.300 | H | $CCF_3{=}CF_2$ | H | Me | $CF_3$ | O |

TABLE 1X-continued

| Compound No. | $R^1$ | $R^6$ | $R^7$ | $R^8$ | $R^9$ | X |
|---|---|---|---|---|---|---|
| 1X.301 | H | $CCF_3{=}CF_2$ | H | Me | $CF_2H$ | O |
| 1X.302 | H | $CCF_3{=}CF_2$ | F | Me | Me | O |
| 1X.303 | H | $CCF_3{=}CCl_2$ | H | Me | $CF_3$ | O |
| 1X.304 | H | $CCF_3{=}CCl_2$ | H | Me | $CF_2H$ | O |
| 1X.305 | H | $CCF_3{=}CCl_2$ | F | Me | Me | O |
| 1X.306 | H | $CCF_3{=}CBr_2$ | H | Me | $CF_3$ | O |
| 1X.307 | H | $CCF_3{=}CBr_2$ | H | Me | $CF_2H$ | O |
| 1X.308 | H | $CCF_3{=}CBr_2$ | F | Me | Me | O |
| 1X.309 | H | $CH_2CH{=}CF_2$ | H | Me | $CF_3$ | O |
| 1X.310 | H | $CH_2CH{=}CF_2$ | H | Me | $CF_2H$ | O |
| 1X.311 | H | $CH_2CH{=}CF_2$ | F | Me | Me | O |
| 1X.312 | H | $CH_2CH{=}CCl_2$ | H | Me | $CF_3$ | O |
| 1X.313 | H | $CH_2CH{=}CCl_2$ | H | Me | $CF_2H$ | O |
| 1X.314 | H | $CH_2CH{=}CCl_2$ | F | Me | Me | O |
| 1X.315 | H | $CH_2CF{=}CF_2$ | H | Me | $CF_3$ | O |
| 1X.316 | H | $CH_2CF{=}CF_2$ | H | Me | $CF_2H$ | O |
| 1X.317 | H | $CH_2CF{=}CF_2$ | F | Me | Me | O |
| 1X.318 | H | $CH_2CF{=}CCl_2$ | H | Me | $CF_3$ | O |
| 1X.319 | H | $CH_2CF{=}CCl_2$ | H | Me | $CF_2H$ | O |
| 1X.320 | H | $CH_2CF{=}CCl_2$ | F | Me | Me | O |

Table 1aa provides 320 compounds of formula (I.aa):

(I.aa)

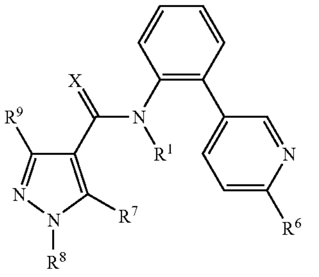

wherein $R^1$, $R^6$, $R^7$, $R^8$, $R^9$ and X are as defined in Table 1aa. An example for a compound disclosed in table 1aa is compound 1aa.001, which is has the following structure:

(1aa.001)

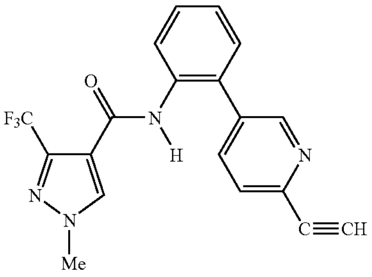

Table 1ab provides 320 compounds of formula (I.ab):

(I.ab)

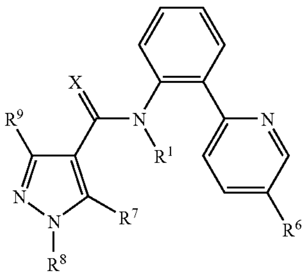

wherein $R^1$, $R^6$, $R^7$, $R^8$, $R^9$ and X are as defined in Table 1ab.

Table 1ac provides 320 compounds of formula (I.ac)

(I.ac)

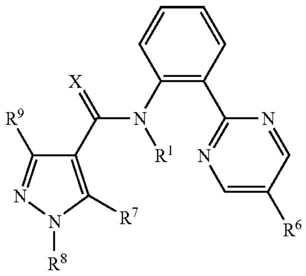

wherein $R^1$, $R^6$, $R^7$, $R^8$, $R^9$ and X are as defined in Table 1ac.

Table 1ad provides 320 compounds of formula (I.ad)

(I.ad)

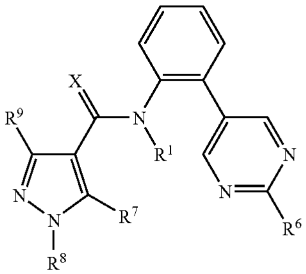

wherein $R^1$, $R^6$, $R^7$, $R^8$, $R^9$ and X are as defined in Table 1ad.

Table 1ae provides 320 compounds of formula (I.ae)

(I.ae)

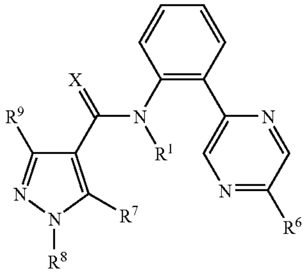

wherein $R^1$, $R^6$, $R^7$, $R^8$, $R^9$ and X are as defined in Table 1ae.

Table 1af provides 320 compounds of formula (I.af)

(I.af)

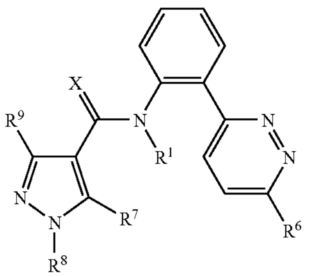

wherein $R^1$, $R^6$, $R^7$, $R^8$, $R^9$ and X are as defined in Table 1af.

Table 1ag provides 320 compounds of formula (I.ag)

(I.ag)

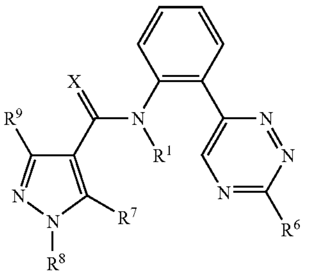

wherein $R^1$, $R^6$, $R^7$, $R^8$, $R^9$ and X are as defined in Table 1ag.

Table 1ah provides 320 compounds of formula (I.ah)

(I.ah)

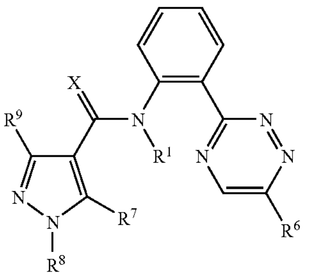

wherein $R^1$, $R^6$, $R^7$, $R^8$, $R^9$ and X are as defined in Table 1ah.

Table 1ai provides 320 compounds of formula (I.ai)

(I.ai)

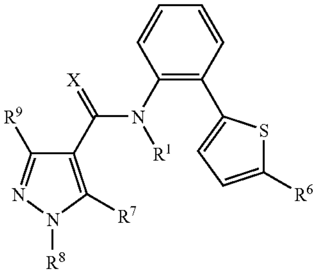

wherein $R^1$, $R^6$, $R^7$, $R^8$, $R^9$ and X are as defined in Table 1ai.

Table 1aj provides 320 compounds of formula (I.aj)

(I.aj)

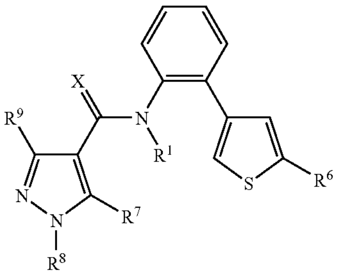

wherein $R^1$, $R^6$, $R^7$, $R^8$, $R^9$ and X are as defined in Table 1aj.

Table 1ak provides 320 compounds of formula (I.ak)

(I.ak)

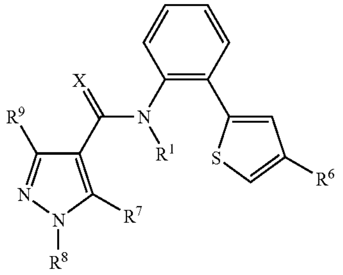

wherein $R^1$, $R^6$, $R^7$, $R^8$, $R^9$ and X are as defined in Table 1ak.

Table 1al provides 320 compounds of formula (I.al)

(I.al)

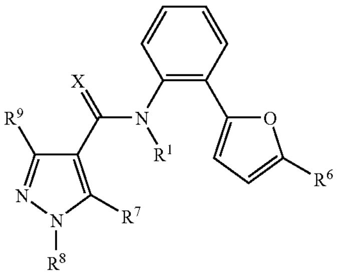

wherein $R^1$, $R^6$, $R^7$, $R^8$, $R^9$ and X are as defined in Table 1al.

Table 1am provides 320 compounds of formula (I.am)

(I.am)

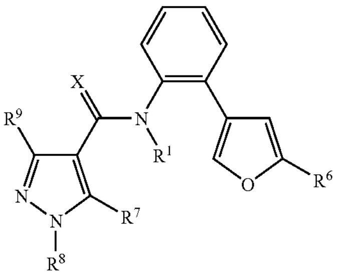

wherein $R^1$, $R^6$, $R^7$, $R^8$, $R^9$ and X are as defined in Table 1am.

Table 1an provides 320 compounds of formula (I.an)

(I.an)

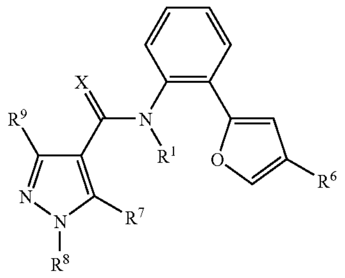

wherein $R^1$, $R^6$, $R^7$, $R^8$, $R^9$ and X are as defined in Table 1an.

Table 1ao provides 320 compounds of formula (I.ao)

(I.ao)

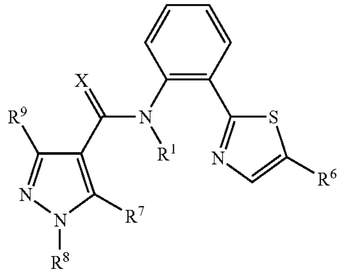

wherein $R^1$, $R^6$, $R^7$, $R^8$, $R^9$ and X are as defined in Table 1ao.

Table 1ap provides 320 compounds of formula (I.ap)

(I.ap)

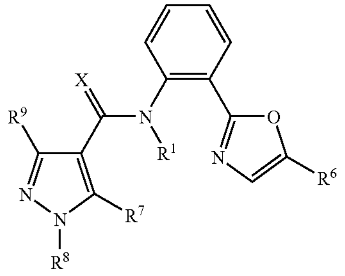

wherein $R^1$, $R^6$, $R^7$, $R^8$, $R^9$ and X are as defined in Table 1ap.

Table 1aq provides 320 compounds of formula (I.aq)

(I.aq)

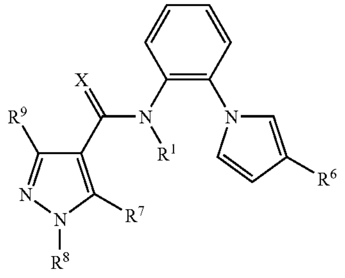

wherein $R^1$, $R^6$, $R^7$, $R^8$, $R^9$ and X are as defined in Table 1aq.

Table 1ar provides 320 compounds of formula (I.ar)

(I.ar)

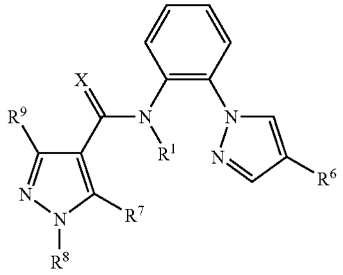

wherein $R^1$, $R^6$, $R^7$, $R^8$, $R^9$ and X are as defined in Table 1ar.

Table 1as provides 320 compounds of formula (I.as)

(I.as)

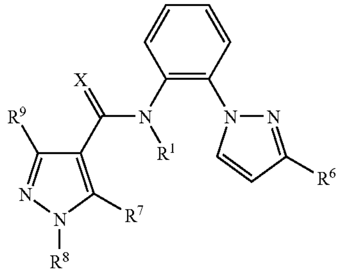

wherein $R^1$, $R^6$, $R^7$, $R^8$, $R^9$ and X are as defined in Table 1as.

Table 1at provides 320 compounds of formula (I.at)

(I.at)

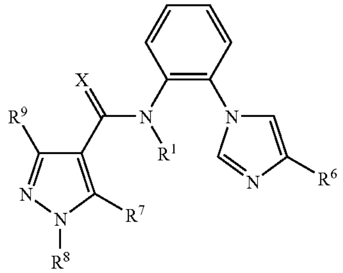

wherein $R^1$, $R^6$, $R^7$, $R^8$, $R^9$ and X are as defined in Table 1at.

Table 1au provides 320 compounds of formula (I.au)

(I.au)

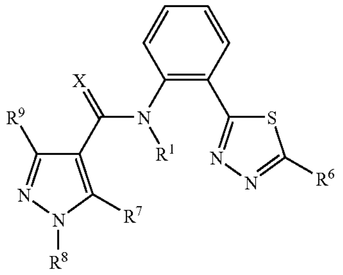

wherein $R^1$, $R^6$, $R^7$, $R^8$, $R^9$ and X are as defined in Table 1au.

Table 1av provides 320 compounds of formula (I.av)

(I.av)

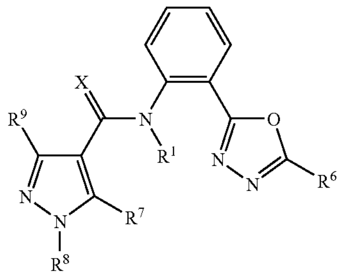

wherein $R^1$, $R^6$, $R^7$, $R^8$, $R^9$ and X are as defined in Table 1av.

Table 1aw provides 320 compounds of formula (I.aw)

(I.aw)

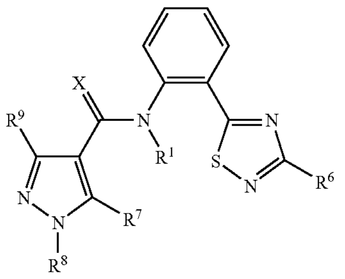

wherein $R^1$, $R^6$, $R^7$, $R^8$, $R^9$ and X are as defined in Table 1aw.

Table 1ax provides 320 compounds of formula (I.ax)

(I.ax)

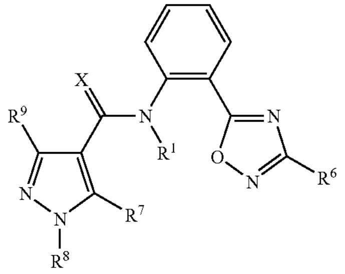

wherein $R^1$, $R^6$, $R^7$, $R^8$, $R^9$ and X are as defined in Table 1ax.

Table 2X represents Table 2ba (when X is ba), represents Table 2bb (when X is bb), represents Table 2bc (when X is bc), represents Table 2bd (when X is bd), represents Table 2be (when X is be), represents Table 2bf (when X is bf), represents Table 2bg (when X is bg), represents Table 2bh (when X is bh), represents Table 2bi (when X is bi), represents Table 2bj (when X is bj), represents Table 2bk (when X is bk), represents Table 2bl (when X is bl), represents Table 2bm (when X is bm), represents Table 2bn (when X is bn), represents Table 2bo (when X is bo), represents Table 2 bp (when X is bp), represents Table 2bq (when X is bq), represents Table 2br (when X is br), represents Table 2bs (when X is bs), represents Table 2bt (when X is bt), represents Table 2bu (when X is bu), represents Table 2by (when X is bv), represents Table 2bw (when X is bw) and represents Table 2bx (when X is bx).

TABLE 2X

| Compound No. | $R^1$ | $R^6$ | $R^7$ | $R^8$ | $R^9$ | X |
|---|---|---|---|---|---|---|
| 2X.001 | H | $C{\equiv}CH$ | H | Me | $CF_3$ | O |
| 2X.002 | H | $C{\equiv}CH$ | H | Me | $CF_2H$ | O |
| 2X.003 | H | $C{\equiv}CH$ | F | Me | Me | O |
| 2X.004 | H | $C{\equiv}CH$ | H | Me | $CF_3$ | S |
| 2X.005 | H | $C{\equiv}CH$ | H | Me | $CF_2H$ | S |
| 2X.006 | propargyl | $C{\equiv}CH$ | H | Me | $CF_3$ | O |
| 2X.007 | allenyl | $C{\equiv}CH$ | H | Me | $CF_3$ | O |
| 2X.008 | COMe | $C{\equiv}CH$ | H | Me | $CF_3$ | O |
| 2X.009 | H | $C{\equiv}CF$ | H | Me | $CF_3$ | O |
| 2X.010 | H | $C{\equiv}CF$ | H | Me | $CF_2H$ | O |
| 2X.011 | H | $C{\equiv}CF$ | F | Me | Me | O |
| 2X.012 | H | $C{\equiv}CCl$ | H | Me | $CF_3$ | O |
| 2X.013 | H | $C{\equiv}CCl$ | H | Me | $CF_2H$ | O |
| 2X.014 | H | $C{\equiv}CCl$ | F | Me | Me | O |
| 2X.015 | H | $C{\equiv}CBr$ | H | Me | $CF_3$ | O |
| 2X.016 | H | $C{\equiv}CBr$ | H | Me | $CF_2H$ | O |
| 2X.017 | H | $C{\equiv}CBr$ | F | Me | Me | O |
| 2X.018 | H | $C{\equiv}CMe$ | H | Me | $CF_3$ | O |
| 2X.019 | H | $C{\equiv}CMe$ | H | Me | $CF_2H$ | O |
| 2X.020 | H | $C{\equiv}CMe$ | F | Me | Me | O |
| 2X.021 | H | $C{\equiv}CCH_2OMe$ | H | Me | $CF_3$ | O |
| 2X.022 | H | $C{\equiv}CCH_2OMe$ | H | Me | $CF_2H$ | O |
| 2X.023 | H | $C{\equiv}CCH_2OMe$ | F | Me | Me | O |
| 2X.024 | H | $C{\equiv}CCH_2F$ | H | Me | $CF_3$ | O |
| 2X.025 | H | $C{\equiv}CCH_2F$ | H | Me | $CF_2H$ | O |
| 2X.026 | H | $C{\equiv}CCH_2F$ | F | Me | Me | O |
| 2X.027 | H | $C{\equiv}CCF_2H$ | H | Me | $CF_3$ | O |
| 2X.028 | H | $C{\equiv}CCF_2H$ | H | Me | $CF_2H$ | O |
| 2X.029 | H | $C{\equiv}CCF_2H$ | F | Me | Me | O |
| 2X.030 | H | $C{\equiv}CCHFCl$ | H | Me | $CF_3$ | O |
| 2X.031 | H | $C{\equiv}CCHFCl$ | H | Me | $CF_2H$ | O |
| 2X.032 | H | $C{\equiv}CCHFCl$ | F | Me | Me | O |
| 2X.033 | H | $C{\equiv}CCF_2Cl$ | H | Me | $CF_3$ | O |
| 2X.034 | H | $C{\equiv}CCF_2Cl$ | H | Me | $CF_2H$ | O |
| 2X.035 | H | $C{\equiv}CCF_2Cl$ | F | Me | Me | O |
| 2X.036 | H | $C{\equiv}CCF_2Br$ | H | Me | $CF_3$ | O |
| 2X.037 | H | $C{\equiv}CCF_2Br$ | H | Me | $CF_2H$ | O |
| 2X.038 | H | $C{\equiv}CCF_2Br$ | F | Me | Me | O |
| 2X.039 | H | $C{\equiv}CCF_3$ | H | Me | $CF_3$ | O |
| 2X.040 | H | $C{\equiv}CCF_3$ | H | Me | $CF_2H$ | O |
| 2X.041 | H | $C{\equiv}CCF_3$ | F | Me | Me | O |
| 2X.042 | H | $C{\equiv}CCF_3$ | H | Me | $CF_3$ | S |
| 2X.043 | H | $C{\equiv}CCF_3$ | H | Me | $CF_2H$ | S |
| 2X.044 | propargyl | $C{\equiv}CCF_3$ | H | Me | $CF_3$ | O |
| 2X.045 | allenyl | $C{\equiv}CCF_3$ | H | Me | $CF_3$ | O |
| 2X.046 | COMe | $C{\equiv}CCF_3$ | H | Me | $CF_3$ | O |
| 2X.047 | H | $C{\equiv}CCH_2CH_3$ | H | Me | $CF_3$ | O |
| 2X.048 | H | $C{\equiv}CCH_2CH_3$ | H | Me | $CF_2H$ | O |
| 2X.049 | H | $C{\equiv}CCH_2CH_3$ | F | Me | Me | O |
| 2X.050 | H | $C{\equiv}CCH(Me)F$ | H | Me | $CF_3$ | O |
| 2X.051 | H | $C{\equiv}CCH(Me)F$ | H | Me | $CF_2H$ | O |
| 2X.052 | H | $C{\equiv}CCH(Me)F$ | F | Me | Me | O |
| 2X.053 | H | $C{\equiv}CCF_2Me$ | H | Me | $CF_3$ | O |
| 2X.054 | H | $C{\equiv}CCF_2Me$ | H | Me | $CF_2H$ | O |
| 2X.055 | H | $C{\equiv}CCF_2Me$ | F | Me | Me | O |
| 2X.056 | H | $C{\equiv}CCH_2CF_3$ | H | Me | $CF_3$ | O |
| 2X.057 | H | $C{\equiv}CCH_2CF_3$ | H | Me | $CF_2H$ | O |
| 2X.058 | H | $C{\equiv}CCH_2CF_3$ | F | Me | Me | O |
| 2X.059 | H | $C{\equiv}CC_2F_5$ | H | Me | $CF_3$ | O |
| 2X.060 | H | $C{\equiv}CC_2F_5$ | H | Me | $CF_2H$ | O |
| 2X.061 | H | $C{\equiv}CC_2F_5$ | F | Me | Me | O |
| 2X.062 | H | $C{\equiv}CCF{=}CF_2$ | H | Me | $CF_3$ | O |
| 2X.063 | H | $C{\equiv}CCF{=}CF_2$ | H | Me | $CF_2H$ | O |
| 2X.064 | H | $C{\equiv}CCF{=}CF_2$ | F | Me | Me | O |
| 2X.065 | H | $C{\equiv}CCH_2CH_2CH_3$ | H | Me | $CF_3$ | O |
| 2X.066 | H | $C{\equiv}CCH_2CH_2CH_3$ | H | Me | $CF_2H$ | O |
| 2X.067 | H | $C{\equiv}CCH_2CH_2CH_3$ | F | Me | Me | O |
| 2X.068 | H | $C{\equiv}CCHFCH_2CH_3$ | H | Me | $CF_3$ | O |
| 2X.069 | H | $C{\equiv}CCHFCH_2CH_3$ | H | Me | $CF_2H$ | O |
| 2X.070 | H | $C{\equiv}CCHFCH_2CH_3$ | F | Me | Me | O |
| 2X.071 | H | $C{\equiv}CCF_2CH_2CH_3$ | H | Me | $CF_3$ | O |
| 2X.072 | H | $C{\equiv}CCF_2CH_2CH_3$ | H | Me | $CF_2H$ | O |
| 2X.073 | H | $C{\equiv}CCF_2CH_2CH_3$ | F | Me | Me | O |
| 2X.074 | H | $C{\equiv}CCH(Me)_2$ | H | Me | $CF_3$ | O |
| 2X.075 | H | $C{\equiv}CCH(Me)_2$ | H | Me | $CF_2H$ | O |
| 2X.076 | H | $C{\equiv}CCH(Me)_2$ | F | Me | Me | O |

TABLE 2X-continued

| Compound No. | $R^1$ | $R^6$ | $R^7$ | $R^8$ | $R^9$ | X |
|---|---|---|---|---|---|---|
| 2X.077 | H | C≡CCMe$_2$OMe | H | Me | CF$_3$ | O |
| 2X.078 | H | C≡CCMe$_2$OMe | H | Me | CF$_2$H | O |
| 2X.079 | H | C≡CCMe$_2$OMe | F | Me | Me | O |
| 2X.080 | H | C≡CC(Me)$_2$F | H | Me | CF$_3$ | O |
| 2X.081 | H | C≡CC(Me)$_2$F | H | Me | CF$_2$H | O |
| 2X.082 | H | C≡CC(Me)$_2$F | F | Me | Me | O |
| 2X.083 | H | C≡CCF(CF$_3$)$_2$ | H | Me | CF$_3$ | O |
| 2X.084 | H | C≡CCF(CF$_3$)$_2$ | H | Me | CF$_2$H | O |
| 2X.085 | H | C≡CCF(CF$_3$)$_2$ | F | Me | Me | O |
| 2X.086 | H | C≡CC(Me)═CH$_2$ | H | Me | CF$_3$ | O |
| 2X.087 | H | C≡CC(Me)═CH$_2$ | H | Me | CF$_2$H | O |
| 2X.088 | H | C≡CC(Me)═CH$_2$ | F | Me | Me | O |
| 2X.089 | H | C≡C(cyclopropyl) | H | Me | CF$_3$ | O |
| 2X.090 | H | C≡C(cyclopropyl) | H | Me | CHF$_2$ | O |
| 2X.091 | H | C≡C(cyclopropyl) | F | Me | Me | O |
| 2X.092 | H | C≡CCH$_2$CH(Me)$_2$ | H | Me | CF$_3$ | O |
| 2X.093 | H | C≡CCH$_2$CH(Me)$_2$ | H | Me | CF$_2$H | O |
| 2X.094 | H | C≡CCH$_2$CH(Me)$_2$ | F | Me | Me | O |
| 2X.095 | H | C≡CCH(Me)CH$_2$CH$_3$ | H | Me | CF$_3$ | O |
| 2X.096 | H | C≡CCH(Me)CH$_2$CH$_3$ | H | Me | CF$_2$H | O |
| 2X.097 | H | C≡CCH(Me)CH$_2$CH$_3$ | F | Me | Me | O |
| 2X.098 | H | C≡CCMe$_3$ | H | Me | CF$_3$ | O |
| 2X.099 | H | C≡CCMe$_3$ | H | Me | CF$_2$H | O |
| 2X.100 | H | C≡CCMe$_3$ | F | Me | Me | O |
| 2X.101 | H | C≡CCMe$_3$ | H | Me | CF$_3$ | S |
| 2X.102 | H | C≡CCMe$_3$ | H | Me | CF$_2$H | S |
| 2X.103 | propargyl | C≡CCMe$_3$ | H | Me | CF$_3$ | O |
| 2X.104 | allenyl | C≡CCMe$_3$ | H | Me | CF$_3$ | O |
| 2X.105 | COMe | C≡CCMe$_3$ | H | Me | CF$_3$ | O |
| 2X.106 | H | C≡CSiMe$_3$ | H | Me | CF$_3$ | O |
| 2X.107 | H | C≡CSiMe$_3$ | H | Me | CF$_2$H | O |
| 2X.108 | H | C≡CSiMe$_3$ | F | Me | Me | O |
| 2X.109 | H | C≡CCH$_2$C(Me)$_3$ | H | Me | CF$_3$ | O |
| 2X.110 | H | C≡CCH$_2$C(Me)$_3$ | H | Me | CF$_2$H | O |
| 2X.111 | H | C≡CCH$_2$C(Me)$_3$ | F | Me | Me | O |
| 2X.112 | H | C≡CCH$_2$SiMe$_3$ | H | Me | CF$_3$ | O |
| 2X.113 | H | C≡CCH$_2$SiMe$_3$ | H | Me | CF$_2$H | O |
| 2X.114 | H | C≡CCH$_2$SiMe$_3$ | F | Me | Me | O |
| 2X.115 | H | C≡C(1-F-cyclopentyl) | H | Me | CF$_3$ | O |
| 2X.116 | H | C≡C(1-F-cyclopentyl) | H | Me | CHF$_2$ | O |
| 2X.117 | H | C≡C(1-F-cyclopentyl) | F | Me | Me | O |
| 2X.118 | H | C≡CSi(Me$_2$)CMe$_3$ | H | Me | CF$_3$ | O |
| 2X.119 | H | C≡CSi(Me$_2$)CMe$_3$ | H | Me | CF$_2$H | O |
| 2X.120 | H | C≡CSi(Me$_2$)CMe$_3$ | F | Me | Me | O |
| 2X.121 | H | CH$_2$C≡CH | H | Me | CF$_3$ | O |
| 2X.122 | H | CH$_2$C≡CH | H | Me | CF$_2$H | O |
| 2X.123 | H | CH$_2$C≡CH | F | Me | Me | O |
| 2X.124 | H | CHFC≡CH | H | Me | CF$_3$ | O |
| 2X.125 | H | CHFC≡CH | H | Me | CF$_2$H | O |
| 2X.126 | H | CHFC≡CH | F | Me | Me | O |
| 2X.127 | H | CF$_2$C≡CH | H | Me | CF$_3$ | O |
| 2X.128 | H | CF$_2$C≡CH | H | Me | CF$_2$H | O |
| 2X.129 | H | CF$_2$C≡CH | F | Me | Me | O |
| 2X.130 | H | CHMeC≡CH | H | Me | CF$_3$ | O |
| 2X.131 | H | CHMeC≡CH | H | Me | CF$_2$H | O |
| 2X.132 | H | CHMeC≡CH | F | Me | Me | O |
| 2X.133 | H | CH(CF$_3$)C≡CH | H | Me | CF$_3$ | O |
| 2X.134 | H | CH(CF$_3$)C≡CH | H | Me | CF$_2$H | O |
| 2X.135 | H | CH(CF$_3$)C≡CH | F | Me | Me | O |
| 2X.136 | H | CMe$_2$C≡CH | H | Me | CF$_3$ | O |
| 2X.137 | H | CMe$_2$C≡CH | H | Me | CF$_2$H | O |
| 2X.138 | H | CMe$_2$C≡CH | F | Me | Me | O |
| 2X.139 | H | CH$_2$C≡CMe | H | Me | CF$_3$ | O |
| 2X.140 | H | CH$_2$C≡CMe | H | Me | CF$_2$H | O |
| 2X.141 | H | CH$_2$C≡CMe | F | Me | Me | O |
| 2X.142 | H | CF$_2$C≡CMe | H | Me | CF$_3$ | O |
| 2X.143 | H | CF$_2$C≡CMe | H | Me | CF$_2$H | O |
| 2X.144 | H | CF$_2$C≡CMe | F | Me | Me | O |
| 2X.145 | H | CH$_2$C≡CCF$_3$ | H | Me | CF$_3$ | O |
| 2X.146 | H | CH$_2$C≡CCF$_3$ | H | Me | CF$_2$H | O |
| 2X.147 | H | CH$_2$C≡CCF$_3$ | F | Me | Me | O |
| 2X.148 | H | CF$_2$C≡CCF$_3$ | H | Me | CF$_3$ | O |
| 2X.149 | H | CF$_2$C≡CCF$_3$ | H | Me | CF$_2$H | O |
| 2X.150 | H | CF$_2$C≡CCF$_3$ | F | Me | Me | O |
| 2X.151 | H | CH$_2$C≡CCMe$_3$ | H | Me | CF$_3$ | O |
| 2X.152 | H | CH$_2$C≡CCMe$_3$ | H | Me | CF$_2$H | O |
| 2X.153 | H | CH$_2$C≡CCMe$_3$ | F | Me | Me | O |
| 2X.154 | H | CF$_2$C≡CCMe$_3$ | H | Me | CF$_3$ | O |
| 2X.155 | H | CF$_2$C≡CCMe$_3$ | H | Me | CF$_2$H | O |
| 2X.156 | H | CF$_2$C≡CCMe$_3$ | F | Me | Me | O |
| 2X.157 | H | CH$_2$C≡CSiMe$_3$ | H | Me | CF$_3$ | O |
| 2X.158 | H | CH$_2$C≡CSiMe$_3$ | H | Me | CF$_2$H | O |
| 2X.159 | H | CH$_2$C≡CSiMe$_3$ | F | Me | Me | O |
| 2X.160 | H | CF$_2$C≡CSiMe$_3$ | H | Me | CF$_3$ | O |
| 2X.161 | H | CF$_2$C≡CSiMe$_3$ | H | Me | CF$_2$H | O |
| 2X.162 | H | CF$_2$C≡CSiMe$_3$ | F | Me | Me | O |
| 2X.163 | H | CH═CH$_2$ | H | Me | CF$_3$ | O |
| 2X.164 | H | CH═CH$_2$ | H | Me | CF$_2$H | O |
| 2X.165 | H | CH═CH$_2$ | F | Me | Me | O |
| 2X.166 | H | CH═CH$_2$ | H | Me | CF$_3$ | S |
| 2X.167 | H | CH═CH$_2$ | H | Me | CF$_2$H | S |
| 2X.168 | propargyl | CH═CH$_2$ | H | Me | CF$_3$ | O |
| 2X.169 | allenyl | CH═CH$_2$ | H | Me | CF$_3$ | O |
| 2X.170 | COMe | CH═CH$_2$ | H | Me | CF$_3$ | O |
| 2X.171 | H | CH═CHF | H | Me | CF$_3$ | O |
| 2X.172 | H | CH═CHF | H | Me | CF$_2$H | O |
| 2X.173 | H | CH═CHF | F | Me | Me | O |
| 2X.174 | H | CH═CHCl | H | Me | CF$_3$ | O |
| 2X.175 | H | CH═CHCl | H | Me | CF$_2$H | O |
| 2X.176 | H | CH═CHCl | F | Me | Me | O |
| 2X.177 | H | CH═CHBr | H | Me | CF$_3$ | O |
| 2X.178 | H | CH═CHBr | H | Me | CF$_2$H | O |
| 2X.179 | H | CH═CHBr | F | Me | Me | O |
| 2X.180 | H | CH═CF$_2$ | H | Me | CF$_3$ | O |
| 2X.181 | H | CH═CF$_2$ | H | Me | CF$_2$H | O |
| 2X.182 | H | CH═CF$_2$ | F | Me | Me | O |
| 2X.183 | H | CH═CFCl | H | Me | CF$_3$ | O |
| 2X.184 | H | CH═CFCl | H | Me | CF$_2$H | O |
| 2X.185 | H | CH═CFCl | F | Me | Me | O |
| 2X.186 | H | CH═CFBr | H | Me | CF$_3$ | O |
| 2X.187 | H | CH═CFBr | H | Me | CF$_2$H | O |
| 2X.188 | H | CH═CFBr | F | Me | Me | O |
| 2X.189 | H | CH═CCl$_2$ | H | Me | CF$_3$ | O |
| 2X.190 | H | CH═CCl$_2$ | H | Me | CF$_2$H | O |
| 2X.191 | H | CH═CCl$_2$ | F | Me | Me | O |
| 2X.192 | H | CH═CBr$_2$ | H | Me | CF$_3$ | O |
| 2X.193 | H | CH═CBr$_2$ | H | Me | CF$_2$H | O |
| 2X.194 | H | CH═CBr$_2$ | F | Me | Me | O |
| 2X.195 | H | CF═CH$_2$ | H | Me | CF$_3$ | O |
| 2X.196 | H | CF═CH$_2$ | H | Me | CF$_2$H | O |
| 2X.197 | H | CF═CH$_2$ | F | Me | Me | O |
| 2X.198 | H | CF═CHF | H | Me | CF$_3$ | O |
| 2X.199 | H | CF═CHF | H | Me | CF$_2$H | O |
| 2X.200 | H | CF═CHF | F | Me | Me | O |
| 2X.201 | H | CF═CF$_2$ | H | Me | CF$_3$ | O |
| 2X.202 | H | CF═CF$_2$ | H | Me | CF$_2$H | O |
| 2X.203 | H | CF═CF$_2$ | F | Me | Me | O |
| 2X.204 | H | CF═CFCl | H | Me | CF$_3$ | O |
| 2X.205 | H | CF═CFCl | H | Me | CF$_2$H | O |
| 2X.206 | H | CF═CFCl | F | Me | Me | O |
| 2X.207 | H | CF═CFBr | H | Me | CF$_3$ | O |
| 2X.208 | H | CF═CFBr | H | Me | CF$_2$H | O |
| 2X.209 | H | CF═CFBr | F | Me | Me | O |
| 2X.210 | H | CF═CCl$_2$ | H | Me | CF$_3$ | O |
| 2X.211 | H | CF═CCl$_2$ | H | Me | CF$_2$H | O |
| 2X.212 | H | CF═CCl$_2$ | F | Me | Me | O |
| 2X.213 | H | CCl═CH$_2$ | H | Me | CF$_3$ | O |
| 2X.214 | H | CCl═CH$_2$ | H | Me | CF$_2$H | O |
| 2X.215 | H | CCl═CH$_2$ | F | Me | Me | O |
| 2X.216 | H | CCl═CF$_2$ | H | Me | CF$_3$ | O |
| 2X.217 | H | CCl═CF$_2$ | H | Me | CF$_2$H | O |
| 2X.218 | H | CCl═CF$_2$ | F | Me | Me | O |
| 2X.219 | H | CBr═CH$_2$ | H | Me | CF$_3$ | O |
| 2X.220 | H | CBr═CH$_2$ | H | Me | CF$_2$H | O |
| 2X.221 | H | CBr═CH$_2$ | F | Me | Me | O |
| 2X.222 | H | CBr═CF$_2$ | H | Me | CF$_3$ | O |
| 2X.223 | H | CBr═CF$_2$ | H | Me | CF$_2$H | O |
| 2X.224 | H | CBr═CF$_2$ | F | Me | Me | O |
| 2X.225 | H | CH═CHCF$_3$ | H | Me | CF$_3$ | O |
| 2X.226 | H | CH═CHCF$_3$ | H | Me | CF$_2$H | O |
| 2X.227 | H | CH═CHCF$_3$ | F | Me | Me | O |
| 2X.228 | H | CH═CFCF$_3$ | H | Me | CF$_3$ | O |

TABLE 2X-continued

| Compound No. | $R^1$ | $R^6$ | $R^7$ | $R^8$ | $R^9$ | X |
|---|---|---|---|---|---|---|
| 2X.229 | H | $CH=CFCF_3$ | H | Me | $CF_2H$ | O |
| 2X.230 | H | $CH=CFCF_3$ | F | Me | Me | O |
| 2X.231 | H | $CH=CClCF_3$ | H | Me | $CF_3$ | O |
| 2X.232 | H | $CH=CClCF_3$ | H | Me | $CF_2H$ | O |
| 2X.233 | H | $CH=CClCF_3$ | F | Me | Me | O |
| 2X.234 | H | $CH=CBrCF_3$ | H | Me | $CF_3$ | O |
| 2X.235 | H | $CH=CBrCF_3$ | H | Me | $CF_2H$ | O |
| 2X.236 | H | $CH=CBrCF_3$ | F | Me | Me | O |
| 2X.237 | H | $CH=CFCF_2Cl$ | H | Me | $CF_3$ | O |
| 2X.238 | H | $CH=CFCF_2Cl$ | H | Me | $CF_2H$ | O |
| 2X.239 | H | $CH=CFCF_2Cl$ | F | Me | Me | O |
| 2X.240 | H | $CH=CClCF_2Cl$ | H | Me | $CF_3$ | O |
| 2X.241 | H | $CH=CClCF_2Cl$ | H | Me | $CF_2H$ | O |
| 2X.242 | H | $CH=CClCF_2Cl$ | F | Me | Me | O |
| 2X.243 | H | $CF=CHCF_3$ | H | Me | $CF_3$ | O |
| 2X.244 | H | $CF=CHCF_3$ | H | Me | $CF_2H$ | O |
| 2X.245 | H | $CF=CHCF_3$ | F | Me | Me | O |
| 2X.246 | H | $CF=CFCF_3$ | H | Me | $CF_3$ | O |
| 2X.247 | H | $CF=CFCF_3$ | H | Me | $CF_2H$ | O |
| 2X.248 | H | $CF=CFCF_3$ | F | Me | Me | O |
| 2X.249 | H | $CH=CHC_2F_5$ | H | Me | $CF_3$ | O |
| 2X.250 | H | $CH=CHC_2F_5$ | H | Me | $CF_2H$ | O |
| 2X.251 | H | $CH=CHC_2F_5$ | F | Me | Me | O |
| 2X.252 | H | $CH=CFC_2F_5$ | H | Me | $CF_3$ | O |
| 2X.253 | H | $CH=CFC_2F_5$ | H | Me | $CF_2H$ | O |
| 2X.254 | H | $CH=CFC_2F_5$ | F | Me | Me | O |
| 2X.255 | H | $CH=CClC_2F_5$ | H | Me | $CF_3$ | O |
| 2X.256 | H | $CH=CClC_2F_5$ | H | Me | $CF_2H$ | O |
| 2X.257 | H | $CH=CClC_2F_5$ | F | Me | Me | O |
| 2X.258 | H | $CH=C(CF_3)_2$ | H | Me | $CF_3$ | O |
| 2X.259 | H | $CH=C(CF_3)_2$ | H | Me | $CF_2H$ | O |
| 2X.260 | H | $CH=C(CF_3)_2$ | F | Me | Me | O |
| 2X.261 | H | $CF=C(CF_3)_2$ | H | Me | $CF_3$ | O |
| 2X.262 | H | $CF=C(CF_3)_2$ | H | Me | $CF_2H$ | O |
| 2X.263 | H | $CF=C(CF_3)_2$ | F | Me | Me | O |
| 2X.264 | H | $CH=CHSiMe_3$ | H | Me | $CF_3$ | O |
| 2X.265 | H | $CH=CHSiMe_3$ | H | Me | $CF_2H$ | O |
| 2X.266 | H | $CH=CHSiMe_3$ | F | Me | Me | O |
| 2X.267 | H | $CMe=CF_2$ | H | Me | $CF_3$ | O |
| 2X.268 | H | $CMe=CF_2$ | H | Me | $CF_2H$ | O |
| 2X.269 | H | $CMe=CF_2$ | F | Me | Me | O |
| 2X.270 | H | $CMe=CFCl$ | H | Me | $CF_3$ | O |
| 2X.271 | H | $CMe=CFCl$ | H | Me | $CF_2H$ | O |
| 2X.272 | H | $CMe=CFCl$ | F | Me | Me | O |
| 2X.273 | H | $CMe=CFBr$ | H | Me | $CF_3$ | O |
| 2X.274 | H | $CMe=CFBr$ | H | Me | $CF_2H$ | O |
| 2X.275 | H | $CMe=CFBr$ | F | Me | Me | O |
| 2X.276 | H | $CMe=CCl_2$ | H | Me | $CF_3$ | O |
| 2X.277 | H | $CMe=CCl_2$ | H | Me | $CF_2H$ | O |
| 2X.278 | H | $CMe=CCl_2$ | F | Me | Me | O |
| 2X.279 | H | $CMe=CBr_2$ | H | Me | $CF_3$ | O |
| 2X.280 | H | $CMe=CBr_2$ | H | Me | $CF_2H$ | O |
| 2X.281 | H | $CMe=CBr_2$ | F | Me | Me | O |
| 2X.282 | H | $CMe=CHCF_3$ | H | Me | $CF_3$ | O |
| 2X.283 | H | $CMe=CHCF_3$ | H | Me | $CF_2H$ | O |
| 2X.284 | H | $CMe=CHCF_3$ | F | Me | Me | O |
| 2X.285 | H | $CMe=CFCF_3$ | H | Me | $CF_3$ | O |
| 2X.286 | H | $CMe=CFCF_3$ | H | Me | $CF_2H$ | O |
| 2X.287 | H | $CMe=CFCF_3$ | F | Me | Me | O |
| 2X.288 | H | $CMe=CClCF_3$ | H | Me | $CF_3$ | O |
| 2X.289 | H | $CMe=CClCF_3$ | H | Me | $CF_2H$ | O |
| 2X.290 | H | $CMe=CClCF_3$ | F | Me | Me | O |
| 2X.291 | H | $CCF_3=CH_2$ | H | Me | $CF_3$ | O |
| 2X.292 | H | $CCF_3=CH_2$ | H | Me | $CF_2H$ | O |
| 2X.293 | H | $CCF_3=CH_2$ | F | Me | Me | O |
| 2X.294 | H | $CCF_3=CHF$ | H | Me | $CF_3$ | O |
| 2X.295 | H | $CCF_3=CHF$ | H | Me | $CF_2H$ | O |
| 2X.296 | H | $CCF_3=CHF$ | F | Me | Me | O |
| 2X.297 | H | $CCF_3=CHCl$ | H | Me | $CF_3$ | O |
| 2X.298 | H | $CCF_3=CHCl$ | H | Me | $CF_2H$ | O |
| 2X.299 | H | $CCF_3=CHCl$ | F | Me | Me | O |
| 2X.300 | H | $CCF_3=CF_2$ | H | Me | $CF_3$ | O |
| 2X.301 | H | $CCF_3=CF_2$ | H | Me | $CF_2H$ | O |
| 2X.302 | H | $CCF_3=CF_2$ | F | Me | Me | O |
| 2X.303 | H | $CCF_3=CCl_2$ | H | Me | $CF_3$ | O |
| 2X.304 | H | $CCF_3=CCl_2$ | H | Me | $CF_2H$ | O |
| 2X.305 | H | $CCF_3=CCl_2$ | F | Me | Me | O |
| 2X.306 | H | $CCF_3=CBr_2$ | H | Me | $CF_3$ | O |
| 2X.307 | H | $CCF_3=CBr_2$ | H | Me | $CF_2H$ | O |
| 2X.308 | H | $CCF_3=CBr_2$ | F | Me | Me | O |
| 2X.309 | H | $CH_2CH=CF_2$ | H | Me | $CF_3$ | O |
| 2X.310 | H | $CH_2CH=CF_2$ | H | Me | $CF_2H$ | O |
| 2X.311 | H | $CH_2CH=CF_2$ | F | Me | Me | O |
| 2X.312 | H | $CH_2CH=CCl_2$ | H | Me | $CF_3$ | O |
| 2X.313 | H | $CH_2CH=CCl_2$ | H | Me | $CF_2H$ | O |
| 2X.314 | H | $CH_2CH=CCl_2$ | F | Me | Me | O |
| 2X.315 | H | $CH_2CF=CF_2$ | H | Me | $CF_3$ | O |
| 2X.316 | H | $CH_2CF=CF_2$ | H | Me | $CF_2H$ | O |
| 2X.317 | H | $CH_2CF=CF_2$ | F | Me | Me | O |
| 2X.318 | H | $CH_2CF=CCl_2$ | H | Me | $CF_3$ | O |
| 2X.319 | H | $CH_2CF=CCl_2$ | H | Me | $CF_2H$ | O |
| 2X.320 | H | $CH_2CF=CCl_2$ | F | Me | Me | O |

Table 2ba provides 320 compounds of formula (I.ba):

(I.ba)

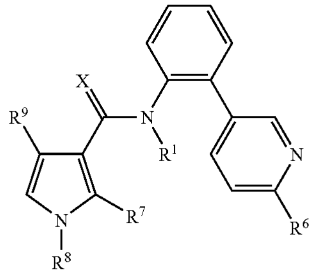

wherein $R^1$, $R^6$, $R^7$, $R^8$, $R^9$ and X are as defined in Table 2ba.

Table 2bb provides 320 compounds of formula (I.bb):

(I.bb)

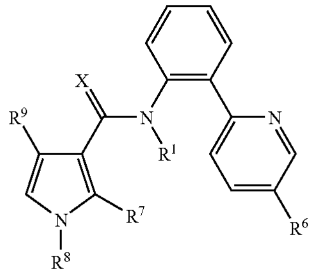

wherein $R^1$, $R^6$, $R^7$, $R^8$, $R^9$ and X are as defined in Table 2bb.

Table 2bc provides 320 compounds of formula (I.bc)

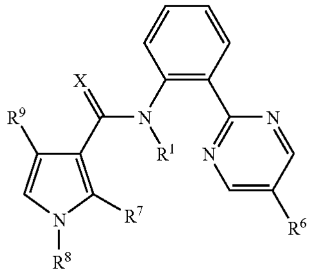

(I.bc)

wherein $R^1$, $R^6$, $R^7$, $R^8$, $R^9$ and X are as defined in Table 2bc.

Table 2bd provides 320 compounds of formula (I.bd)

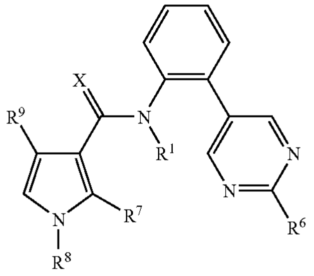

(I.bd)

wherein $R^1$, $R^6$, $R^7$, $R^8$, $R^9$ and X are as defined in Table 2bd.

Table 2be provides 320 compounds of formula (I.be)

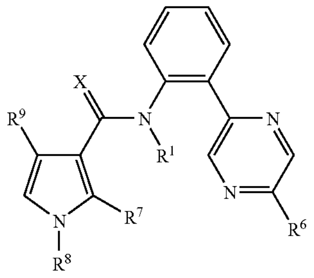

(I.be)

wherein $R^1$, $R^6$, $R^7$, $R^8$, $R^9$ and X are as defined in Table 2be.

Table 2bf provides 320 compounds of formula (I.bf)

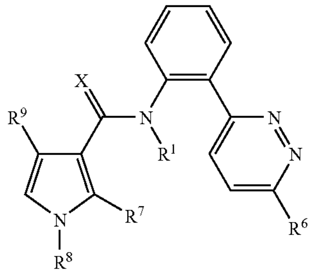

(I.bf)

wherein $R^1$, $R^6$, $R^7$, $R^8$, $R^9$ and X are as defined in Table 2bf.

Table 2bg provides 320 compounds of formula (I.bg)

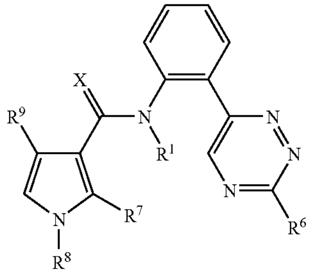

(I.bg)

wherein $R^1$, $R^6$, $R^7$, $R^8$, $R^9$ and X are as defined in Table 2bg.

Table 2bh provides 320 compounds of formula (I.bh)

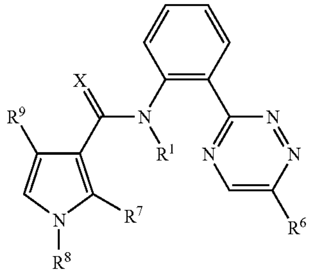

(I.bh)

wherein $R^1$, $R^6$, $R^7$, $R^8$, $R^9$ and X are as defined in Table 2bh.

Table 2bi provides 320 compounds of formula (I.bi)

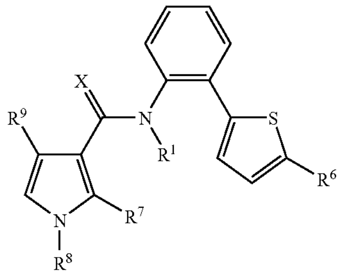

(I.bi)

wherein $R^1$, $R^6$, $R^7$, $R^8$, $R^9$ and X are as defined in Table 2bi.

Table 2bj provides 320 compounds of formula (I.bj)

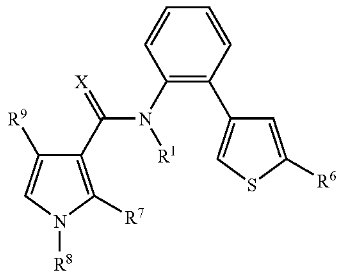

(I.bj)

wherein $R^1$, $R^6$, $R^7$, $R^8$, $R^9$ and X are as defined in Table 2bj.

Table 2bk provides 320 compounds of formula (I.bk)

(I.bk)

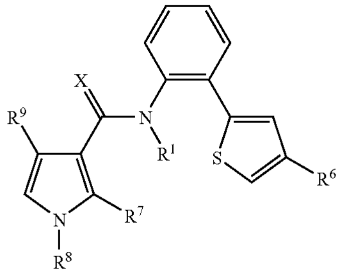

wherein $R^1$, $R^6$, $R^7$, $R^8$, $R^9$ and X are as defined in Table 2bk.

Table 2bl provides 320 compounds of formula (I.bl)

(I.bl)

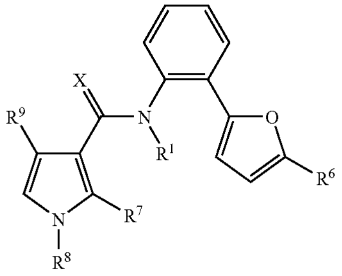

wherein $R^1$, $R^6$, $R^7$, $R^8$, $R^9$ and X are as defined in Table 2bl.

Table 2bm provides 320 compounds of formula (I.bm)

(I.bm)

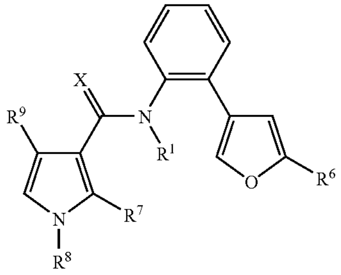

wherein $R^1$, $R^6$, $R^7$, $R^8$, $R^9$ and X are as defined in Table 2bm.

Table 2bn provides 320 compounds of formula (I.bn)

(I.bn)

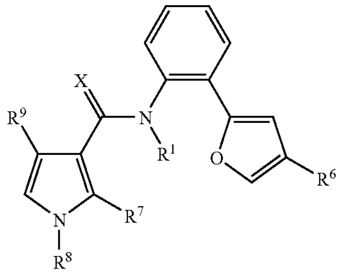

wherein $R^1$, $R^6$, $R^7$, $R^8$, $R^9$ and X are as defined in Table 2bn.

Table 2bo provides 320 compounds of formula (I.bo)

(I.bo)

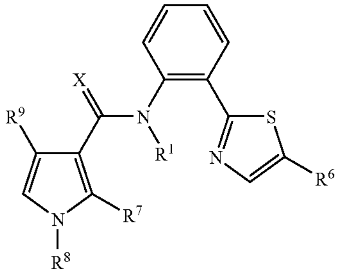

wherein $R^1$, $R^6$, $R^7$, $R^8$, $R^9$ and X are as defined in Table 2bo.

Table 2 bp provides 320 compounds of formula (I.bp)

(I.bp)

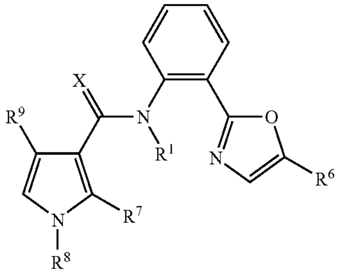

wherein $R^1$, $R^6$, $R^7$, $R^8$, $R^9$ and X are as defined in Table 2 bp.

Table 2bq provides 320 compounds of formula (I.bq)

(I.bq)

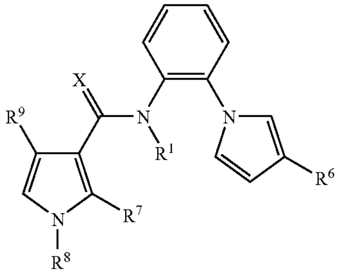

wherein $R^1$, $R^6$, $R^7$, $R^8$, $R^9$ and X are as defined in Table 2bq.

Table 2br provides 320 compounds of formula (I.br)

(I.br)

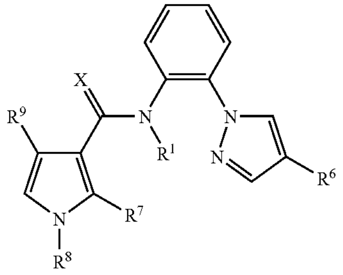

wherein $R^1$, $R^6$, $R^7$, $R^8$, $R^9$ and X are as defined in Table 2br.

Table 2bs provides 320 compounds of formula (I.bs)

(I.bs)

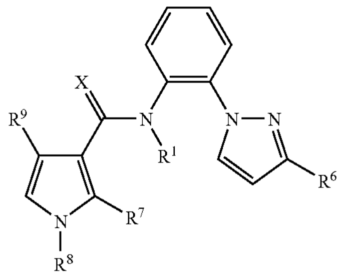

wherein $R^1$, $R^6$, $R^7$, $R^8$, $R^9$ and X are as defined in Table 2bs.

Table 2bt provides 320 compounds of formula (I.bt)

(I.bt)

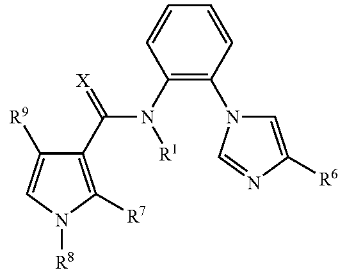

wherein $R^1$, $R^6$, $R^7$, $R^8$, $R^9$ and X are as defined in Table 2bt.

Table 2bu provides 320 compounds of formula (I.bu)

(I.bu)

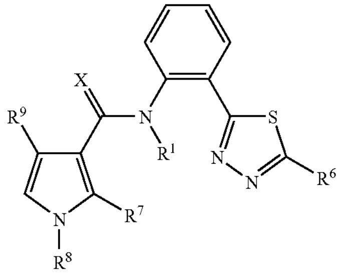

wherein $R^1$, $R^6$, $R^7$, $R^8$, $R^9$ and X are as defined in Table 2bu.

Table 2by provides 320 compounds of formula (I.bv)

(I.bv)

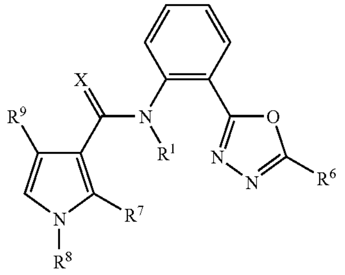

wherein $R^1$, $R^6$, $R^7$, $R^8$, $R^9$ and X are as defined in Table 2bv.

Table 2bw provides 320 compounds of formula (I.bw)

(I.bw)

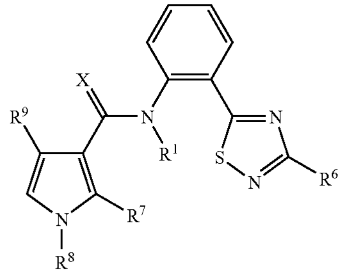

wherein $R^1$, $R^6$, $R^7$, $R^8$, $R^9$ and X are as defined in Table 2bw.

Table 2bx provides 320 compounds of formula (I.bx)

(I.bx)

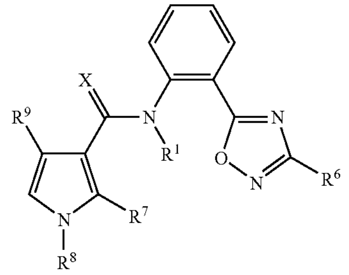

wherein $R^1$, $R^6$, $R^7$, $R^8$, $R^9$ and X are as defined in Table 2bx.

Table 3X represents Table 3ca (when X is ca), represents Table 3cb (when X is cb), represents Table 3cc (when X is cc), represents Table 3cd (when X is cd), represents Table 3ce (when X is ce), represents Table 3cf (when X is cf), represents Table 3cg (when X is cg), represents Table 3ch (when X is ch), represents Table 3ci (when X is ci), represents Table 3cj (when X is cj), represents Table 3ck (when X is ck), represents Table 3cl (when X is cl), represents Table 3cm (when X is cm), represents Table 3cn (when X is cn), represents Table 3co (when X is co), represents Table 3cp (when X is cp), represents Table 3cq (when X is cq), represents Table 3cr (when X is cr), represents Table 3cs (when X is cs), represents Table 3ct (when X is ct), represents Table 3cu (when X is cu), represents Table 3cv (when X is cv), represents Table 3cw (when X is cw) and represents Table 3cx (when X is cx).

TABLE 3

| Compound No. | $R^1$ | $R^6$ | $R^8$ | $R^9$ | X |
|---|---|---|---|---|---|
| 3X.001 | H | C≡CH | Me | $CF_3$ | O |
| 3X.002 | H | C≡CH | Me | $CF_2H$ | O |
| 3X.003 | H | C≡CH | Me | Me | O |
| 3X.004 | H | C≡CH | Me | $CF_3$ | S |
| 3X.005 | H | C≡CH | Me | $CF_2H$ | S |
| 3X.006 | propargyl | C≡CH | Me | $CF_3$ | O |
| 3X.007 | allenyl | C≡CH | Me | $CF_3$ | O |
| 3X.008 | COMe | C≡CH | Me | $CF_3$ | O |
| 3X.009 | H | C≡CF | Me | $CF_3$ | O |
| 3X.010 | H | C≡CF | Me | $CF_2H$ | O |
| 3X.011 | H | C≡CF | Me | Me | O |
| 3X.012 | H | C≡CCl | Me | $CF_3$ | O |
| 3X.013 | H | C≡CCl | Me | $CF_2H$ | O |
| 3X.014 | H | C≡CCl | Me | Me | O |

TABLE 3-continued

| Compound No. | R$^1$ | R$^6$ | R$^8$ | R$^9$ | X |
|---|---|---|---|---|---|
| 3X.015 | H | C≡CBr | Me | CF$_3$ | O |
| 3X.016 | H | C≡CBr | Me | CF$_2$H | O |
| 3X.017 | H | C≡CBr | Me | Me | O |
| 3X.018 | H | C≡CMe | Me | CF$_3$ | O |
| 3X.019 | H | C≡CMe | Me | CF$_2$H | O |
| 3X.020 | H | C≡CMe | Me | Me | O |
| 3X.021 | H | C≡CCH$_2$OMe | Me | CF$_3$ | O |
| 3X.022 | H | C≡CCH$_2$OMe | Me | CF$_2$H | O |
| 3X.023 | H | C≡CCH$_2$OMe | Me | Me | O |
| 3X.024 | H | C≡CCH$_2$F | Me | CF$_3$ | O |
| 3X.025 | H | C≡CCH$_2$F | Me | CF$_2$H | O |
| 3X.026 | H | C≡CCH$_2$F | Me | Me | O |
| 3X.027 | H | C≡CCF$_2$H | Me | CF$_3$ | O |
| 3X.028 | H | C≡CCF$_2$H | Me | CF$_2$H | O |
| 3X.029 | H | C≡CCF$_2$H | Me | Me | O |
| 3X.030 | H | C≡CCHFCl | Me | CF$_3$ | O |
| 3X.031 | H | C≡CCHFCl | Me | CF$_2$H | O |
| 3X.032 | H | C≡CCHFCl | Me | Me | O |
| 3X.033 | H | C≡CCF$_2$Cl | Me | CF$_3$ | O |
| 3X.034 | H | C≡CCF$_2$Cl | Me | CF$_2$H | O |
| 3X.035 | H | C≡CCF$_2$Cl | Me | Me | O |
| 3X.036 | H | C≡CCF$_2$Br | Me | CF$_3$ | O |
| 3X.037 | H | C≡CCF$_2$Br | Me | CF$_2$H | O |
| 3X.038 | H | C≡CCF$_2$Br | Me | Me | O |
| 3X.039 | H | C≡CCF$_3$ | Me | CF$_3$ | O |
| 3X.040 | H | C≡CCF$_3$ | Me | CF$_2$H | O |
| 3X.041 | H | C≡CCF$_3$ | Me | Me | O |
| 3X.042 | H | C≡CCF$_3$ | Me | CF$_3$ | S |
| 3X.043 | H | C≡CCF$_3$ | Me | CF$_2$H | S |
| 3X.044 | propargyl | C≡CCF$_3$ | Me | CF$_3$ | O |
| 3X.045 | allenyl | C≡CCF$_3$ | Me | CF$_3$ | O |
| 3X.046 | COMe | C≡CCF$_3$ | Me | CF$_3$ | O |
| 3X.047 | H | C≡CCH$_2$CH$_3$ | Me | CF$_3$ | O |
| 3X.048 | H | C≡CCH$_2$CH$_3$ | Me | CF$_2$H | O |
| 3X.049 | H | C≡CCH$_2$CH$_3$ | Me | Me | O |
| 3X.050 | H | C≡CCH(Me)F | Me | CF$_3$ | O |
| 3X.051 | H | C≡CCH(Me)F | Me | CF$_2$H | O |
| 3X.052 | H | C≡CCH(Me)F | Me | Me | O |
| 3X.053 | H | C≡CCF$_2$Me | Me | CF$_3$ | O |
| 3X.054 | H | C≡CCF$_2$Me | Me | CF$_2$H | O |
| 3X.055 | H | C≡CCF$_2$Me | Me | Me | O |
| 3X.056 | H | C≡CCH$_2$CF$_3$ | Me | CF$_3$ | O |
| 3X.057 | H | C≡CCH$_2$CF$_3$ | Me | CF$_2$H | O |
| 3X.058 | H | C≡CCH$_2$CF$_3$ | Me | Me | O |
| 3X.059 | H | C≡CC$_2$F$_5$ | Me | CF$_3$ | O |
| 3X.060 | H | C≡CC$_2$F$_5$ | Me | CF$_2$H | O |
| 3X.061 | H | C≡CC$_2$F$_5$ | Me | Me | O |
| 3X.062 | H | C≡CCF═CF$_2$ | Me | CF$_3$ | O |
| 3X.063 | H | C≡CCF═CF$_2$ | Me | CF$_2$H | O |
| 3X.064 | H | C≡CCF═CF$_2$ | Me | Me | O |
| 3X.065 | H | C≡CCH$_2$CH$_2$CH$_3$ | Me | CF$_3$ | O |
| 3X.066 | H | C≡CCH$_2$CH$_2$CH$_3$ | Me | CF$_2$H | O |
| 3X.067 | H | C≡CCH$_2$CH$_2$CH$_3$ | Me | Me | O |
| 3X.068 | H | C≡CCHFCH$_2$CH$_3$ | Me | CF$_3$ | O |
| 3X.069 | H | C≡CCHFCH$_2$CH$_3$ | Me | CF$_2$H | O |
| 3X.070 | H | C≡CCHFCH$_2$CH$_3$ | Me | Me | O |
| 3X.071 | H | C≡CCF$_2$CH$_2$CH$_3$ | Me | CF$_3$ | O |
| 3X.072 | H | C≡CCF$_2$CH$_2$CH$_3$ | Me | CF$_2$H | O |
| 3X.073 | H | C≡CCF$_2$CH$_2$CH$_3$ | Me | Me | O |
| 3X.074 | H | C≡CCH(Me)$_2$ | Me | CF$_3$ | O |
| 3X.075 | H | C≡CCH(Me)$_2$ | Me | CF$_2$H | O |
| 3X.076 | H | C≡CCH(Me)$_2$ | Me | Me | O |
| 3X.077 | H | C≡CCMe$_2$OMe | Me | CF$_3$ | O |
| 3X.078 | H | C≡CCMe$_2$OMe | Me | CF$_2$H | O |
| 3X.079 | H | C≡CCMe$_2$OMe | Me | Me | O |
| 3X.080 | H | C≡CC(Me)$_2$F | Me | CF$_3$ | O |
| 3X.081 | H | C≡CC(Me)$_2$F | Me | CF$_2$H | O |
| 3X.082 | H | C≡CC(Me)$_2$F | Me | Me | O |
| 3X.083 | H | C≡CCF(CF$_3$)$_2$ | Me | CF$_3$ | O |
| 3X.084 | H | C≡CCF(CF$_3$)$_2$ | Me | CF$_2$H | O |
| 3X.085 | H | C≡CCF(CF$_3$)$_2$ | Me | Me | O |
| 3X.086 | H | C≡CC(Me)═CH$_2$ | Me | CF$_3$ | O |
| 3X.087 | H | C≡CC(Me)═CH$_2$ | Me | CF$_2$H | O |
| 3X.088 | H | C≡CC(Me)═CH$_2$ | Me | Me | O |
| 3X.089 | H | C≡C(cyclopropyl) | Me | CF$_3$ | O |
| 3X.090 | H | C≡C(cyclopropyl) | Me | CHF$_2$ | O |
| 3X.091 | H | C≡C(cyclopropyl) | Me | Me | O |
| 3X.092 | H | C≡CCH$_2$CH(Me)$_2$ | Me | CF$_3$ | O |
| 3X.093 | H | C≡CCH$_2$CH(Me)$_2$ | Me | CF$_2$H | O |
| 3X.094 | H | C≡CCH$_2$CH(Me)$_2$ | Me | Me | O |
| 3X.095 | H | C≡CCH(Me)CH$_2$CH$_3$ | Me | CF$_3$ | O |
| 3X.096 | H | C≡CCH(Me)CH$_2$CH$_3$ | Me | CF$_2$H | O |
| 3X.097 | H | C≡CCH(Me)CH$_2$CH$_3$ | Me | Me | O |
| 3X.098 | H | C≡CCMe$_3$ | Me | CF$_3$ | O |
| 3X.099 | H | C≡CCMe$_3$ | Me | CF$_2$H | O |
| 3X.100 | H | C≡CCMe$_3$ | Me | Me | O |
| 3X.101 | H | C≡CCMe$_3$ | Me | CF$_3$ | S |
| 3X.102 | H | C≡CCMe$_3$ | Me | CF$_2$H | S |
| 3X.103 | propargyl | C≡CCMe$_3$ | Me | CF$_3$ | O |
| 3X.104 | allenyl | C≡CCMe$_3$ | Me | CF$_3$ | O |
| 3X.105 | COMe | C≡CCMe$_3$ | Me | CF$_3$ | O |
| 3X.106 | H | C≡CSiMe$_3$ | Me | CF$_3$ | O |
| 3X.107 | H | C≡CSiMe$_3$ | Me | CF$_2$H | O |
| 3X.108 | H | C≡CSiMe$_3$ | Me | Me | O |
| 3X.109 | H | C≡CCH$_2$C(Me)$_3$ | Me | CF$_3$ | O |
| 3X.110 | H | C≡CCH$_2$C(Me)$_3$ | Me | CF$_2$H | O |
| 3X.111 | H | C≡CCH$_2$C(Me)$_3$ | Me | Me | O |
| 3X.112 | H | C≡CCH$_2$SiMe$_3$ | Me | CF$_3$ | O |
| 3X.113 | H | C≡CCH$_2$SiMe$_3$ | Me | CF$_2$H | O |
| 3X.114 | H | C≡CCH$_2$SiMe$_3$ | Me | Me | O |
| 3X.115 | H | C≡C(1-F-cyclopentyl) | Me | CF$_3$ | O |
| 3X.116 | H | C≡C(1-F-cyclopentyl) | Me | CHF$_2$ | O |
| 3X.117 | H | C≡C(1-F-cyclopentyl) | Me | Me | O |
| 3X.118 | H | C≡CSi(Me$_2$)CMe$_3$ | Me | CF$_3$ | O |
| 3X.119 | H | C≡CSi(Me$_2$)CMe$_3$ | Me | CF$_2$H | O |
| 3X.120 | H | C≡CSi(Me$_2$)CMe$_3$ | Me | Me | O |
| 3X.121 | H | CH$_2$C≡CH | Me | CF$_3$ | O |
| 3X.122 | H | CH$_2$C≡CH | Me | CF$_2$H | O |
| 3X.123 | H | CH$_2$C≡CH | Me | Me | O |
| 3X.124 | H | CHFC≡CH | Me | CF$_3$ | O |
| 3X.125 | H | CHFC≡CH | Me | CF$_2$H | O |
| 3X.126 | H | CHFC≡CH | Me | Me | O |
| 3X.127 | H | CF$_2$C≡CH | Me | CF$_3$ | O |
| 3X.128 | H | CF$_2$C≡CH | Me | CF$_2$H | O |
| 3X.129 | H | CF$_2$C≡CH | Me | Me | O |
| 3X.130 | H | CHMeC≡CH | Me | CF$_3$ | O |
| 3X.131 | H | CHMeC≡CH | Me | CF$_2$H | O |
| 3X.132 | H | CHMeC≡CH | Me | Me | O |
| 3X.133 | H | CH(CF$_3$)C≡CH | Me | CF$_3$ | O |
| 3X.134 | H | CH(CF$_3$)C≡CH | Me | CF$_2$H | O |
| 3X.135 | H | CH(CF$_3$)C≡CH | Me | Me | O |
| 3X.136 | H | CMe$_2$C≡CH | Me | CF$_3$ | O |
| 3X.137 | H | CMe$_2$C≡CH | Me | CF$_2$H | O |
| 3X.138 | H | CMe$_2$C≡CH | Me | Me | O |
| 3X.139 | H | CH$_2$C≡CMe | Me | CF$_3$ | O |
| 3X.140 | H | CH$_2$C≡CMe | Me | CF$_2$H | O |
| 3X.141 | H | CH$_2$C≡CMe | Me | Me | O |
| 3X.142 | H | CF$_2$C≡CMe | Me | CF$_3$ | O |
| 3X.143 | H | CF$_2$C≡CMe | Me | CF$_2$H | O |
| 3X.144 | H | CF$_2$C≡CMe | Me | Me | O |
| 3X.145 | H | CH$_2$C≡CCF$_3$ | Me | CF$_3$ | O |
| 3X.146 | H | CH$_2$C≡CCF$_3$ | Me | CF$_2$H | O |
| 3X.147 | H | CH$_2$C≡CCF$_3$ | Me | Me | O |
| 3X.148 | H | CF$_2$C≡CCF$_3$ | Me | CF$_3$ | O |
| 3X.149 | H | CF$_2$C≡CCF$_3$ | Me | CF$_2$H | O |
| 3X.150 | H | CF$_2$C≡CCF$_3$ | Me | Me | O |
| 3X.151 | H | CH$_2$C≡CCMe$_3$ | Me | CF$_3$ | O |
| 3X.152 | H | CH$_2$C≡CCMe$_3$ | Me | CF$_2$H | O |
| 3X.153 | H | CH$_2$C≡CCMe$_3$ | Me | Me | O |
| 3X.154 | H | CF$_2$C≡CCMe$_3$ | Me | CF$_3$ | O |
| 3X.155 | H | CF$_2$C≡CCMe$_3$ | Me | CF$_2$H | O |
| 3X.156 | H | CF$_2$C≡CCMe$_3$ | Me | Me | O |
| 3X.157 | H | CH$_2$C≡CSiMe$_3$ | Me | CF$_3$ | O |
| 3X.158 | H | CH$_2$C≡CSiMe$_3$ | Me | CF$_2$H | O |
| 3X.159 | H | CH$_2$C≡CSiMe$_3$ | Me | Me | O |
| 3X.160 | H | CF$_2$C≡CSiMe$_3$ | Me | CF$_3$ | O |
| 3X.161 | H | CF$_2$C≡CSiMe$_3$ | Me | CF$_2$H | O |
| 3X.162 | H | CF$_2$C≡CSiMe$_3$ | Me | Me | O |
| 3X.163 | H | CH═CH$_2$ | Me | CF$_3$ | O |
| 3X.164 | H | CH═CH$_2$ | Me | CF$_2$H | O |
| 3X.165 | H | CH═CH$_2$ | Me | Me | O |
| 3X.166 | H | CH═CH$_2$ | Me | CF$_3$ | S |

TABLE 3-continued

| Compound No. | $R^1$ | $R^6$ | $R^8$ | $R^9$ | X |
|---|---|---|---|---|---|
| 3X.167 | H | $CH=CH_2$ | Me | $CF_2H$ | S |
| 3X.168 | propargyl | $CH=CH_2$ | Me | $CF_3$ | O |
| 3X.169 | allenyl | $CH=CH_2$ | Me | $CF_3$ | O |
| 3X.170 | COMe | $CH=CH_2$ | Me | $CF_3$ | O |
| 3X.171 | H | $CH=CHF$ | Me | $CF_3$ | O |
| 3X.172 | H | $CH=CHF$ | Me | $CF_2H$ | O |
| 3X.173 | H | $CH=CHF$ | Me | Me | O |
| 3X.174 | H | $CH=CHCl$ | Me | $CF_3$ | O |
| 3X.175 | H | $CH=CHCl$ | Me | $CF_2H$ | O |
| 3X.176 | H | $CH=CHCl$ | Me | Me | O |
| 3X.177 | H | $CH=CHBr$ | Me | $CF_3$ | O |
| 3X.178 | H | $CH=CHBr$ | Me | $CF_2H$ | O |
| 3X.179 | H | $CH=CHBr$ | Me | Me | O |
| 3X.180 | H | $CH=CF_2$ | Me | $CF_3$ | O |
| 3X.181 | H | $CH=CF_2$ | Me | $CF_2H$ | O |
| 3X.182 | H | $CH=CF_2$ | Me | Me | O |
| 3X.183 | H | $CH=CFCl$ | Me | $CF_3$ | O |
| 3X.184 | H | $CH=CFCl$ | Me | $CF_2H$ | O |
| 3X.185 | H | $CH=CFCl$ | Me | Me | O |
| 3X.186 | H | $CH=CFBr$ | Me | $CF_3$ | O |
| 3X.187 | H | $CH=CFBr$ | Me | $CF_2H$ | O |
| 3X.188 | H | $CH=CFBr$ | Me | Me | O |
| 3X.189 | H | $CH=CCl_2$ | Me | $CF_3$ | O |
| 3X.190 | H | $CH=CCl_2$ | Me | $CF_2H$ | O |
| 3X.191 | H | $CH=CCl_2$ | Me | Me | O |
| 3X.192 | H | $CH=CBr_2$ | Me | $CF_3$ | O |
| 3X.193 | H | $CH=CBr_2$ | Me | $CF_2H$ | O |
| 3X.194 | H | $CH=CBr_2$ | Me | Me | O |
| 3X.195 | H | $CF=CH_2$ | Me | $CF_3$ | O |
| 3X.196 | H | $CF=CH_2$ | Me | $CF_2H$ | O |
| 3X.197 | H | $CF=CH_2$ | Me | Me | O |
| 3X.198 | H | $CF=CHF$ | Me | $CF_3$ | O |
| 3X.199 | H | $CF=CHF$ | Me | $CF_2H$ | O |
| 3X.200 | H | $CF=CHF$ | Me | Me | O |
| 3X.201 | H | $CF=CF_2$ | Me | $CF_3$ | O |
| 3X.202 | H | $CF=CF_2$ | Me | $CF_2H$ | O |
| 3X.203 | H | $CF=CF_2$ | Me | Me | O |
| 3X.204 | H | $CF=CFCl$ | Me | $CF_3$ | O |
| 3X.205 | H | $CF=CFCl$ | Me | $CF_2H$ | O |
| 3X.206 | H | $CF=CFCl$ | Me | Me | O |
| 3X.207 | H | $CF=CFBr$ | Me | $CF_3$ | O |
| 3X.208 | H | $CF=CFBr$ | Me | $CF_2H$ | O |
| 3X.209 | H | $CF=CFBr$ | Me | Me | O |
| 3X.210 | H | $CF=CCl_2$ | Me | $CF_3$ | O |
| 3X.211 | H | $CF=CCl_2$ | Me | $CF_2H$ | O |
| 3X.212 | H | $CF=CCl_2$ | Me | Me | O |
| 3X.213 | H | $CCl=CH_2$ | Me | $CF_3$ | O |
| 3X.214 | H | $CCl=CH_2$ | Me | $CF_2H$ | O |
| 3X.215 | H | $CCl=CH_2$ | Me | Me | O |
| 3X.216 | H | $CCl=CF_2$ | Me | $CF_3$ | O |
| 3X.217 | H | $CCl=CF_2$ | Me | $CF_2H$ | O |
| 3X.218 | H | $CCl=CF_2$ | Me | Me | O |
| 3X.219 | H | $CBr=CH_2$ | Me | $CF_3$ | O |
| 3X.220 | H | $CBr=CH_2$ | Me | $CF_2H$ | O |
| 3X.221 | H | $CBr=CH_2$ | Me | Me | O |
| 3X.222 | H | $CBr=CF_2$ | Me | $CF_3$ | O |
| 3X.223 | H | $CBr=CF_2$ | Me | $CF_2H$ | O |
| 3X.224 | H | $CBr=CF_2$ | Me | Me | O |
| 3X.225 | H | $CH=CHCF_3$ | Me | $CF_3$ | O |
| 3X.226 | H | $CH=CHCF_3$ | Me | $CF_2H$ | O |
| 3X.227 | H | $CH=CHCF_3$ | Me | Me | O |
| 3X.228 | H | $CH=CFCF_3$ | Me | $CF_3$ | O |
| 3X.229 | H | $CH=CFCF_3$ | Me | $CF_2H$ | O |
| 3X.230 | H | $CH=CFCF_3$ | Me | Me | O |
| 3X.231 | H | $CH=CClCF_3$ | Me | $CF_3$ | O |
| 3X.232 | H | $CH=CClCF_3$ | Me | $CF_2H$ | O |
| 3X.233 | H | $CH=CClCF_3$ | Me | Me | O |
| 3X.234 | H | $CH=CBrCF_3$ | Me | $CF_3$ | O |
| 3X.235 | H | $CH=CBrCF_3$ | Me | $CF_2H$ | O |
| 3X.236 | H | $CH=CBrCF_3$ | Me | Me | O |
| 3X.237 | H | $CH=CFCF_2Cl$ | Me | $CF_3$ | O |
| 3X.238 | H | $CH=CFCF_2Cl$ | Me | $CF_2H$ | O |
| 3X.239 | H | $CH=CFCF_2Cl$ | Me | Me | O |
| 3X.240 | H | $CH=CClCF_2Cl$ | Me | $CF_3$ | O |
| 3X.241 | H | $CH=CClCF_2Cl$ | Me | $CF_2H$ | O |
| 3X.242 | H | $CH=CClCF_2Cl$ | Me | Me | O |
| 3X.243 | H | $CF=CHCF_3$ | Me | $CF_3$ | O |
| 3X.244 | H | $CF=CHCF_3$ | Me | $CF_2H$ | O |
| 3X.245 | H | $CF=CHCF_3$ | Me | Me | O |
| 3X.246 | H | $CF=CFCF_3$ | Me | $CF_3$ | O |
| 3X.247 | H | $CF=CFCF_3$ | Me | $CF_2H$ | O |
| 3X.248 | H | $CF=CFCF_3$ | Me | Me | O |
| 3X.249 | H | $CH=CHC_2F_5$ | Me | $CF_3$ | O |
| 3X.250 | H | $CH=CHC_2F_5$ | Me | $CF_2H$ | O |
| 3X.251 | H | $CH=CHC_2F_5$ | Me | Me | O |
| 3X.252 | H | $CH=CFC_2F_5$ | Me | $CF_3$ | O |
| 3X.253 | H | $CH=CFC_2F_5$ | Me | $CF_2H$ | O |
| 3X.254 | H | $CH=CFC_2F_5$ | Me | Me | O |
| 3X.255 | H | $CH=CClC_2F_5$ | Me | $CF_3$ | O |
| 3X.256 | H | $CH=CClC_2F_5$ | Me | $CF_2H$ | O |
| 3X.257 | H | $CH=CClC_2F_5$ | Me | Me | O |
| 3X.258 | H | $CH=C(CF_3)_2$ | Me | $CF_3$ | O |
| 3X.259 | H | $CH=C(CF_3)_2$ | Me | $CF_2H$ | O |
| 3X.260 | H | $CH=C(CF_3)_2$ | Me | Me | O |
| 3X.261 | H | $CF=C(CF_3)_2$ | Me | $CF_3$ | O |
| 3X.262 | H | $CF=C(CF_3)_2$ | Me | $CF_2H$ | O |
| 3X.263 | H | $CF=C(CF_3)_2$ | Me | Me | O |
| 3X.264 | H | $CH=CHSiMe_3$ | Me | $CF_3$ | O |
| 3X.265 | H | $CH=CHSiMe_3$ | Me | $CF_2H$ | O |
| 3X.266 | H | $CH=CHSiMe_3$ | Me | Me | O |
| 3X.267 | H | $CMe=CF_2$ | Me | $CF_3$ | O |
| 3X.268 | H | $CMe=CF_2$ | Me | $CF_2H$ | O |
| 3X.269 | H | $CMe=CF_2$ | Me | Me | O |
| 3X.270 | H | $CMe=CFCl$ | Me | $CF_3$ | O |
| 3X.271 | H | $CMe=CFCl$ | Me | $CF_2H$ | O |
| 3X.272 | H | $CMe=CFCl$ | Me | Me | O |
| 3X.273 | H | $CMe=CFBr$ | Me | $CF_3$ | O |
| 3X.274 | H | $CMe=CFBr$ | Me | $CF_2H$ | O |
| 3X.275 | H | $CMe=CFBr$ | Me | Me | O |
| 3X.276 | H | $CMe=CCl_2$ | Me | $CF_3$ | O |
| 3X.277 | H | $CMe=CCl_2$ | Me | $CF_2H$ | O |
| 3X.278 | H | $CMe=CCl_2$ | Me | Me | O |
| 3X.279 | H | $CMe=CBr_2$ | Me | $CF_3$ | O |
| 3X.280 | H | $CMe=CBr_2$ | Me | $CF_2H$ | O |
| 3X.281 | H | $CMe=CBr_2$ | Me | Me | O |
| 3X.282 | H | $CMe=CHCF_3$ | Me | $CF_3$ | O |
| 3X.283 | H | $CMe=CHCF_3$ | Me | $CF_2H$ | O |
| 3X.284 | H | $CMe=CHCF_3$ | Me | Me | O |
| 3X.285 | H | $CMe=CFCF_3$ | Me | $CF_3$ | O |
| 3X.286 | H | $CMe=CFCF_3$ | Me | $CF_2H$ | O |
| 3X.287 | H | $CMe=CFCF_3$ | Me | Me | O |
| 3X.288 | H | $CMe=CClCF_3$ | Me | $CF_3$ | O |
| 3X.289 | H | $CMe=CClCF_3$ | Me | $CF_2H$ | O |
| 3X.290 | H | $CMe=CClCF_3$ | Me | Me | O |
| 3X.291 | H | $CCF_3=CH_2$ | Me | $CF_3$ | O |
| 3X.292 | H | $CCF_3=CH_2$ | Me | $CF_2H$ | O |
| 3X.293 | H | $CCF_3=CH_2$ | Me | Me | O |
| 3X.294 | H | $CCF_3=CHF$ | Me | $CF_3$ | O |
| 3X.295 | H | $CCF_3=CHF$ | Me | $CF_2H$ | O |
| 3X.296 | H | $CCF_3=CHF$ | Me | Me | O |
| 3X.297 | H | $CCF_3=CHCl$ | Me | $CF_3$ | O |
| 3X.298 | H | $CCF_3=CHCl$ | Me | $CF_2H$ | O |
| 3X.299 | H | $CCF_3=CHCl$ | Me | Me | O |
| 3X.300 | H | $CCF_3=CF_2$ | Me | $CF_3$ | O |
| 3X.301 | H | $CCF_3=CF_2$ | Me | $CF_2H$ | O |
| 3X.302 | H | $CCF_3=CF_2$ | Me | Me | O |
| 3X.303 | H | $CCF_3=CCl_2$ | Me | $CF_3$ | O |
| 3X.304 | H | $CCF_3=CCl_2$ | Me | $CF_2H$ | O |
| 3X.305 | H | $CCF_3=CCl_2$ | Me | Me | O |
| 3X.306 | H | $CCF_3=CBr_2$ | Me | $CF_3$ | O |
| 3X.307 | H | $CCF_3=CBr_2$ | Me | $CF_2H$ | O |
| 3X.308 | H | $CCF_3=CBr_2$ | Me | Me | O |
| 3X.309 | H | $CH_2CH=CF_2$ | Me | $CF_3$ | O |
| 3X.310 | H | $CH_2CH=CF_2$ | Me | $CF_2H$ | O |
| 3X.311 | H | $CH_2CH=CF_2$ | Me | Me | O |
| 3X.312 | H | $CH_2CH=CCl_2$ | Me | $CF_3$ | O |
| 3X.313 | H | $CH_2CH=CCl_2$ | Me | $CF_2H$ | O |
| 3X.314 | H | $CH_2CH=CCl_2$ | Me | Me | O |
| 3X.315 | H | $CH_2CF=CF_2$ | Me | $CF_3$ | O |
| 3X.316 | H | $CH_2CF=CF_2$ | Me | $CF_2H$ | O |
| 3X.317 | H | $CH_2CF=CF_2$ | Me | Me | O |
| 3X.318 | H | $CH_2CF=CCl_2$ | Me | $CF_3$ | O |

TABLE 3-continued

| Compound No. | $R^1$ | $R^6$ | $R^8$ | $R^9$ | X |
|---|---|---|---|---|---|
| 3X.319 | H | $CH_2CF{=}CCl_2$ | Me | $CF_2H$ | O |
| 3X.320 | H | $CH_2CF{=}CCl_2$ | Me | Me | O |

Table 3ca provides 320 compounds of formula (I.ca):

(I.ca)

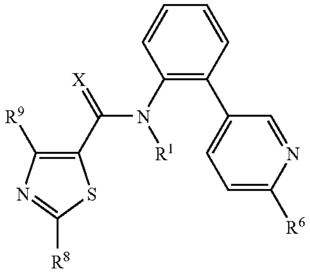

wherein $R^1$, $R^6$, $R^8$, $R^9$ and X are as defined in Table 3ca.

Table 3cb provides 320 compounds of formula (I.cb):

(I.cb)

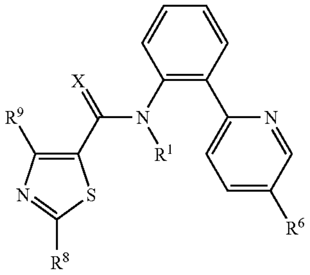

wherein $R^1$, $R^6$, $R^8$, $R^9$ and X are as defined in Table 3cb.

Table 3 cc provides 320 compounds of formula (I.cc)

(I.cc)

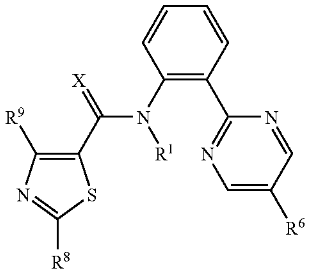

wherein $R^1$, $R^6$, $R^8$, $R^9$ and X are as defined in Table 3 cc.

Table 3cd provides 320 compounds of formula (I.cd)

(I.cd)

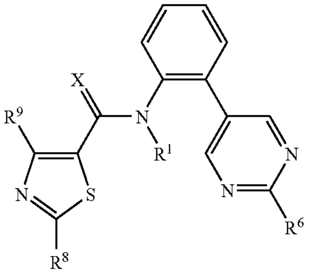

wherein $R^1$, $R^6$, $R^8$, $R^9$ and X are as defined in Table 3cd.

Table 3ce provides 320 compounds of formula (I.ce)

(I.ce)

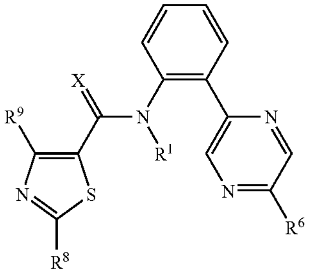

wherein $R^1$, $R^6$, $R^8$, $R^9$ and X are as defined in Table 3ce.

Table 3cf provides 320 compounds of formula (I.cf)

(I.cf)

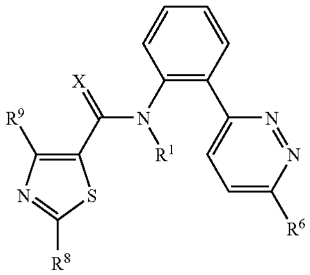

wherein $R^1$, $R^6$, $R^8$, $R^9$ and X are as defined in Table 3cf.

Table 3cg provides 320 compounds of formula (I.cg)

(I.cg)

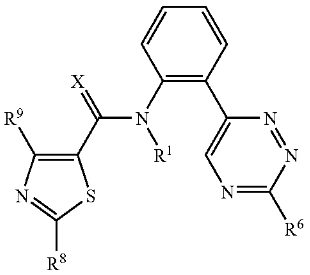

wherein $R^1$, $R^6$, $R^8$, $R^9$ and X are as defined in Table 3cg.

Table 3ch provides 320 compounds of formula (I.ch)

(I.ch)

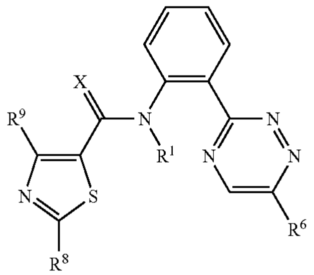

wherein $R^1$, $R^6$, $R^8$, $R^9$ and X are as defined in Table 3ch.

Table 3ci provides 320 compounds of formula (I.ci)

(I.ci)

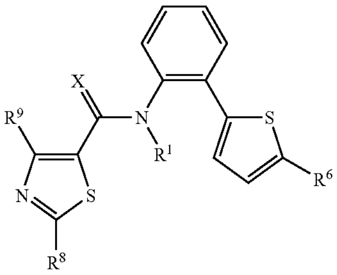

wherein $R^1$, $R^6$, $R^8$, $R^9$ and X are as defined in Table 3ci.

Table 3cj provides 320 compounds of formula (I.cj)

(I.cj)

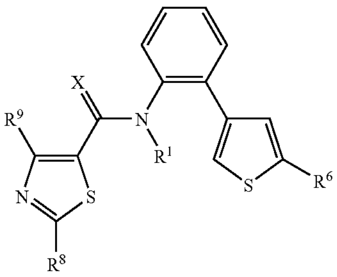

wherein $R^1$, $R^6$, $R^8$, $R^9$ and X are as defined in Table 3cj.

Table 3ck provides 320 compounds of formula (I.ck)

(I.ck)

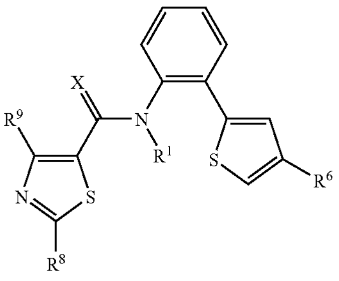

wherein $R^1$, $R^6$, $R^8$, $R^9$ and X are as defined in Table 3ck.

Table 3cl provides 320 compounds of formula (I.cl)

(I.cl)

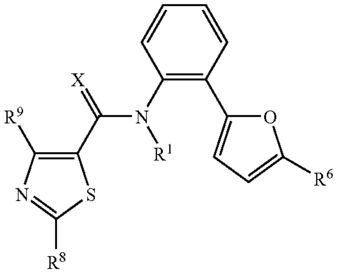

wherein $R^1$, $R^6$, $R^8$, $R^9$ and X are as defined in Table 3cl.

Table 3 cm provides 320 compounds of formula (I.cm)

(I.cm)

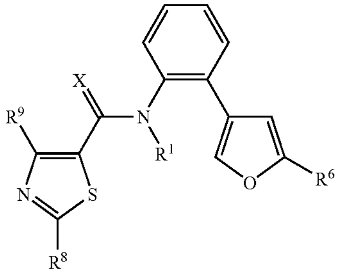

wherein $R^1$, $R^6$, $R^8$, $R^9$ and X are as defined in Table 3cm.

Table 3cn provides 320 compounds of formula (I.cn)

(I.cn)

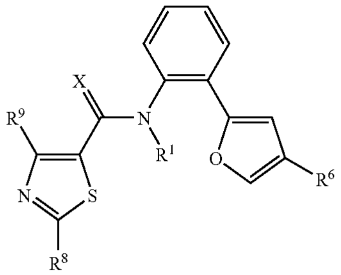

wherein $R^1$, $R^6$, $R^8$, $R^9$ and X are as defined in Table 3cn.

Table 3co provides 320 compounds of formula (I.co)

(I.co)

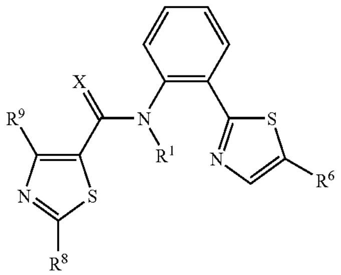

wherein $R^1$, $R^6$, $R^8$, $R^9$ and X are as defined in Table 3co.

Table 3 cp provides 320 compounds of formula (I.cp)

(I.cp)

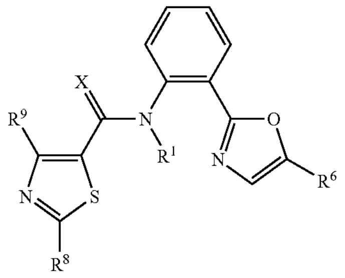

wherein $R^1$, $R^6$, $R^8$, $R^9$ and X are as defined in Table 3 cp.

Table 3cq provides 320 compounds of formula (I.cq)

(I.cq)

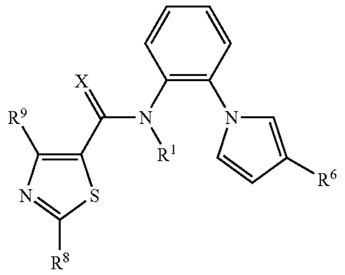

wherein $R^1$, $R^6$, $R^8$, $R^9$ and X are as defined in Table 3cq.

Table 3cr provides 320 compounds of formula (I.cr)

(I.cr)

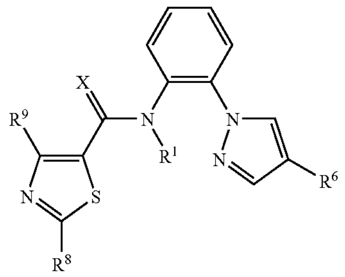

wherein $R^1$, $R^6$, $R^8$, $R^9$ and X are as defined in Table 3cr.

Table 3cs provides 320 compounds of formula (I.cs)

(I.cs)

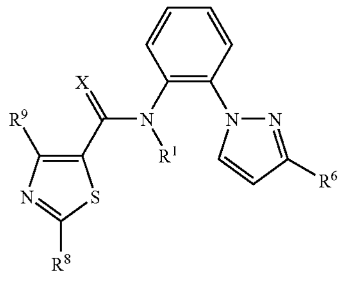

wherein $R^1$, $R^6$, $R^8$, $R^9$ and X are as defined in Table 3cs.

Table 3ct provides 320 compounds of formula (I.ct)

(I.ct)

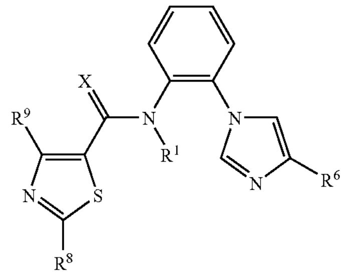

wherein $R^1$, $R^6$, $R^8$, $R^9$ and X are as defined in Table 3ct.

Table 3cu provides 320 compounds of formula (I.cu)

(I.cu)

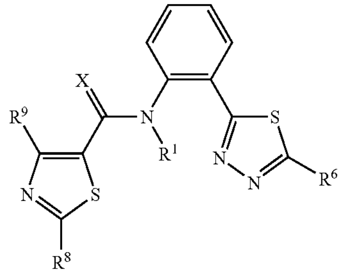

wherein $R^1$, $R^6$, $R^8$, $R^9$ and X are as defined in Table 3cu.

Table 3cv provides 320 compounds of formula (I.cv)

(I.cv)

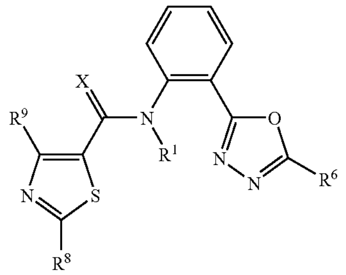

wherein $R^1$, $R^6$, $R^8$, $R^9$ and X are as defined in Table 3cv.

Table 3cw provides 320 compounds of formula (I.cw)

(I.cw)

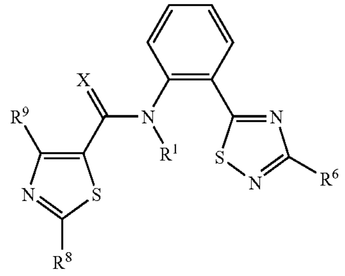

wherein $R^1$, $R^6$, $R^8$, $R^9$ and X are as defined in Table 3cw.

Table 3cx provides 320 compounds of formula (I.cx)

(I.cx)

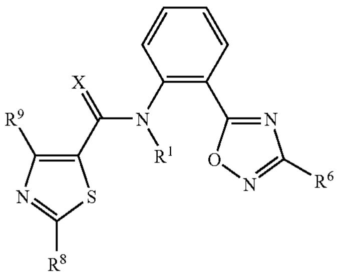

wherein $R^1$, $R^6$, $R^8$, $R^9$ and X are as defined in Table 3cx.

Table 4X represents Table 4da (when X is da), represents Table 4db (when X is db), represents Table 4dc (when X is dc), represents Table 4dd (when X is dd), represents Table 4de (when X is de), represents Table 4df (when X is df), represents Table 4dg (when X is dg), represents Table 4dh (when X is dh), represents Table 4di (when X is di), represents Table 4dj (when X is dj), represents Table 4dk (when X is dk), represents Table 4dl (when X is dl), represents Table 4dm (when X is dm), represents Table 4dn (when X is dn), represents Table 4do (when X is do), represents Table 4dp (when X is dp), represents Table 4dq (when X is dq), represents Table 4dr (when X is dr), represents Table 4ds (when X is ds), represents Table 4dt (when X is dt), represents Table 4du (when X is du), represents Table 4dv (when X is dv), represents Table 4dw (when X is dw) and represents Table 4dx (when X is dx).

TABLE 4

| Compound No. | $R^1$ | $R^6$ | $R^8$ | X |
|---|---|---|---|---|
| 4X.001 | H | $C\equiv CH$ | Cl | O |
| 4X.002 | H | $C\equiv CH$ | Br | O |
| 4X.003 | H | $C\equiv CH$ | $CF_3$ | O |
| 4X.004 | H | $C\equiv CH$ | Cl | S |
| 4X.005 | H | $C\equiv CH$ | Br | S |
| 4X.006 | propargyl | $C\equiv CH$ | Cl | O |
| 4X.007 | allenyl | $C\equiv CH$ | Cl | O |
| 4X.008 | COMe | $C\equiv CH$ | Cl | O |
| 4X.009 | H | $C\equiv CF$ | Cl | O |
| 4X.010 | H | $C\equiv CF$ | Br | O |
| 4X.011 | H | $C\equiv CF$ | $CF_3$ | O |
| 4X.012 | H | $C\equiv CCl$ | Cl | O |
| 4X.013 | H | $C\equiv CCl$ | Br | O |
| 4X.014 | H | $C\equiv CCl$ | $CF_3$ | O |
| 4X.015 | H | $C\equiv CBr$ | Cl | O |
| 4X.016 | H | $C\equiv CBr$ | Br | O |
| 4X.017 | H | $C\equiv CBr$ | $CF_3$ | O |
| 4X.018 | H | $C\equiv CMe$ | Cl | O |
| 4X.019 | H | $C\equiv CMe$ | Br | O |
| 4X.020 | H | $C\equiv CMe$ | $CF_3$ | O |
| 4X.021 | H | $C\equiv CCH_2OMe$ | Cl | O |
| 4X.022 | H | $C\equiv CCH_2OMe$ | Br | O |
| 4X.023 | H | $C\equiv CCH_2OMe$ | $CF_3$ | O |
| 4X.024 | H | $C\equiv CCH_2F$ | Cl | O |
| 4X.025 | H | $C\equiv CCH_2F$ | Br | O |
| 4X.026 | H | $C\equiv CCH_2F$ | $CF_3$ | O |
| 4X.027 | H | $C\equiv CCF_2H$ | Cl | O |
| 4X.028 | H | $C\equiv CCF_2H$ | Br | O |
| 4X.029 | H | $C\equiv CCF_2H$ | $CF_3$ | O |
| 4X.030 | H | $C\equiv CCHFCl$ | Cl | O |
| 4X.031 | H | $C\equiv CCHFCl$ | Br | O |
| 4X.032 | H | $C\equiv CCHFCl$ | $CF_3$ | O |
| 4X.033 | H | $C\equiv CCF_2Cl$ | Cl | O |
| 4X.034 | H | $C\equiv CCF_2Cl$ | Br | O |
| 4X.035 | H | $C\equiv CCF_2Cl$ | $CF_3$ | O |
| 4X.036 | H | $C\equiv CCF_2Br$ | Cl | O |

TABLE 4-continued

| Compound No. | $R^1$ | $R^6$ | $R^8$ | X |
|---|---|---|---|---|
| 4X.037 | H | $C\equiv CCF_2Br$ | Br | O |
| 4X.038 | H | $C\equiv CCF_2Br$ | $CF_3$ | O |
| 4X.039 | H | $C\equiv CCF_3$ | Cl | O |
| 4X.040 | H | $C\equiv CCF_3$ | Br | O |
| 4X.041 | H | $C\equiv CCF_3$ | $CF_3$ | O |
| 4X.042 | H | $C\equiv CCF_3$ | Cl | S |
| 4X.043 | H | $C\equiv CCF_3$ | Br | S |
| 4X.044 | propargyl | $C\equiv CCF_3$ | Cl | O |
| 4X.045 | allenyl | $C\equiv CCF_3$ | Cl | O |
| 4X.046 | COMe | $C\equiv CCF_3$ | Cl | O |
| 4X.047 | H | $C\equiv CCH_2CH_3$ | Cl | O |
| 4X.048 | H | $C\equiv CCH_2CH_3$ | Br | O |
| 4X.049 | H | $C\equiv CCH_2CH_3$ | $CF_3$ | O |
| 4X.050 | H | $C\equiv CCH(Me)F$ | Cl | O |
| 4X.051 | H | $C\equiv CCH(Me)F$ | Br | O |
| 4X.052 | H | $C\equiv CCH(Me)F$ | $CF_3$ | O |
| 4X.053 | H | $C\equiv CCF_2Me$ | Cl | O |
| 4X.054 | H | $C\equiv CCF_2Me$ | Br | O |
| 4X.055 | H | $C\equiv CCF_2Me$ | $CF_3$ | O |
| 4X.056 | H | $C\equiv CCH_2CF_3$ | Cl | O |
| 4X.057 | H | $C\equiv CCH_2CF_3$ | Br | O |
| 4X.058 | H | $C\equiv CCH_2CF_3$ | $CF_3$ | O |
| 4X.059 | H | $C\equiv CC_2F_5$ | Cl | O |
| 4X.060 | H | $C\equiv CC_2F_5$ | Br | O |
| 4X.061 | H | $C\equiv CC_2F_5$ | $CF_3$ | O |
| 4X.062 | H | $C\equiv CCF{=}CF_2$ | Cl | O |
| 4X.063 | H | $C\equiv CCF{=}CF_2$ | Br | O |
| 4X.064 | H | $C\equiv CCF{=}CF_2$ | $CF_3$ | O |
| 4X.065 | H | $C\equiv CCH_2CH_2CH_3$ | Cl | O |
| 4X.066 | H | $C\equiv CCH_2CH_2CH_3$ | Br | O |
| 4X.067 | H | $C\equiv CCH_2CH_2CH_3$ | $CF_3$ | O |
| 4X.068 | H | $C\equiv CCHFCH_2CH_3$ | Cl | O |
| 4X.069 | H | $C\equiv CCHFCH_2CH_3$ | Br | O |
| 4X.070 | H | $C\equiv CCHFCH_2CH_3$ | $CF_3$ | O |
| 4X.071 | H | $C\equiv CCF_2CH_2CH_3$ | Cl | O |
| 4X.072 | H | $C\equiv CCF_2CH_2CH_3$ | Br | O |
| 4X.073 | H | $C\equiv CCF_2CH_2CH_3$ | $CF_3$ | O |
| 4X.074 | H | $C\equiv CCH(Me)_2$ | Cl | O |
| 4X.075 | H | $C\equiv CCH(Me)_2$ | Br | O |
| 4X.076 | H | $C\equiv CCH(Me)_2$ | $CF_3$ | O |
| 4X.077 | H | $C\equiv CCMe_2OMe$ | Cl | O |
| 4X.078 | H | $C\equiv CCMe_2OMe$ | Br | O |
| 4X.079 | H | $C\equiv CCMe_2OMe$ | $CF_3$ | O |
| 4X.080 | H | $C\equiv CC(Me)_2F$ | Cl | O |
| 4X.081 | H | $C\equiv CC(Me)_2F$ | Br | O |
| 4X.082 | H | $C\equiv CC(Me)_2F$ | $CF_3$ | O |
| 4X.083 | H | $C\equiv CCF(CF_3)_2$ | Cl | O |
| 4X.084 | H | $C\equiv CCF(CF_3)_2$ | Br | O |
| 4X.085 | H | $C\equiv CCF(CF_3)_2$ | $CF_3$ | O |
| 4X.086 | H | $C\equiv CC(Me){=}CH_2$ | Cl | O |
| 4X.087 | H | $C\equiv CC(Me){=}CH_2$ | Br | O |
| 4X.088 | H | $C\equiv CC(Me){=}CH_2$ | $CF_3$ | O |
| 4X.089 | H | $C\equiv C$(cyclopropyl) | Cl | O |
| 4X.090 | H | $C\equiv C$(cyclopropyl) | Br | O |
| 4X.091 | H | $C\equiv C$(cyclopropyl) | $CF_3$ | O |
| 4X.092 | H | $C\equiv CCH_2CH(Me)_2$ | Cl | O |
| 4X.093 | H | $C\equiv CCH_2CH(Me)_2$ | Br | O |
| 4X.094 | H | $C\equiv CCH_2CH(Me)_2$ | $CF_3$ | O |
| 4X.095 | H | $C\equiv CCH(Me)CH_2CH_3$ | Cl | O |
| 4X.096 | H | $C\equiv CCH(Me)CH_2CH_3$ | Br | O |
| 4X.097 | H | $C\equiv CCH(Me)CH_2CH_3$ | $CF_3$ | O |
| 4X.098 | H | $C\equiv CCMe_3$ | Cl | O |
| 4X.099 | H | $C\equiv CCMe_3$ | Br | O |
| 4X.100 | H | $C\equiv CCMe_3$ | $CF_3$ | O |
| 4X.101 | H | $C\equiv CCMe_3$ | Cl | S |
| 4X.102 | H | $C\equiv CCMe_3$ | Br | S |
| 4X.103 | propargyl | $C\equiv CCMe_3$ | Cl | O |
| 4X.104 | allenyl | $C\equiv CCMe_3$ | Cl | O |
| 4X.105 | COMe | $C\equiv CCMe_3$ | Cl | O |
| 4X.106 | H | $C\equiv CSiMe_3$ | Cl | O |
| 4X.107 | H | $C\equiv CSiMe_3$ | Br | O |
| 4X.108 | H | $C\equiv CSiMe_3$ | $CF_3$ | O |
| 4X.109 | H | $C\equiv CCH_2C(Me)_3$ | Cl | O |
| 4X.110 | H | $C\equiv CCH_2C(Me)_3$ | Br | O |
| 4X.111 | H | $C\equiv CCH_2C(Me)_3$ | $CF_3$ | O |
| 4X.112 | H | $C\equiv CCH_2SiMe_3$ | Cl | O |

TABLE 4-continued

| Compound No. | $R^1$ | $R^6$ | $R^8$ | X |
|---|---|---|---|---|
| 4X.113 | H | $C{\equiv}CCH_2SiMe_3$ | Br | O |
| 4X.114 | H | $C{\equiv}CCH_2SiMe_3$ | $CF_3$ | O |
| 4X.115 | H | $C{\equiv}C$ (1-F-cyclopentyl) | Cl | O |
| 4X.116 | H | $C{\equiv}C$ (1-F-cyclopentyl) | Br | O |
| 4X.117 | H | $C{\equiv}C$ (1-F-cyclopentyl) | $CF_3$ | O |
| 4X.118 | H | $C{\equiv}CSi(Me_2)CMe_3$ | Cl | O |
| 4X.119 | H | $C{\equiv}CSi(Me_2)CMe_3$ | Br | O |
| 4X.120 | H | $C{\equiv}CSi(Me_2)CMe_3$ | $CF_3$ | O |
| 4X.121 | H | $CH_2C{\equiv}CH$ | Cl | O |
| 4X.122 | H | $CH_2C{\equiv}CH$ | Br | O |
| 4X.123 | H | $CH_2C{\equiv}CH$ | $CF_3$ | O |
| 4X.124 | H | $CHFC{\equiv}CH$ | Cl | O |
| 4X.125 | H | $CHFC{\equiv}CH$ | Br | O |
| 4X.126 | H | $CHFC{\equiv}CH$ | $CF_3$ | O |
| 4X.127 | H | $CF_2C{\equiv}CH$ | Cl | O |
| 4X.128 | H | $CF_2C{\equiv}CH$ | Br | O |
| 4X.129 | H | $CF_2C{\equiv}CH$ | $CF_3$ | O |
| 4X.130 | H | $CHMeC{\equiv}CH$ | Cl | O |
| 4X.131 | H | $CHMeC{\equiv}CH$ | Br | O |
| 4X.132 | H | $CHMeC{\equiv}CH$ | $CF_3$ | O |
| 4X.133 | H | $CH(CF_3)C{\equiv}CH$ | Cl | O |
| 4X.134 | H | $CH(CF_3)C{\equiv}CH$ | Br | O |
| 4X.135 | H | $CH(CF_3)C{\equiv}CH$ | $CF_3$ | O |
| 4X.136 | H | $CMe_2C{\equiv}CH$ | Cl | O |
| 4X.137 | H | $CMe_2C{\equiv}CH$ | Br | O |
| 4X.138 | H | $CMe_2C{\equiv}CH$ | $CF_3$ | O |
| 4X.139 | H | $CH_2C{\equiv}CMe$ | Cl | O |
| 4X.140 | H | $CH_2C{\equiv}CMe$ | Br | O |
| 4X.141 | H | $CH_2C{\equiv}CMe$ | $CF_3$ | O |
| 4X.142 | H | $CF_2C{\equiv}CMe$ | Cl | O |
| 4X.143 | H | $CF_2C{\equiv}CMe$ | Br | O |
| 4X.144 | H | $CF_2C{\equiv}CMe$ | $CF_3$ | O |
| 4X.145 | H | $CH_2C{\equiv}CCF_3$ | Cl | O |
| 4X.146 | H | $CH_2C{\equiv}CCF_3$ | Br | O |
| 4X.147 | H | $CH_2C{\equiv}CCF_3$ | $CF_3$ | O |
| 4X.148 | H | $CF_2C{\equiv}CCF_3$ | Cl | O |
| 4X.149 | H | $CF_2C{\equiv}CCF_3$ | Br | O |
| 4X.150 | H | $CF_2C{\equiv}CCF_3$ | $CF_3$ | O |
| 4X.151 | H | $CH_2C{\equiv}CCMe_3$ | Cl | O |
| 4X.152 | H | $CH_2C{\equiv}CCMe_3$ | Br | O |
| 4X.153 | H | $CH_2C{\equiv}CCMe_3$ | $CF_3$ | O |
| 4X.154 | H | $CF_2C{\equiv}CCMe_3$ | Cl | O |
| 4X.155 | H | $CF_2C{\equiv}CCMe_3$ | Br | O |
| 4X.156 | H | $CF_2C{\equiv}CCMe_3$ | $CF_3$ | O |
| 4X.157 | H | $CH_2C{\equiv}CSiMe_3$ | Cl | O |
| 4X.158 | H | $CH_2C{\equiv}CSiMe_3$ | Br | O |
| 4X.159 | H | $CH_2C{\equiv}CSiMe_3$ | $CF_3$ | O |
| 4X.160 | H | $CF_2C{\equiv}CSiMe_3$ | Cl | O |
| 4X.161 | H | $CF_2C{\equiv}CSiMe_3$ | Br | O |
| 4X.162 | H | $CF_2C{\equiv}CSiMe_3$ | $CF_3$ | O |
| 4X.163 | H | $CH{=}CH_2$ | Cl | O |
| 4X.164 | H | $CH{=}CH_2$ | Br | O |
| 4X.165 | H | $CH{=}CH_2$ | $CF_3$ | O |
| 4X.166 | H | $CH{=}CH_2$ | Cl | S |
| 4X.167 | H | $CH{=}CH_2$ | Br | S |
| 4X.168 | propargyl | $CH{=}CH_2$ | Cl | O |
| 4X.169 | allenyl | $CH{=}CH_2$ | Cl | O |
| 4X.170 | COMe | $CH{=}CH_2$ | Cl | O |
| 4X.171 | H | $CH{=}CHF$ | Cl | O |
| 4X.172 | H | $CH{=}CHF$ | Br | O |
| 4X.173 | H | $CH{=}CHF$ | $CF_3$ | O |
| 4X.174 | H | $CH{=}CHCl$ | Cl | O |
| 4X.175 | H | $CH{=}CHCl$ | Br | O |
| 4X.176 | H | $CH{=}CHCl$ | $CF_3$ | O |
| 4X.177 | H | $CH{=}CHBr$ | Cl | O |
| 4X.178 | H | $CH{=}CHBr$ | Br | O |
| 4X.179 | H | $CH{=}CHBr$ | $CF_3$ | O |
| 4X.180 | H | $CH{=}CF_2$ | Cl | O |
| 4X.181 | H | $CH{=}CF_2$ | Br | O |
| 4X.182 | H | $CH{=}CF_2$ | $CF_3$ | O |
| 4X.183 | H | $CH{=}CFCl$ | Cl | O |
| 4X.184 | H | $CH{=}CFCl$ | Br | O |
| 4X.185 | H | $CH{=}CFCl$ | $CF_3$ | O |
| 4X.186 | H | $CH{=}CFBr$ | Cl | O |
| 4X.187 | H | $CH{=}CFBr$ | Br | O |
| 4X.188 | H | $CH{=}CFBr$ | $CF_3$ | O |
| 4X.189 | H | $CH{=}CCl_2$ | Cl | O |
| 4X.190 | H | $CH{=}CCl_2$ | Br | O |
| 4X.191 | H | $CH{=}CCl_2$ | $CF_3$ | O |
| 4X.192 | H | $CH{=}CBr_2$ | Cl | O |
| 4X.193 | H | $CH{=}CBr_2$ | Br | O |
| 4X.194 | H | $CH{=}CBr_2$ | $CF_3$ | O |
| 4X.195 | H | $CF{=}CH_2$ | Cl | O |
| 4X.196 | H | $CF{=}CH_2$ | Br | O |
| 4X.197 | H | $CF{=}CH_2$ | $CF_3$ | O |
| 4X.198 | H | $CF{=}CHF$ | Cl | O |
| 4X.199 | H | $CF{=}CHF$ | Br | O |
| 4X.200 | H | $CF{=}CHF$ | $CF_3$ | O |
| 4X.201 | H | $CF{=}CF_2$ | Cl | O |
| 4X.202 | H | $CF{=}CF_2$ | Br | O |
| 4X.203 | H | $CF{=}CF_2$ | $CF_3$ | O |
| 4X.204 | H | $CF{=}CFCl$ | Cl | O |
| 4X.205 | H | $CF{=}CFCl$ | Br | O |
| 4X.206 | H | $CF{=}CFCl$ | $CF_3$ | O |
| 4X.207 | H | $CF{=}CFBr$ | Cl | O |
| 4X.208 | H | $CF{=}CFBr$ | Br | O |
| 4X.209 | H | $CF{=}CFBr$ | $CF_3$ | O |
| 4X.210 | H | $CF{=}CCl_2$ | Cl | O |
| 4X.211 | H | $CF{=}CCl_2$ | Br | O |
| 4X.212 | H | $CF{=}CCl_2$ | $CF_3$ | O |
| 4X.213 | H | $CCl{=}CH_2$ | Cl | O |
| 4X.214 | H | $CCl{=}CH_2$ | Br | O |
| 4X.215 | H | $CCl{=}CH_2$ | $CF_3$ | O |
| 4X.216 | H | $CCl{=}CF_2$ | Cl | O |
| 4X.217 | H | $CCl{=}CF_2$ | Br | O |
| 4X.218 | H | $CCl{=}CF_2$ | $CF_3$ | O |
| 4X.219 | H | $CBr{=}CH_2$ | Cl | O |
| 4X.220 | H | $CBr{=}CH_2$ | Br | O |
| 4X.221 | H | $CBr{=}CH_2$ | $CF_3$ | O |
| 4X.222 | H | $CBr{=}CF_2$ | Cl | O |
| 4X.223 | H | $CBr{=}CF_2$ | Br | O |
| 4X.224 | H | $CBr{=}CF_2$ | $CF_3$ | O |
| 4X.225 | H | $CH{=}CHCF_3$ | Cl | O |
| 4X.226 | H | $CH{=}CHCF_3$ | Br | O |
| 4X.227 | H | $CH{=}CHCF_3$ | $CF_3$ | O |
| 4X.228 | H | $CH{=}CFCF_3$ | Cl | O |
| 4X.229 | H | $CH{=}CFCF_3$ | Br | O |
| 4X.230 | H | $CH{=}CFCF_3$ | $CF_3$ | O |
| 4X.231 | H | $CH{=}CClCF_3$ | Cl | O |
| 4X.232 | H | $CH{=}CClCF_3$ | Br | O |
| 4X.233 | H | $CH{=}CClCF_3$ | $CF_3$ | O |
| 4X.234 | H | $CH{=}CBrCF_3$ | Cl | O |
| 4X.235 | H | $CH{=}CBrCF_3$ | Br | O |
| 4X.236 | H | $CH{=}CBrCF_3$ | $CF_3$ | O |
| 4X.237 | H | $CH{=}CFCF_2Cl$ | Cl | O |
| 4X.238 | H | $CH{=}CFCF_2Cl$ | Br | O |
| 4X.239 | H | $CH{=}CFCF_2Cl$ | $CF_3$ | O |
| 4X.240 | H | $CH{=}CClCF_2Cl$ | Cl | O |
| 4X.241 | H | $CH{=}CClCF_2Cl$ | Br | O |
| 4X.242 | H | $CH{=}CClCF_2Cl$ | $CF_3$ | O |
| 4X.243 | H | $CF{=}CHCF_3$ | Cl | O |
| 4X.244 | H | $CF{=}CHCF_3$ | Br | O |
| 4X.245 | H | $CF{=}CHCF_3$ | $CF_3$ | O |
| 4X.246 | H | $CF{=}CFCF_3$ | Cl | O |
| 4X.247 | H | $CF{=}CFCF_3$ | Br | O |
| 4X.248 | H | $CF{=}CFCF_3$ | $CF_3$ | O |
| 4X.249 | H | $CH{=}CHC_2F_5$ | Cl | O |
| 4X.250 | H | $CH{=}CHC_2F_5$ | Br | O |
| 4X.251 | H | $CH{=}CHC_2F_5$ | $CF_3$ | O |
| 4X.252 | H | $CH{=}CFC_2F_5$ | Cl | O |
| 4X.253 | H | $CH{=}CFC_2F_5$ | Br | O |
| 4X.254 | H | $CH{=}CFC_2F_5$ | $CF_3$ | O |
| 4X.255 | H | $CH{=}CClC_2F_5$ | Cl | O |
| 4X.256 | H | $CH{=}CClC_2F_5$ | Br | O |
| 4X.257 | H | $CH{=}CClC_2F_5$ | $CF_3$ | O |
| 4X.258 | H | $CH{=}C(CF_3)_2$ | Cl | O |
| 4X.259 | H | $CH{=}C(CF_3)_2$ | Br | O |
| 4X.260 | H | $CH{=}C(CF_3)_2$ | $CF_3$ | O |
| 4X.261 | H | $CF{=}C(CF_3)_2$ | Cl | O |
| 4X.262 | H | $CF{=}C(CF_3)_2$ | Br | O |
| 4X.263 | H | $CF{=}C(CF_3)_2$ | $CF_3$ | O |
| 4X.264 | H | $CH{=}CHSiMe_3$ | Cl | O |

TABLE 4-continued

| Compound No. | $R^1$ | $R^6$ | $R^8$ | X |
|---|---|---|---|---|
| 4X.265 | H | $CH{=}CHSiMe_3$ | Br | O |
| 4X.266 | H | $CH{=}CHSiMe_3$ | $CF_3$ | O |
| 4X.267 | H | $CMe{=}CF_2$ | Cl | O |
| 4X.268 | H | $CMe{=}CF_2$ | Br | O |
| 4X.269 | H | $CMe{=}CF_2$ | $CF_3$ | O |
| 4X.270 | H | $CMe{=}CFCl$ | Cl | O |
| 4X.271 | H | $CMe{=}CFCl$ | Br | O |
| 4X.272 | H | $CMe{=}CFCl$ | $CF_3$ | O |
| 4X.273 | H | $CMe{=}CFBr$ | Cl | O |
| 4X.274 | H | $CMe{=}CFBr$ | Br | O |
| 4X.275 | H | $CMe{=}CFBr$ | $CF_3$ | O |
| 4X.276 | H | $CMe{=}CCl_2$ | Cl | O |
| 4X.277 | H | $CMe{=}CCl_2$ | Br | O |
| 4X.278 | H | $CMe{=}CCl_2$ | $CF_3$ | O |
| 4X.279 | H | $CMe{=}CBr_2$ | Cl | O |
| 4X.280 | H | $CMe{=}CBr_2$ | Br | O |
| 4X.281 | H | $CMe{=}CBr_2$ | $CF_3$ | O |
| 4X.282 | H | $CMe{=}CHCF_3$ | Cl | O |
| 4X.283 | H | $CMe{=}CHCF_3$ | Br | O |
| 4X.284 | H | $CMe{=}CHCF_3$ | $CF_3$ | O |
| 4X.285 | H | $CMe{=}CFCF_3$ | Cl | O |
| 4X.286 | H | $CMe{=}CFCF_3$ | Br | O |
| 4X.287 | H | $CMe{=}CFCF_3$ | $CF_3$ | O |
| 4X.288 | H | $CMe{=}CClCF_3$ | Cl | O |
| 4X.289 | H | $CMe{=}CClCF_3$ | Br | O |
| 4X.290 | H | $CMe{=}CClCF_3$ | $CF_3$ | O |
| 4X.291 | H | $CCF_3{=}CH_2$ | Cl | O |
| 4X.292 | H | $CCF_3{=}CH_2$ | Br | O |
| 4X.293 | H | $CCF_3{=}CH_2$ | $CF_3$ | O |
| 4X.294 | H | $CCF_3{=}CHF$ | Cl | O |
| 4X.295 | H | $CCF_3{=}CHF$ | Br | O |
| 4X.296 | H | $CCF_3{=}CHF$ | $CF_3$ | O |
| 4X.297 | H | $CCF_3{=}CHCl$ | Cl | O |
| 4X.298 | H | $CCF_3{=}CHCl$ | Br | O |
| 4X.299 | H | $CCF_3{=}CHCl$ | $CF_3$ | O |
| 4X.300 | H | $CCF_3{=}CF_2$ | Cl | O |
| 4X.301 | H | $CCF_3{=}CF_2$ | Br | O |
| 4X.302 | H | $CCF_3{=}CF_2$ | $CF_3$ | O |
| 4X.303 | H | $CCF_3{=}CCl_2$ | Cl | O |
| 4X.304 | H | $CCF_3{=}CCl_2$ | Br | O |
| 4X.305 | H | $CCF_3{=}CCl_2$ | $CF_3$ | O |
| 4X.306 | H | $CCF_3{=}CBr_2$ | Cl | O |
| 4X.307 | H | $CCF_3{=}CBr_2$ | Br | O |
| 4X.308 | H | $CCF_3{=}CBr_2$ | $CF_3$ | O |
| 4X.309 | H | $CH_2CH{=}CF_2$ | Cl | O |
| 4X.310 | H | $CH_2CH{=}CF_2$ | Br | O |
| 4X.311 | H | $CH_2CH{=}CF_2$ | $CF_3$ | O |
| 4X.312 | H | $CH_2CH{=}CCl_2$ | Cl | O |
| 4X.313 | H | $CH_2CH{=}CCl_2$ | Br | O |
| 4X.314 | H | $CH_2CH{=}CCl_2$ | $CF_3$ | O |
| 4X.315 | H | $CH_2CF{=}CF_2$ | Cl | O |
| 4X.316 | H | $CH_2CF{=}CF_2$ | Br | O |
| 4X.317 | H | $CH_2CF{=}CF_2$ | $CF_3$ | O |
| 4X.318 | H | $CH_2CF{=}CCl_2$ | Cl | O |
| 4X.319 | H | $CH_2CF{=}CCl_2$ | Br | O |
| 4X.320 | H | $CH_2CF{=}CCl_2$ | $CF_3$ | O |

Table 4da provides 320 compounds of formula (I.da):

(I.da)

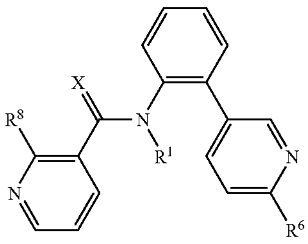

wherein $R^1$, $R^6$, $R^8$ and X are as defined in Table 4da.

Table 4db provides 320 compounds of formula (I.db):

(I.db)

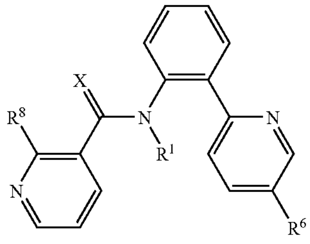

wherein $R^1$, $R^6$, $R^9$ and X are as defined in Table 4db.

Table 4dc provides 320 compounds of formula (I.dc)

(I.dc)

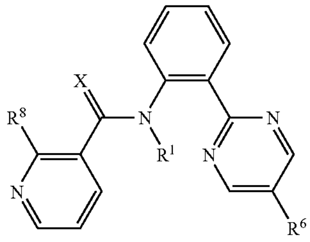

wherein $R^1$, $R^6$, $R^8$ and X are as defined in Table 4dc.

Table 4dd provides 320 compounds of formula (I.dd)

(I.dd)

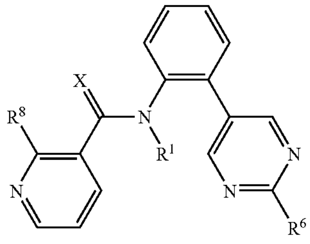

wherein $R^1$, $R^6$, $R^8$ and X are as defined in Table 4dd.

Table 4de provides 320 compounds of formula (I.de)

(I.de)

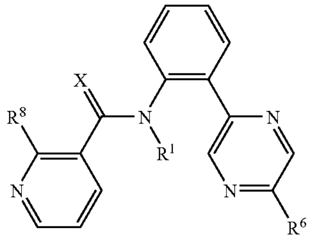

wherein $R^1$, $R^6$, $R^8$ and X are as defined in Table 4de.

Table 4df provides 320 compounds of formula (I.df)

(I.df)

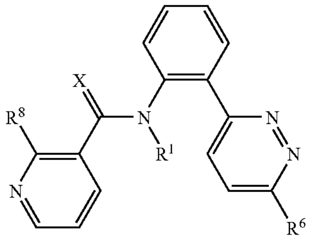

wherein $R^1$, $R^6$, $R^8$ and X are as defined in Table 4df.

Table 4dg provides 320 compounds of formula (I.dg)

(I.dg)

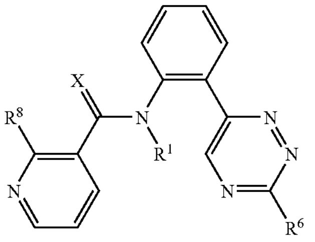

wherein $R^1$, $R^6$, $R^8$ and X are as defined in Table 4dg.

Table 4dh provides 320 compounds of formula (I.dh)

(I.dh)

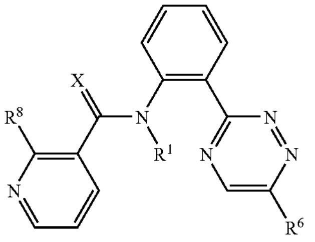

wherein $R^1$, $R^6$, $R^8$ and X are as defined in Table 4dh.

Table 4di provides 320 compounds of formula (I.di)

(I.di)

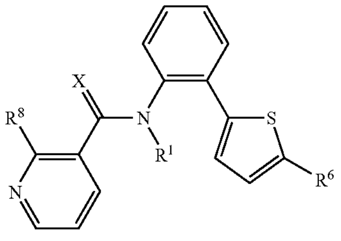

wherein $R^1$, $R^6$, $R^8$ and X are as defined in Table 4di.

Table 4dj provides 320 compounds of formula (I.dj)

(I.dj)

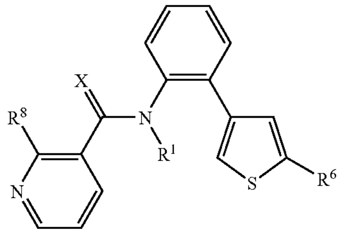

wherein $R^1$, $R^6$, $R^8$ and X are as defined in Table 4dj.

Table 4dk provides 320 compounds of formula (I.dk)

(I.dk)

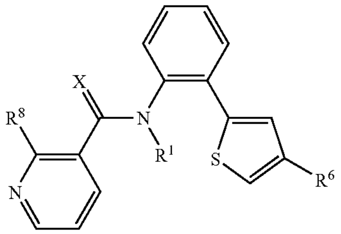

wherein $R^1$, $R^6$, $R^8$ and X are as defined in Table 4dk.

Table 4dl provides 320 compounds of formula (I.dl)

(I.dl)

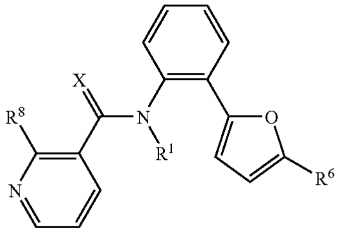

wherein $R^1$, $R^6$, $R^8$ and X are as defined in Table 4dl.

Table 4dm provides 320 compounds of formula (I.dm)

(I.dm)

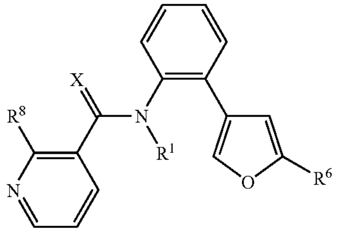

wherein $R^1$, $R^6$, $R^8$ and X are as defined in Table 4dm.

Table 4dn provides 320 compounds of formula (I.dn)

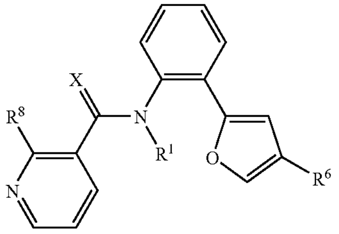

(I.dn)

wherein $R^1$, $R^6$, $R^8$ and X are as defined in Table 4dn.

Table 4do provides 320 compounds of formula (I.do)

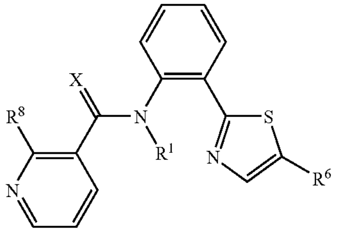

(I.do)

wherein $R^1$, $R^6$, $R^8$ and X are as defined in Table 4do.

Table 4dp provides 320 compounds of formula (I.dp)

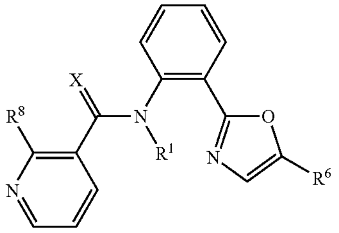

(I.dp)

wherein $R^1$, $R^6$, $R^8$ and X are as defined in Table 4dp.

Table 4dq provides 320 compounds of formula (I.dq)

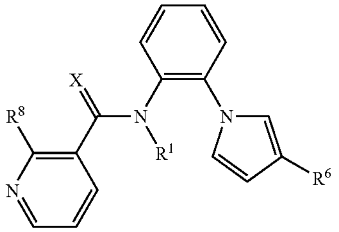

(I.dq)

wherein $R^1$, $R^6$, $R^8$ and X are as defined in Table 4dq.

Table 4dr provides 320 compounds of formula (I.dr)

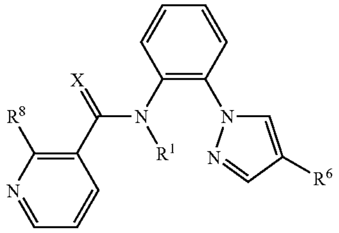

(I.dr)

wherein $R^1$, $R^6$, $R^8$ and X are as defined in Table 4dr.

Table 4ds provides 320 compounds of formula (I.ds)

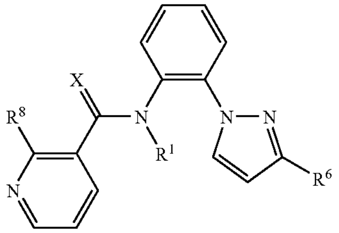

(I.ds)

wherein $R^1$, $R^6$, $R^8$ and X are as defined in Table 4ds.

Table 4dt provides 320 compounds of formula (I.dt)

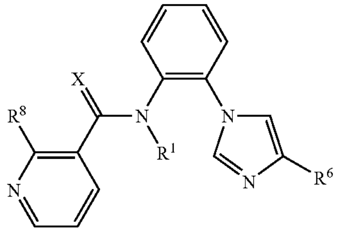

(I.dt)

wherein $R^1$, $R^6$, $R^8$ and X are as defined in Table 4dt.

Table 4du provides 287 compounds of formula (I.du)

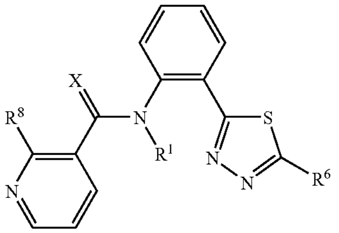

(I.du)

wherein $R^1$, $R^6$, $R^8$ and X are as defined in Table 4du.

Table 4dv provides 320 compounds of formula (I.dv)

(I.dv)

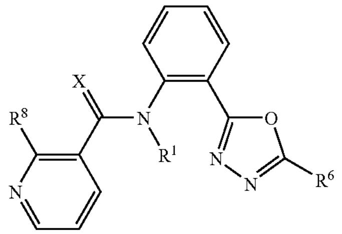

wherein $R^1$, $R^6$, $R^8$ and X are as defined in Table 4dv.

Table 4dw provides 320 compounds of formula (I.dw)

(I.dw)

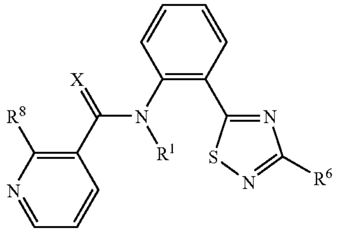

wherein $R^1$, $R^6$, $R^8$ and X are as defined in Table 4dw.

Table 4dx provides 320 compounds of formula (I.dx)

(I.dx)

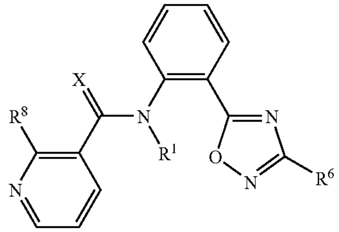

wherein $R^1$, $R^6$, $R^8$ and X are as defined in Table 4dx.

Table 5X represents Table 5a (when X is a), represents Table 5b (when X is b), represents Table 5c (when X is c), represents Table 5d (when X is d), represents Table 5e (when X is e), represents Table 5f (when X is f), represents Table 5g (when X is g), represents Table 5h (when X is h), represents Table 5i (when X is i), represents Table 5j (when X is j), represents Table 5k (when X is k), represents Table 5l (when X is l), represents Table 5m (when X is m), represents Table 5n (when X is n), represents Table 5o (when X is o), represents Table 5p (when X is p), represents Table 5q (when X is q), represents Table 5r (when X is r), represents Table 5s (when X is s), represents Table 5t (when X is t), represents Table 5u (when X is u), represents Table 5v (when X is v), represents Table 5w (when X is w) and represents Table 5x (when X is x).

TABLE 5

| Compound No. | $R^1$ | $R^6$ |
|---|---|---|
| 5X.001 | H | $C\equiv CH$ |
| 5X.002 | H | $C\equiv CF$ |
| 5X.003 | H | $C\equiv CCl$ |
| 5X.004 | H | $C\equiv CBr$ |
| 5X.005 | H | $C\equiv CMe$ |
| 5X.006 | H | $C\equiv CCH_2OMe$ |
| 5X.007 | H | $C\equiv CCH_2F$ |
| 5X.008 | H | $C\equiv CCF_2H$ |
| 5X.009 | H | $C\equiv CCHFCl$ |
| 5X.010 | H | $C\equiv CCF_2Cl$ |
| 5X.011 | H | $C\equiv CCF_2Br$ |
| 5X.012 | H | $C\equiv CCF_3$ |
| 5X.013 | H | $C\equiv CCH_2CH_3$ |
| 5X.014 | H | $C\equiv CCH(Me)F$ |
| 5X.015 | H | $C\equiv CCF_2Me$ |
| 5X.016 | H | $C\equiv CCH_2CF_3$ |
| 5X.017 | H | $C\equiv CC_2F_5$ |
| 5X.018 | H | $C\equiv CCF{=}CF_2$ |
| 5X.019 | H | $C\equiv CCH_2CH_2CH_3$ |
| 5X.020 | H | $C\equiv CCHFCH_2CH_3$ |
| 5X.021 | H | $C\equiv CCF_2CH_2CH_3$ |
| 5X.022 | H | $C\equiv CCH(Me)_2$ |
| 5X.023 | H | $C\equiv CCMe_2OMe$ |
| 5X.024 | H | $C\equiv CC(Me)_2F$ |
| 5X.025 | H | $C\equiv CCF(CF_3)_2$ |
| 5X.026 | H | $C\equiv CC(Me){=}CH_2$ |
| 5X.027 | H | $C\equiv C$(cyclopropyl) |
| 5X.028 | H | $C\equiv CCH_2CH(Me)_2$ |
| 5X.029 | H | $C\equiv CCH(Me)CH_2CH_3$ |
| 5X.030 | H | $C\equiv CCMe_3$ |
| 5X.031 | H | $C\equiv CSiMe_3$ |
| 5X.032 | H | $C\equiv CCH_2C(Me)_3$ |
| 5X.033 | H | $C\equiv CCH_2SiMe_3$ |
| 5X.034 | H | $C\equiv C$(1-F-cyclopentyl) |
| 5X.035 | H | $C\equiv CSi(Me_2)CMe_3$ |
| 5X.036 | H | $CH_2C\equiv CH$ |
| 5X.037 | H | $CHFC\equiv CH$ |
| 5X.038 | H | $CF_2C\equiv CH$ |
| 5X.039 | H | $CHMeC\equiv CH$ |
| 5X.040 | H | $CH(CF_3)C\equiv CH$ |
| 5X.041 | H | $CMe_2C\equiv CH$ |
| 5X.042 | H | $CH_2C\equiv CMe$ |
| 5X.043 | H | $CF_2C\equiv CMe$ |
| 5X.044 | H | $CH_2C\equiv CCF_3$ |
| 5X.045 | H | $CF_2C\equiv CCF_3$ |
| 5X.046 | H | $CH_2C\equiv CCMe_3$ |
| 5X.047 | H | $CF_2C\equiv CCMe_3$ |
| 5X.048 | H | $CH_2C\equiv CSiMe_3$ |
| 5X.049 | H | $CF_2C\equiv CSiMe_3$ |
| 5X.050 | H | $CH{=}CH_2$ |
| 5X.051 | H | $CH{=}CHF$ |
| 5X.052 | H | $CH{=}CHCl$ |
| 5X.053 | H | $CH{=}CHBr$ |
| 5X.054 | H | $CH{=}CF_2$ |
| 5X.055 | H | $CH{=}CFCl$ |
| 5X.056 | H | $CH{=}CFBr$ |
| 5X.057 | H | $CH{=}CCl_2$ |
| 5X.058 | H | $CH{=}CBr_2$ |
| 5X.059 | H | $CF{=}CH_2$ |
| 5X.060 | H | $CF{=}CHF$ |
| 5X.061 | H | $CF{=}CF_2$ |
| 5X.062 | H | $CF{=}CFCl$ |
| 5X.063 | H | $CF{=}CFBr$ |
| 5X.064 | H | $CF{=}CCl_2$ |
| 5X.065 | H | $CCl{=}CH_2$ |
| 5X.066 | H | $CCl{=}CF_2$ |
| 5X.067 | H | $CBr{=}CH_2$ |
| 5X.068 | H | $CBr{=}CF_2$ |
| 5X.069 | H | $CH{=}CHCF_3$ |
| 5X.070 | H | $CH{=}CFCF_3$ |
| 5X.071 | H | $CH{=}CClCF_3$ |
| 5X.072 | H | $CH{=}CBrCF_3$ |
| 5X.073 | H | $CH{=}CFCF_2Cl$ |
| 5X.074 | H | $CH{=}CClCF_2Cl$ |
| 5X.075 | H | $CF{=}CHCF_3$ |
| 5X.076 | H | $CF{=}CFCF_3$ |

TABLE 5-continued

| Compound No. | $R^1$ | $R^6$ |
|---|---|---|
| 5X.077 | H | $CH{=}CHC_2F_5$ |
| 5X.078 | H | $CH{=}CFC_2F_5$ |
| 5X.079 | H | $CH{=}CClC_2F_5$ |
| 5X.080 | H | $CH{=}C(CF_3)_2$ |
| 5X.081 | H | $CF{=}C(CF_3)_2$ |
| 5X.082 | H | $CH{=}CHSiMe_3$ |
| 5X.083 | H | $CMe{=}CF_2$ |
| 5X.084 | H | $CMe{=}CFCl$ |
| 5X.085 | H | $CMe{=}CFBr$ |
| 5X.086 | H | $CMe{=}CCl_2$ |
| 5X.087 | H | $CMe{=}CBr_2$ |
| 5X.088 | H | $CMe{=}CHCF_3$ |
| 5X.089 | H | $CMe{=}CFCF_3$ |
| 5X.090 | H | $CMe{=}CClCF_3$ |
| 5X.091 | H | $CCF_3{=}CH_2$ |
| 5X.092 | H | $CCF_3{=}CHF$ |
| 5X.093 | H | $CCF_3{=}CHCl$ |
| 5X.094 | H | $CCF_3{=}CF_2$ |
| 5X.095 | H | $CCF_3{=}CCl_2$ |
| 5X.096 | H | $CCF_3{=}CBr_2$ |
| 5X.097 | H | $CH_2CH{=}CF_2$ |
| 5X.098 | H | $CH_2CH{=}CCl_2$ |
| 5X.099 | H | $CH_2CF{=}CF_2$ |
| 5X.100 | H | $CH_2CF{=}CCl_2$ |

Table 5a provides 100 compounds of formula (II.a):

(II.a)

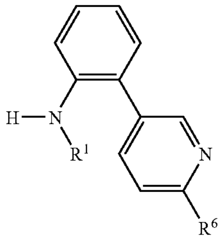

wherein $R^1$ and $R^6$ are as defined in Table 5a.

Table 5b provides 100 compounds of formula (II.b):

(II.b)

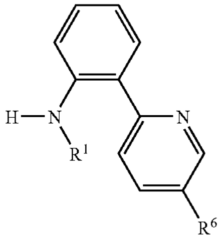

wherein $R^1$ and $R^6$ are as defined in Table 5b.

Table 5c provides 100 compounds of formula (II.c)

(II.c)

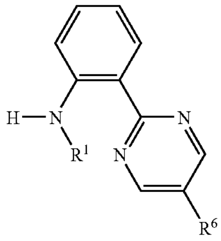

wherein $R^1$ and $R^6$ are as defined in Table 5c.

Table 5d provides 100 compounds of formula (II.d)

(II.d)

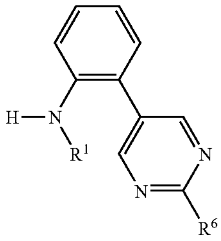

wherein $R^1$ and $R^6$ are as defined in Table 5d.

Table 5e provides 100 compounds of formula (II.e)

(II.e)

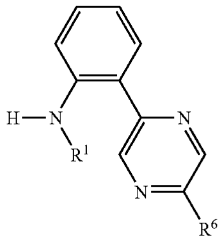

wherein $R^1$ and $R^6$ are as defined in Table 5e.

Table 5f provides 100 compounds of formula (II.f)

(II.f)

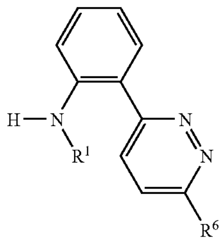

wherein $R^1$ and $R^6$ are as defined in Table 5f.

Table 5g provides 100 compounds of formula (II.g)

(II.g)

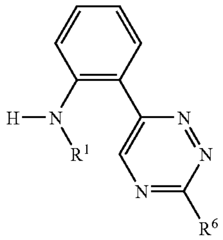

wherein $R^1$ and $R^6$ are as defined in Table 5g.

Table 5h provides 100 compounds of formula (II.h)

(II.h)

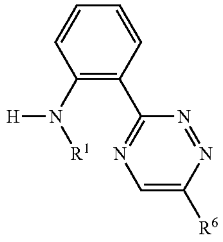

wherein $R^1$ and $R^6$ are as defined in Table 5h.

Table 5i provides 100 compounds of formula (II.i)

(II.i)

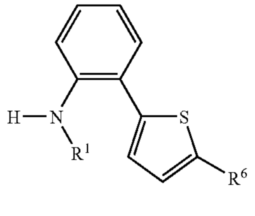

wherein $R^1$ and $R^6$ are as defined in Table 5i.

Table 5j provides 100 compounds of formula (II.j)

(II.j)

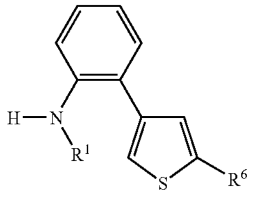

wherein $R^1$ and $R^6$ are as defined in Table 5j.

Table 5k provides 100 compounds of formula (II.k)

(II.k)

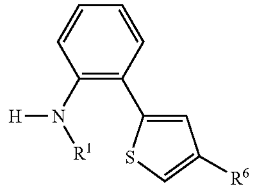

wherein $R^1$ and $R^6$ are as defined in Table 5k.

Table 5l provides 100 compounds of formula (II.l)

(II.l)

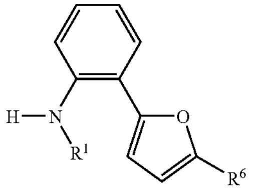

wherein $R^1$ and $R^6$ are as defined in Table 5l.

Table 5m provides 100 compounds of formula (II.m)

(II.m)

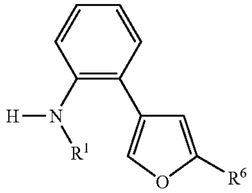

wherein $R^1$ and $R^6$ are as defined in Table 5m.

Table 5n provides 100 compounds of formula (II.n)

(II.n)

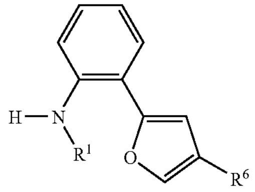

wherein $R^1$ and $R^6$ are as defined in Table 5n.

Table 5o provides 100 compounds of formula (II.o)

(II.o)

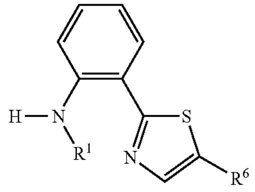

wherein $R^1$ and $R^6$ are as defined in Table 5o.

Table 5p provides 100 compounds of formula (II.p)

(II.p)

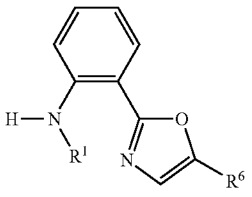

wherein $R^1$ and $R^6$ are as defined in Table 5p.

Table 5q provides 100 compounds of formula (II.q)

(II.q)

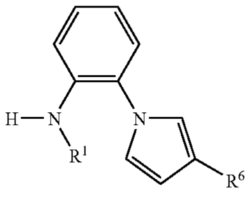

wherein $R^1$ and $R^6$ are as defined in Table 5q.

Table 5r provides 100 compounds of formula (II.r)

(II.r)

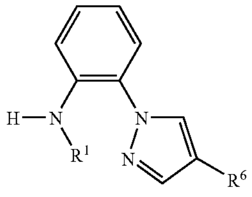

wherein $R^1$ and $R^6$ are as defined in Table 5r.

Table 5s provides 100 compounds of formula (II.s)

(II.s)

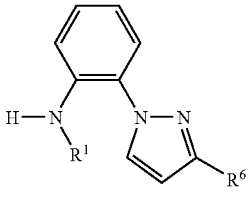

wherein $R^1$ and $R^6$ are as defined in Table 5s.

Table 5t provides 100 compounds of formula (II.t)

(II.t)

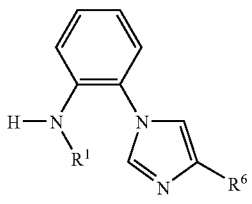

wherein $R^1$ and $R^6$ are as defined in Table 5t.

Table 5u provides 100 compounds of formula (II.u)

(II.u)

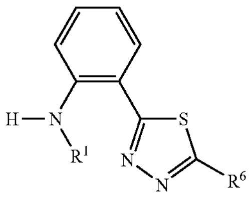

wherein $R^1$ and $R^6$ are as defined in Table 5u.

Table 5v provides 100 compounds of formula (II.v)

(II.v)

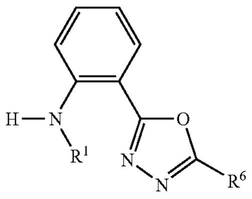

wherein $R^1$ and $R^6$ are as defined in Table 5v.

Table 5w provides 100 compounds of formula (II.w)

(II.w)

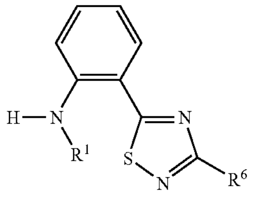

wherein $R^1$ and $R^6$ are as defined in Table 5w.

Table 5x provides 100 compounds of formula (II.x)

(II.x)

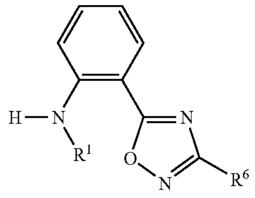

wherein $R^1$ and $R^6$ are as defined in Table 5x.

Table 6X represents Table 6a (when X is a), represents Table 6b (when X is b), represents Table 6c (when X is c), represents Table 6d (when X is d), represents Table 6e (when X is e), represents Table 6f (when X is f), represents Table 6g (when X is g), represents Table 6h (when X is h), represents Table 6i (when X is i), represents Table 6j (when X is j), represents Table 6k (when X is k), represents Table 6l (when X is l), represents Table 6m (when X is m), represents Table 6n (when X is n), represents Table 6o (when X is o), represents Table 6p (when X is p), represents Table 6q (when X is q), represents Table 6r (when X is r), represents Table 6s (when X is s), represents Table 6t (when X is t), represents Table 6u (when X is u), represents Table 6v (when X is v), represents Table 6w (when X is w) and represents Table 6x (when X is x).

TABLE 6

| Compound No. | $R^6$ |
|---|---|
| 6X.001 | $C\equiv CH$ |
| 6X.002 | $C\equiv CF$ |
| 6X.003 | $C\equiv CCl$ |
| 6X.004 | $C\equiv CBr$ |
| 6X.005 | $C\equiv CMe$ |
| 6X.006 | $C\equiv CCH_2OMe$ |
| 6X.007 | $C\equiv CCH_2F$ |
| 6X.008 | $C\equiv CCF_2H$ |
| 6X.009 | $C\equiv CCHFCl$ |
| 6X.010 | $C\equiv CCF_2Cl$ |
| 6X.011 | $C\equiv CCF_2Br$ |
| 6X.012 | $C\equiv CCF_3$ |
| 6X.013 | $C\equiv CCH_2CH_3$ |
| 6X.014 | $C\equiv CCH(Me)F$ |
| 6X.015 | $C\equiv CCF_2Me$ |
| 6X.016 | $C\equiv CCH_2CF_3$ |
| 6X.017 | $C\equiv CC_2F_5$ |
| 6X.018 | $C\equiv CCF{=}CF_2$ |
| 6X.019 | $C\equiv CCH_2CH_2CH_3$ |
| 6X.020 | $C\equiv CCHFCH_2CH_3$ |
| 6X.021 | $C\equiv CCF_2CH_2CH_3$ |
| 6X.022 | $C\equiv CCH(Me)_2$ |
| 6X.023 | $C\equiv CCMe_2OMe$ |
| 6X.024 | $C\equiv CC(Me)_2F$ |
| 6X.025 | $C\equiv CCF(CF_3)_2$ |
| 6X.026 | $C\equiv CC(Me){=}CH_2$ |
| 6X.027 | $C\equiv C$(cyclopropyl) |
| 6X.028 | $C\equiv CCH_2CH(Me)_2$ |
| 6X.029 | $C\equiv CCH(Me)CH_2CH_3$ |
| 6X.030 | $C\equiv CCMe_3$ |
| 6X.031 | $C\equiv CSiMe_3$ |
| 6X.032 | $C\equiv CCH_2C(Me)_3$ |
| 6X.033 | $C\equiv CCH_2SiMe_3$ |
| 6X.034 | $C\equiv C$(1-F-cyclopentyl) |
| 6X.035 | $C\equiv CSi(Me_2)CMe_3$ |
| 6X.036 | $CH_2C\equiv CH$ |
| 6X.037 | $CHFC\equiv CH$ |
| 6X.038 | $CF_2C\equiv CH$ |
| 6X.039 | $CHMeC\equiv CH$ |
| 6X.040 | $CH(CF_3)C\equiv CH$ |
| 6X.041 | $CMe_2C\equiv CH$ |
| 6X.042 | $CH_2C\equiv CMe$ |
| 6X.043 | $CF_2C\equiv CMe$ |
| 6X.044 | $CH_2C\equiv CCF_3$ |
| 6X.045 | $CF_2C\equiv CCF_3$ |
| 6X.046 | $CH_2C\equiv CCMe_3$ |
| 6X.047 | $CF_2C\equiv CCMe_3$ |
| 6X.048 | $CH_2C\equiv CSiMe_3$ |
| 6X.049 | $CF_2C\equiv CSiMe_3$ |
| 6X.050 | $CH{=}CH_2$ |
| 6X.051 | $CH{=}CHF$ |
| 6X.052 | $CH{=}CHCl$ |
| 6X.053 | $CH{=}CHBr$ |
| 6X.054 | $CH{=}CF_2$ |
| 6X.055 | $CH{=}CFCl$ |
| 6X.056 | $CH{=}CFBr$ |
| 6X.057 | $CH{=}CCl_2$ |
| 6X.058 | $CH{=}CBr_2$ |
| 6X.059 | $CF{=}CH_2$ |
| 6X.060 | $CF{=}CHF$ |
| 6X.061 | $CF{=}CF_2$ |
| 6X.062 | $CF{=}CFCl$ |
| 6X.063 | $CF{=}CFBr$ |
| 6X.064 | $CF{=}CCl_2$ |
| 6X.065 | $CCl{=}CH_2$ |
| 6X.066 | $CCl{=}CF_2$ |
| 6X.067 | $CBr{=}CH_2$ |
| 6X.068 | $CBr{=}CF_2$ |
| 6X.069 | $CH{=}CHCF_3$ |
| 6X.070 | $CH{=}CFCF_3$ |
| 6X.071 | $CH{=}CClCF_3$ |

TABLE 6-continued

| Compound No. | $R^6$ |
|---|---|
| 6X.072 | $CH{=}CBrCF_3$ |
| 6X.073 | $CH{=}CFCF_2Cl$ |
| 6X.074 | $CH{=}CClCF_2Cl$ |
| 6X.075 | $CF{=}CHCF_3$ |
| 6X.076 | $CF{=}CFCF_3$ |
| 6X.077 | $CH{=}CHC_2F_5$ |
| 6X.078 | $CH{=}CFC_2F_5$ |
| 6X.079 | $CH{=}CClC_2F_5$ |
| 6X.080 | $CH{=}C(CF_3)_2$ |
| 6X.081 | $CF{=}C(CF_3)_2$ |
| 6X.082 | $CH{=}CHSiMe_3$ |
| 6X.083 | $CMe{=}CF_2$ |
| 6X.084 | $CMe{=}CFCl$ |
| 6X.085 | $CMe{=}CFBr$ |
| 6X.086 | $CMe{=}CCl_2$ |
| 6X.087 | $CMe{=}CBr_2$ |
| 6X.088 | $CMe{=}CHCF_3$ |
| 6X.089 | $CMe{=}CFCF_3$ |
| 6X.090 | $CMe{=}CClCF_3$ |
| 6X.091 | $CCF_3{=}CH_2$ |
| 6X.092 | $CCF_3{=}CHF$ |
| 6X.093 | $CCF_3{=}CHCl$ |
| 6X.094 | $CCF_3{=}CF_2$ |
| 6X.095 | $CCF_3{=}CCl_2$ |
| 6X.096 | $CCF_3{=}CBr_2$ |
| 6X.097 | $CH_2CH{=}CF_2$ |
| 6X.098 | $CH_2CH{=}CCl_2$ |
| 6X.099 | $CH_2CF{=}CF_2$ |
| 6X.100 | $CH_2CF{=}CCl_2$ |

Table 6a provides 100 compounds of formula (III.a):

(III.a)

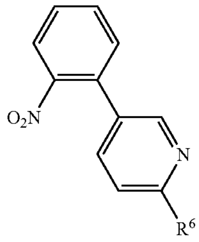

wherein $R^6$ is as defined in Table 6a.

Table 6b provides 100 compounds of formula (III.b):

(III.b)

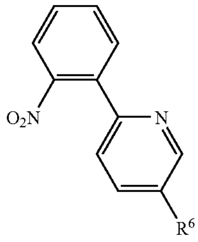

wherein $R^6$ is as defined in Table 6b.

Table 6c provides 100 compounds of formula (III.c)

(III.c)

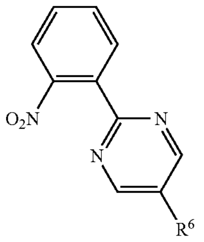

wherein $R^6$ is as defined in Table 6c.

Table 6d provides 100 compounds of formula (III.d)

(III.d)

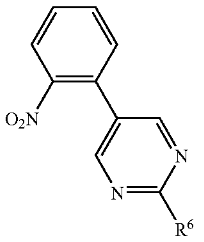

wherein $R^6$ is as defined in Table 6d.

Table 6e provides 100 compounds of formula (III.e)

(III.e)

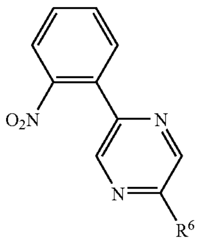

wherein $R^6$ is as defined in Table 6e.

Table 6f provides 100 compounds of formula (III.f)

(III.f)

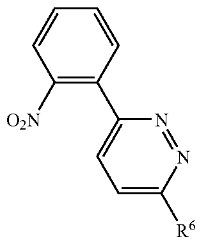

wherein $R^6$ is as defined in Table 6f.

Table 6g provides 100 compounds of formula (III.g)

(III.g)

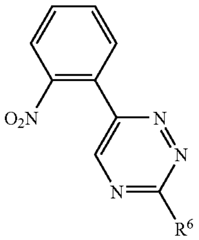

wherein $R^6$ is as defined in Table 6g.

Table 6h provides 100 compounds of formula (III.h)

(III.h)

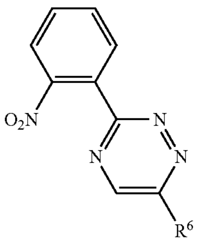

wherein $R^6$ is as defined in Table 6h.

Table 6i provides 100 compounds of formula (III.i)

(III.i)

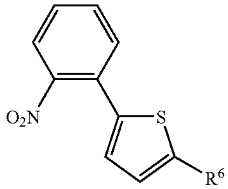

wherein $R^6$ is as defined in Table 6i.

Table 6j provides 100 compounds of formula (III.j)

(III.j)

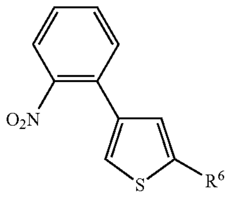

wherein $R^6$ is as defined in Table 6j.

Table 6k provides 100 compounds of formula (III.k)

(III.k)

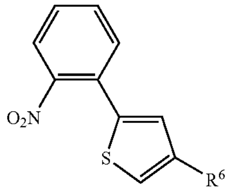

wherein $R^6$ is as defined in Table 6k.

Table 6l provides 100 compounds of formula (III.l)

(III.l)

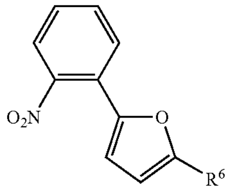

wherein $R^6$ is as defined in Table 6l.

Table 6m provides 100 compounds of formula (III.m)

(III.m)

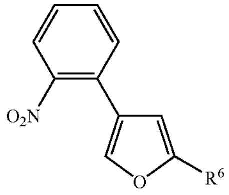

wherein $R^6$ is as defined in Table 6m.

Table 6n provides 100 compounds of formula (III.n)

(III.n)

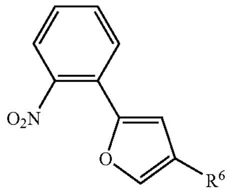

wherein $R^6$ is as defined in Table 6n.

Table 6o provides 100 compounds of formula (III.o)

(III.o)

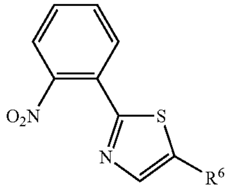

wherein $R^6$ is as defined in Table 6o.

Table 6p provides 100 compounds of formula (III.p)

(III.p)

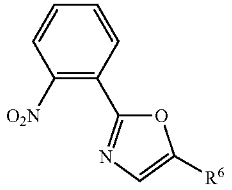

wherein $R^6$ is as defined in Table 6p.

Table 6q provides 100 compounds of formula (III.q)

(III.q)

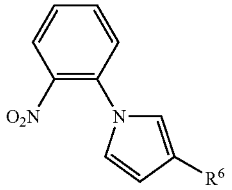

wherein $R^6$ is as defined in Table 6q.

Table 6r provides 100 compounds of formula (III.r)

(III.r)

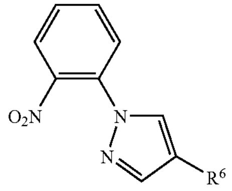

wherein $R^6$ is as defined in Table 6r.

Table 6s provides 100 compounds of formula (III.s)

(III.s)

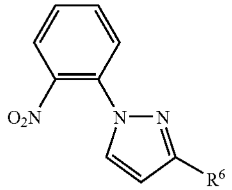

wherein $R^6$ is as defined in Table 6s.

Table 6t provides 100 compounds of formula (III.t)

(III.t)

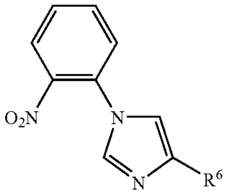

wherein $R^6$ is as defined in Table 6t.

Table 6u provides 100 compounds of formula (III.u)

(III.u)

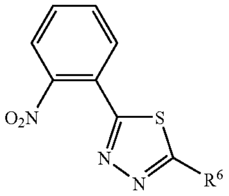

wherein $R^6$ is as defined in Table 6u.

Table 6v provides 100 compounds of formula (III.v)

(III.v)

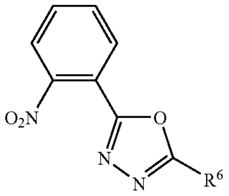

wherein $R^6$ is as defined in Table 6v.

Table 6w provides 100 compounds of formula (III.w)

(III.w)

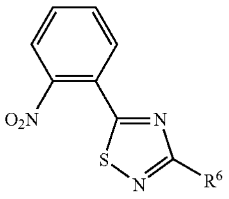

wherein $R^6$ is as defined in Table 6w.

Table 6x provides 100 compounds of formula (III.x)

(III.x)

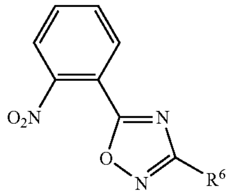

wherein $R^6$ is as defined in Table 6x.

Table 7X represents Table 7a (when X is a), represents Table 7b (when X is b), represents Table 7c (when X is c), represents Table 7d (when X is d), represents Table 7e (when X is e), represents Table 7f (when X is f), represents Table 7g (when X is g), represents Table 7h (when X is h), represents Table 7i (when X is i), represents Table 7j (when X is j), represents Table 7k (when X is k), represents Table 7l (when X is l), represents Table 7m (when X is m), represents Table 7n (when X is n), represents Table 7o (when X is o), represents Table 7p (when X is p), represents Table 7q (when X is q), represents Table 7r (when X is r), represents Table 7s (when X is s), represents Table 7t (when X is t), represents Table 7u (when X is u), represents Table 7v (when X is v), represents Table 7w (when X is w) and represents Table 7x (when X is x).

TABLE 7

| Compound Set No. | $R^6$ |
|---|---|
| 7X.001 | $C\equiv CH$ |
| 7X.002 | $C\equiv CF$ |
| 7X.003 | $C\equiv CCl$ |
| 7X.004 | $C\equiv CBr$ |
| 7X.005 | $C\equiv CMe$ |
| 7X.006 | $C\equiv CCH_2OMe$ |
| 7X.007 | $C\equiv CCH_2F$ |
| 7X.008 | $C\equiv CCF_2H$ |
| 7X.009 | $C\equiv CCHFCl$ |
| 7X.010 | $C\equiv CCF_2Cl$ |
| 7X.011 | $C\equiv CCF_2Br$ |
| 7X.012 | $C\equiv CCF_3$ |
| 7X.013 | $C\equiv CCH_2CH_3$ |
| 7X.014 | $C\equiv CCH(Me)F$ |
| 7X.015 | $C\equiv CCF_2Me$ |
| 7X.016 | $C\equiv CCH_2CF_3$ |
| 7X.017 | $C\equiv CC_2F_5$ |
| 7X.018 | $C\equiv CCF{=}CF_2$ |
| 7X.019 | $C\equiv CCH_2CH_2CH_3$ |
| 7X.020 | $C\equiv CCHFCH_2CH_3$ |
| 7X.021 | $C\equiv CCF_2CH_2CH_3$ |
| 7X.022 | $C\equiv CCH(Me)_2$ |
| 7X.023 | $C\equiv CCMe_2OMe$ |
| 7X.024 | $C\equiv CC(Me)_2F$ |
| 7X.025 | $C\equiv CCF(CF_3)_2$ |
| 7X.026 | $C\equiv CC(Me){=}CH_2$ |
| 7X.027 | $C\equiv C$(cyclopropyl) |
| 7X.028 | $C\equiv CCH_2CH(Me)_2$ |
| 7X.029 | $C\equiv CCH(Me)CH_2CH_3$ |
| 7X.030 | $C\equiv CCMe_3$ |
| 7X.031 | $C\equiv CSiMe_3$ |
| 7X.032 | $C\equiv CCH_2C(Me)_3$ |
| 7X.033 | $C\equiv CCH_2SiMe_3$ |
| 7X.034 | $C\equiv C$(1-F-cyclopentyl) |
| 7X.035 | $C\equiv CSi(Me_2)CMe_3$ |
| 7X.036 | $CH_2C\equiv CH$ |
| 7X.037 | $CHFC\equiv CH$ |
| 7X.038 | $CF_2C\equiv CH$ |
| 7X.039 | $CHMeC\equiv CH$ |
| 7X.040 | $CH(CF_3)C\equiv CH$ |

TABLE 7-continued

| Compound Set No. | $R^6$ |
|---|---|
| 7X.041 | $CMe_2C\equiv CH$ |
| 7X.042 | $CH_2C\equiv CMe$ |
| 7X.043 | $CF_2C\equiv CMe$ |
| 7X.044 | $CH_2C\equiv CCF_3$ |
| 7X.045 | $CF_2C\equiv CCF_3$ |
| 7X.046 | $CH_2C\equiv CCMe_3$ |
| 7X.047 | $CF_2C\equiv CCMe_3$ |
| 7X.048 | $CH_2C\equiv CSiMe_3$ |
| 7X.049 | $CF_2C\equiv CSiMe_3$ |
| 7X.050 | $CH=CH_2$ |
| 7X.051 | $CH=CHF$ |
| 7X.052 | $CH=CHCl$ |
| 7X.053 | $CH=CHBr$ |
| 7X.054 | $CH=CF_2$ |
| 7X.055 | $CH=CFCl$ |
| 7X.056 | $CH=CFBr$ |
| 7X.057 | $CH=CCl_2$ |
| 7X.058 | $CH=CBr_2$ |
| 7X.059 | $CF=CH_2$ |
| 7X.060 | $CF=CHF$ |
| 7X.061 | $CF=CF_2$ |
| 7X.062 | $CF=CFCl$ |
| 7X.063 | $CF=CFBr$ |
| 7X.064 | $CF=CCl_2$ |
| 7X.065 | $CCl=CH_2$ |
| 7X.066 | $CCl=CF_2$ |
| 7X.067 | $CBr=CH_2$ |
| 7X.068 | $CBr=CF_2$ |
| 7X.069 | $CH=CHCF_3$ |
| 7X.070 | $CH=CFCF_3$ |
| 7X.071 | $CH=CClCF_3$ |
| 7X.072 | $CH=CBrCF_3$ |
| 7X.073 | $CH=CFCF_2Cl$ |
| 7X.074 | $CH=CClCF_2Cl$ |
| 7X.075 | $CF=CHCF_3$ |
| 7X.076 | $CF=CFCF_3$ |
| 7X.077 | $CH=CHC_2F_5$ |
| 7X.078 | $CH=CFC_2F_5$ |
| 7X.079 | $CH=CClC_2F_5$ |
| 7X.080 | $CH=C(CF_3)_2$ |
| 7X.081 | $CF=C(CF_3)_2$ |
| 7X.082 | $CH=CHSiMe_3$ |
| 7X.083 | $CMe=CF_2$ |
| 7X.084 | $CMe=CFCl$ |
| 7X.085 | $CMe=CFBr$ |
| 7X.086 | $CMe=CCl_2$ |
| 7X.087 | $CMe=CBr_2$ |
| 7X.088 | $CMe=CHCF_3$ |
| 7X.089 | $CMe=CFCF_3$ |
| 7X.090 | $CMe=CClCF_3$ |
| 7X.091 | $CCF_3=CH_2$ |
| 7X.092 | $CCF_3=CHF$ |
| 7X.093 | $CCF_3=CHCl$ |
| 7X.094 | $CCF_3=CF_2$ |
| 7X.095 | $CCF_3=CCl_2$ |
| 7X.096 | $CCF_3=CBr_2$ |
| 7X.097 | $CH_2CH=CF_2$ |
| 7X.098 | $CH_2CH=CCl_2$ |
| 7X.099 | $CH_2CF=CF_2$ |
| 7X.100 | $CH_2CF=CCl_2$ |

Table 7a provides 300 compounds of formula (IV.a):

(IV.a)

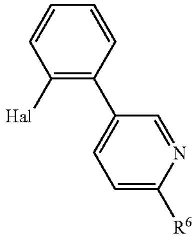

wherein $R^6$ is as defined in Table 7a and Hal is bromo, chloro or iodo. For example, table 7a discloses as compound set no. 7a.001 the following set of three compounds:

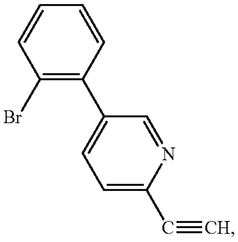

,

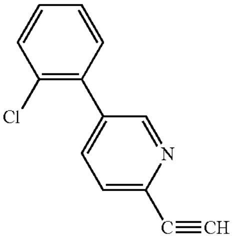

and

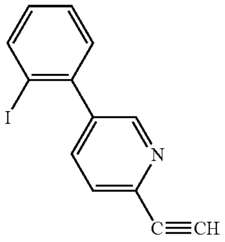

Table 7b provides 300 compounds of formula (IV.b):

(IV.b)

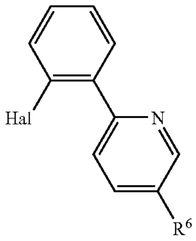

wherein $R^6$ is as defined in Table 7b and Hal is bromo, chloro or iodo.

Table 7c provides 300 compounds of formula (IV.c)

(IV.c)

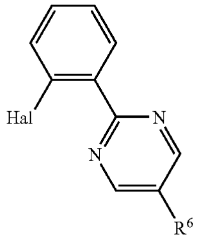

wherein $R^6$ is as defined in Table 7c and Hal is bromo, chloro or iodo.

Table 7d provides 300 compounds of formula (IV.d)

(IV.d)

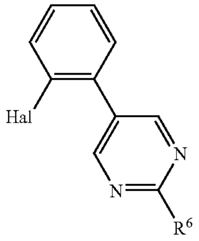

wherein $R^6$ is as defined in Table 7d and Hal is bromo, chloro or iodo.

Table 7e provides 300 compounds of formula (IV.e)

(IV.e)

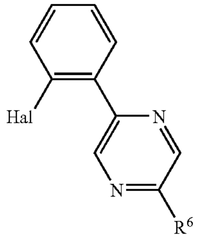

wherein $R^6$ is as defined in Table 7e and Hal is bromo, chloro or iodo.

Table 7f provides 300 compounds of formula (IV.f)

(IV.f)

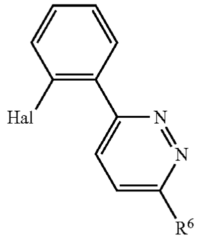

wherein $R^6$ is as defined in Table 7f and Hal is bromo, chloro or iodo.

Table 7g provides 300 compounds of formula (IV.g)

(IV.g)

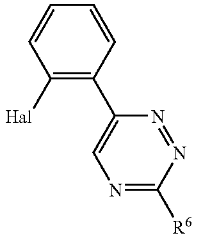

wherein $R^6$ is as defined in Table 7g and Hal is bromo, chloro or iodo.

Table 7h provides 300 compounds of formula (IV.h)

(IV.h)

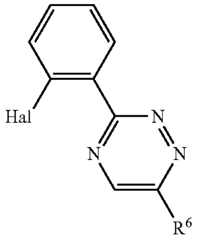

wherein $R^6$ is as defined in Table 7h and Hal is bromo, chloro or iodo.

Table 7i provides 300 compounds of formula (IV.i)

(IV.i)

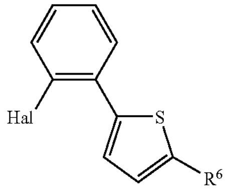

wherein $R^6$ is as defined in Table 7i and Hal is bromo, chloro or iodo.

Table 7j provides 300 compounds of formula (IV.j)

(IV.j)

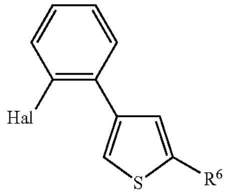

wherein $R^6$ is as defined in Table 7j and Hal is bromo, chloro or iodo.

Table 7k provides 300 compounds of formula (IV.k)

(IV.k)

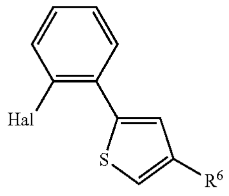

wherein $R^6$ is as defined in Table 7k and Hal is bromo, chloro or iodo.

Table 7l provides 300 compounds of formula (IV.l)

(IV.l)

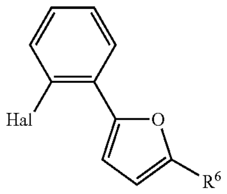

wherein $R^6$ is as defined in Table 7l and Hal is bromo, chloro or iodo.

Table 7m provides 300 compounds of formula (IV.m)

(IV.m)

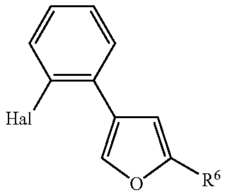

wherein $R^6$ is as defined in Table 7m and Hal is bromo, chloro or iodo.

Table 7n provides 300 compounds of formula (IV.n)

(IV.n)

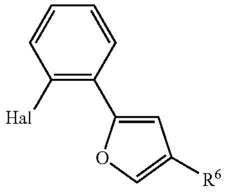

wherein $R^6$ is as defined in Table 7n and Hal is bromo, chloro or iodo.

Table 7o provides 300 compounds of formula (IV.o)

(IV.o)

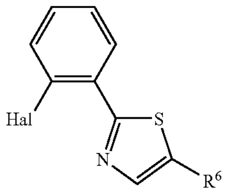

wherein $R^6$ is as defined in Table 7o and Hal is bromo, chloro or iodo.

Table 7p provides 300 compounds of formula (IV.p)

(IV.p)

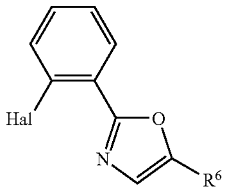

wherein $R^6$ is as defined in Table 7p and Hal is bromo, chloro or iodo.

Table 7q provides 300 compounds of formula (IV.q)

(IV.q)

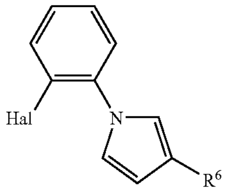

wherein $R^6$ is as defined in Table 7q and Hal is bromo, chloro or iodo.

Table 7r provides 300 compounds of formula (IV.r)

(IV.r)

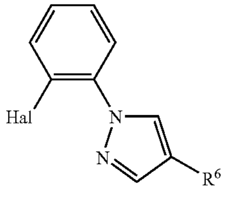

wherein $R^6$ is as defined in Table 7r and Hal is bromo, chloro or iodo.

Table 7s provides 300 compounds of formula (IV.s)

(IV.s)

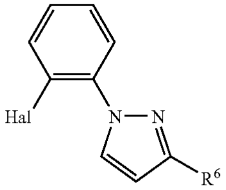

wherein $R^6$ is as defined in Table 7s and Hal is bromo, chloro or iodo.

Table 7t provides 300 compounds of formula (IV.t)

(IV.t)

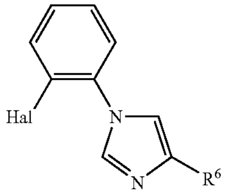

wherein $R^6$ is as defined in Table 7t and Hal is bromo, chloro or iodo.

Table 7u provides 300 compounds of formula (IV.u)

(IV.u)

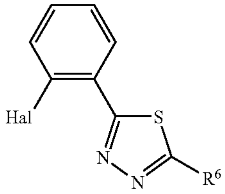

wherein $R^6$ is as defined in Table 7u and Hal is bromo, chloro or iodo.

Table 7v provides 300 compounds of formula (IV.v)

(IV.v)

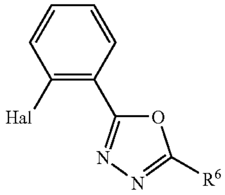

wherein $R^6$ is as defined in Table 7v and Hal is bromo, chloro or iodo.

Table 7w provides 300 compounds of formula (IV.w)

(IV.w)

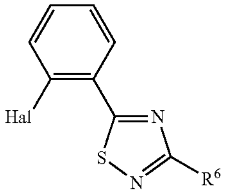

wherein $R^6$ is as defined in Table 7w and Hal is bromo, chloro or iodo.

Table 7x provides 300 compounds of formula (IV.x)

(IV.x)

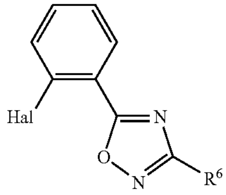

wherein $R^6$ is as defined in Table 7x and Hal is bromo, chloro or iodo.

Throughout this description, temperatures are given in degrees Celsius; "NMR" means nuclear magnetic resonance spectrum; and "%" is percent by weight, unless corresponding concentrations are indicated in other units.

The following abbreviations are used throughout this description:

m.p.=melting point b.p.=boiling point.

s=singlet br=broad d=doublet dd=doublet of doublets t=triplet q=quartet m=multiplet ppm=parts per million Table 8 shows selected melting point and selected NMR data, all with $CDCl_3$ as the solvent (unless otherwise stated, no attempt is made to list all characterising data in all cases) for compounds of Tables 1aa to 1ax, Tables 2aa to 2ax, Tables 3aa to 3ax, Tables 4aa to 4ax, Tables 5a to 5x, Tables 6a to 6x and Tables 7a to 7x. Unless otherwise stated, the data relate to a cis/trans mixture of each compound.

TABLE 8

| Compound Number | $^1$H-NMR data (ppm/multiplicity/number of Hs) | m.p. (° C.) |
|---|---|---|
| 1aa.098 | | 203-205 |
| 1aa.099 | | 204-206 |
| 1ab.098 | | 161-162 |
| 1ab.099 | | 195-197 |
| 1ai.077 | | 158-164 |
| 1ai.078 | | 134-137 |
| 1ai.080 | | 63-66 |
| 1ai.081 | | 150-162 |
| 1ai.098 | | 122-125 |
| 1al.098 | | 102-106 |
| 1ai.099 | | 138-141 |
| 1aj.099 | | 135-139 |
| 1al.099 | | 164-165 |
| 1ar.099 | | 145-148 |
| 2bi.098 | | 160-161 |

TABLE 8-continued

| Compound Number | $^1$H-NMR data (ppm/multiplicity/number of Hs) | m.p. (° C.) |
|---|---|---|
| 2br.098 | 1.24 (s, 9H), 3.66 (s, 3H), 6.89-7.32 (m, 5H), 7.76 (d, 2H), 8.49 (d, 1H). | |
| 3cb.098 | | 185-186 |
| 3ci.098 | 1.26 (s, 9H), 2X.67 (s, 3H), 6.84 (d, 1H), 7.05 (d, 1H), 7.12-7.49 (m, 4H) | |
| 3cr.098 | 1.24 (s, 9H), 2.71 (s, 3H), 7.13-7.82 (m, 6H) | |
| 4da.098 | | 210-212 |
| 4db.098 | | 151-152 |
| 4di.098 | 1.28 (s, 9H), 6.89 (d, 1H), 7.03 (d, 1H), 7.14-7.40 (m, 4H), 8.10 (d, 1H), 8.36-8.43 (m, 2H) | |
| 4dr.098 | | 160-163 |
| 5i.030 | 1.27 (s, 9H), 3.95 (br.s, 2H), 6.67-7.18 (m, 6H) | |
| 5j.030 | 1.38 (s, 9H), 3.96 (br.s, 2H), 6.88-7.57 (m, 6H) | |
| 5l.030 | 1.27 (s, 9H), 4.30 (br.s, 2H), 6.44 (d, 1H), 6.51 (d, 1H), 6.63-7.39 (m, 4H) | |
| 5r.030 | 1.28 (s, 9H), 4.56 (br.s, 2H), 6.68-7.11 (m, 4H), 7.69 (d, 2H) | |
| 6i.030 | 1.25 (s, 9H), 6.83 (d, 1H), 6.98 (d, 1H), 7.33-7.67 (m, 4H) | |
| 6j.030 | 1.42 (s, 9H), 7.22 (d, 1H), 7.33-8.22 (m, 5H) | |
| 6l.030 | 1.34 (s, 9H), 6.54 (d, 1H), 6.60 (d, 1H), 7.36-7.80 (m, 4H) | |
| 6r.030 | 1.26 (s, 9H), 7.42-7.81 (m, 6H) | |

The compounds according to the present invention may be prepared according to the following reaction schemes, in which, unless otherwise stated, the definition of each variable is as defined above for a compound of formula (I).

There are a number of alternative methods for preparing a compound of formula (I).

Method A

A compound of formula (I) may be prepared by reacting a compound of formula (II) with a compound of formula $Het^1$-C(═O)OR' [where R' is $C_{1-5}$ alkyl] in the presence of a strong base [for example NaH or sodium hexamethyldisilazane], in a dry polar solvent [preferably THF] and at a temperature between −10° C. and the boiling point of the solvent [preferably at ambient temperature]. The article by J. Wang et al, Synlett 2001, 1485 provides details of analogous preparations.

Method B

A compound of formula (I) may be prepared by reacting a compound of formula (II) with a compound of formula $Het^1$-C(═O)R" [where R" is OH or a leaving group, such as Cl, Br, F or OC(═O)$C_{1-4}$ alkyl] in an inert organic solvent [such as ethylacetate, dichloromethane, dioxane or DMF] and at a temperature between −10° C. and the boiling point of the solvent [preferably at ambient temperature]. If R" is OH, the reaction is carried out in the presence of an activating agent [for example BOP—Cl] and two equivalents of a base [such as a tertiary amine, an inorganic carbonate or a hydrogen carbonate]. Alternatively, if R" is a leaving group, the reaction is carried out in the presence of at least one equivalent of base [such as pyridine, a tertiary amine, an inorganic carbonate or a hydrogen carbonate].

Method C

A compound of formula (I) [where $R^1$ is as defined above but is not hydrogen] may be prepared by reacting a compound of formula (I) [where $R^1$ is hydrogen] with a compound of formula $R^1$—$L^1$ [where $R^1$ is as defined above but is not hydrogen; and $L^1$ is a leaving group such as Cl, Br, I, a sulfonate (for example a mesylate or a tosylate) or OC(O)$C_{1-4}$ alkyl] in a solvent [such as a halogenated solvent (for example dichloromethane), an ether, ethylacetate, DMF or even water (as a biphasic mixture, optionally in the presence of a phase transfer catalyst such as tetrabutylammonium hydrogensulfate)] and in the presence of a base [such as a tertiary amine, an alkali carbonate, an alkali bicarbonate, an alkali hydroxide or NaH; though if $L^1$ is O(CO)$C_{1-4}$ alkyl then simply heating without base is possible].

Method D

A compound of formula (I) may be prepared by reacting a compound of formula (IV) [where Hal is preferably bromo or iodo] with a compound of formula $Het^1$-C(═O)$NH_2$ in the presence of a Cu(I) compound and an aprotic solvent [such as a cyclic ether, for example dioxane] at an elevated temperature and preferably at reflux. The preferred conditions are CuI used at 2% to 100% mole/mole, relative to the compound of formula (IV), in the presence of a 1,2-diamine as a ligand-forming substance (such as 1,2-diamino cyclohexane or ethylene diamine) and at least 1 equivalent of a base (such as an alkali carbonate or an alkali phosphate. The article by A. Klapars et al. J. Am. Chem. Soc. 123, 7727 (2001) provides details of analogous preparations.

Method E

A compound of formula (I) may be prepared by conversion of a compound of formula (V)

(V)

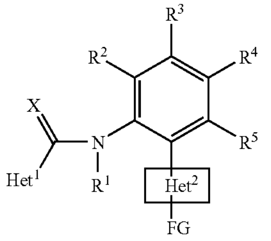

[where FG is a functional group which is convertible to $R^6$ in one or more synthetic steps]. Functional group interconversions are standard procedures for a person skilled in the art. There are many methods described in the literature, which can be used as such or with modifications according to the functionalities present; Table A gives literature references (some of which also cite further appropriate references) which are specifically relevant to the preparation of a compound of formula (I) by the interconversion of FG to $R^6$. It is apparent to the person skilled in the art that the literature examples given in Table A are not necessarily limited to the preparation of the specifically mentioned $R^6$ but can be also applied by analogy to the preparation of other structurally related $R^6$.

TABLE A

| Reference | FG | $R^6$ |
|---|---|---|
| Synthesis 2001, 2081 | CHO | CH═$CBr_2$ |
| Tetrahedron 58, 1491 (2002) | | CH═CHBr<br>C≡CBr |
| Russ. Chem. Bull. 50 (6), 1047 (2001) | CHO | CH═$CCl_2$ |
| Tetrahedron 57, 7519 (2001) | CHO | CH═$CClCF_3$<br>CH═$CFCF_2Cl$ |
| Bull. Chem. Soc. Jpn. 73, 1691 (2000) | CHO | CF═CBrF |
| Bull. Chem. Soc. Jpn. 71, 2903 (1998-) | | |

TABLE A-continued

| Reference | FG | $R^6$ |
|---|---|---|
| J. Chem. Soc. Perkin 1 2002, 883 | $COCH_3$ | $C(CH_3)=CHBr$ |
| | | $C(CH_3)=CCl_2$ |
| J. Fluorine Chem. 1, 381 (1972) | $COCH_3$ | $C(CH_3)=CBr_2$ |
| J. Fluorine Chem. 23, 339 (1983) | $COCF_3$ | $C(CH_3)=CFBr$ |
| | | $C(CH_3)=CFCl$ |
| | | $C(CF_3)=CFBr$ |
| | | $C(CF_3)=CFCl$ |
| | | $C(CF_3)=CF_2$ |
| Tetrahedron Letters 41, 8045 (2000) | Hal | $CF=CHF$ |
| J. Org. Chem. 62, 9217 (1997) | | |
| Tetrahedron Letters 37, 8799 (1996) | Hal | $CH=CF_2$ |
| JP 09278688 | Hal | $CF=CF_2$ |
| J. Fluorine Chem. 31, 115 (1986) | | |
| Zh. Org. Khim. 25, 1451 (1989) | Hal | $CF=CFCl$ |
| J. Org. Chem. 53, 2714 (1988) | Hal | $CF=CFCF_3$ |
| J. Org. Chem. 56, 7336 (1991) | Hal | $C(CF_3)=CH_2$ |
| Tetrahedron Letters 42, 4083 (2001) | | |
| Ukr. Khim. Zh. 32, 996 (1966) | $CHBrCH_2CF_3$ | $CH=CHCF_3$ |
| Bull. Chem. Soc. Jap. 62, 1352 | $CH=CClCF_3$ | $C\equiv CCF_3$ |
| | $CH=CFCF_2Cl$ | $C\equiv CCF_2Cl$ |
| J. Org. Chem. 54, 5856 (1989) | Hal or triflate | $C\equiv CH$ |
| J. Am. Chem. Soc. 109, 2138 (1987) | | $C\equiv CSiMe_3$ |
| Tetrahedron 45, 6511 (1989) | | $C\equiv CCH_3$ |
| J. Orgmet. Chem. 549, 127 (1997) | | $C\equiv CCMe_3$ |
| Tetrahedron 56, 10075 (2000) | | $C\equiv CCH_2OH$ |
| Tetrahedron Asymmetry 6, 245 (1995) | | $C\equiv CCHMeOH$ |
| | | $C\equiv CCMe_2OH$ |
| | | $C\equiv CCHO$ |
| | | $C\equiv CC(O)Me$ |
| J. Org. Chem. 32, 1674 (1967) | $C\equiv CCH_3$ | $CH_2C\equiv CH$ |
| Synth. Comm. 1989, 561 | CHO | $C\equiv CH$ |
| | $CH_2CHO$ | $CH_2C\equiv CH$ |
| WO 01 092563 | CHO | $CH=CH_2$ |
| J. Am. Chem. Soc. 123, 4155 (2001) | Hal or triflate | $CH=CH_2$ |
| Org. Lett. 2, 3703 (2000) | | |
| J. Org. Chem. 57, 3558 (1992) | | |
| Synthesis 2001, 893 | | |
| GB 2 183 639 | $C\equiv CH$ | $CH=CH_2$ |
| Synthesis 1996, 1494 | CHO | $C\equiv CCl$ |
| J. Org. Chem. 49, 294 (1984) | | $C\equiv CH$ |
| | | $C\equiv CBr$ |
| US 6 159956 | $CH_2Br$ | $CH_2CF=CF_2$ |
| Liebigs Ann. Chem. 1995, 2027 | $CH_2Br$ | $CH=C(CF_3)_2$ |
| J. Am. Chem. Soc. 123, 4155 (2001) | $CH_2Br$ | $CH_2C\equiv CSiMe_3$ |
| Inorg. Chim. Acta 296, 37 (1999) | Hal | $CH_2C\equiv CMe_3$ |
| J. Fluorine Chem.111, 185 (2001) | $CH=CHBr$ | $CH=CHCF_3$ |
| J. Chem. Soc. Perkin I 1988, 921 | $CH=CFBr$ | $CH=CFCF_3$ |
| | $CH=CBr_2$ | $CH=C(CF_3)_2$ |
| DE 4417441 | $C\equiv CCH_2OH$ | $C\equiv CCH_2F$ |
| U.S. Pat. No. 3976691 | $C\equiv CCHMeOH$ | $C\equiv CCHMeF$ |
| J. Org. Chem. 64, 7048 (1999) | $C\equiv CCMe_2OH$ | $C\equiv CCMe_2F$ |
| | $C\equiv CCHO$ | $C\equiv CCHF_2$ |
| | $C\equiv CC(O)Me$ | $C\equiv CCF_2Me$ |
| J. Chem. Soc. Perkin I 1994, 725 | $C\equiv CCH_2OH$ | $C\equiv CCH_2CF_3$ |
| Synthesis 1997, 1489 | $C\equiv CH$ | $C\equiv CCF_2CF_3$ |
| Angew. Chem. Int. Ed. 39, 2481 (2000) | | $CH=CHCF_2CF_3$ |
| J. Org. Chem. 47, 2255 (1982) | | |
| J. Fluorine. Chem. 113, 55 (2002) | | |
| J. Fluorine. Chem. 64, 61 (1993) | $C\equiv CH$ | $C\equiv CCHFCl$ |
| J. Am. Chem. Soc. 109, 3492 (1987) | | $C\equiv CCF_2Br$ |
| J. Am. Chem. Soc. 107, 5186 (1985) | $CH=CHBr$ | $CH=CHCF_2CF_3$ |

There are a number of alternative methods for preparing a compound of formula (II), (III) or (IV).

Method F—Preparation of a Compound of Formula (II), (III) or (IV).

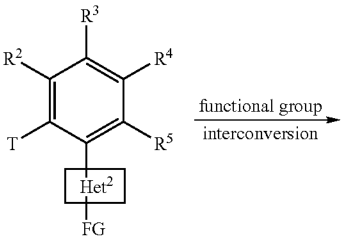

(VI)

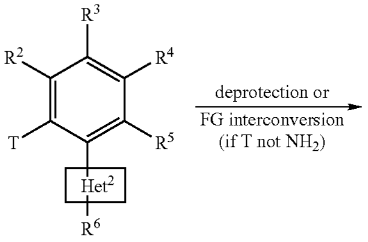

(II)

(II) (if T = $NHR^1$)
(III) (if T = $NO_2$)
(IV) (if T = Halogen)
(VII) (if T = T')

(T = $NH_2$)

A compound of formula (II), (III), (IV) or (VII) may be prepared, by functional group interconversion, from a compound of formula (VI) [where FG is as defined above for a compound of formula (V) and T is either halogen, nitro, amino, $NHR^1$ or a protected amino group T' (for example a carbamate, an amide, a cyclic imide, an N-alkyl-, N-alkenyl-, N-benzyl-, N-diphenylmethyl- or N-trityl-derivative, an imine derivative or an N-silyl- or N-disilyl-derivative). Starting from a compound of formula (VI) the functional group FG may be converted to $R^6$ by applying a method analogous to method E above. This conversion leads directly to a compound of formula (II) [when T is $NHR^1$], to a compound of formula (III) [when T is nitro], to a compound of formula (IV) [when T is halogen (preferably chloro, bromo or iodo)] or to a compound of formula (VII) [when T is T'].

In a second step a compound of formula (II) [when $R^1$ is other than H], (III) or (VII) can be converted to a compound of formula (II) [where $R^1$ is H] by applying the methods as generically described above.

Examples of versatile values for T' plus methods for deprotection are given in T. W. Green and P. Wuts, Protective Groups in Organic Synthesis, 3rd edition (John Wiley & Sons 1999), Chapter 7.

Compilations of useful values for T" plus literature to convert T" into $NH_2$, T' or $NHR^1$ can be found in M. B. Smith, Compendium of Organic Synthetic Methods, Vols. 1-10, Chapter 7 (Wiley, Vol. 10: 2002).

Method G

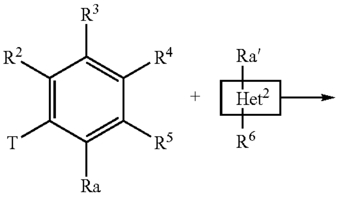

(VIII) (IX)

-continued

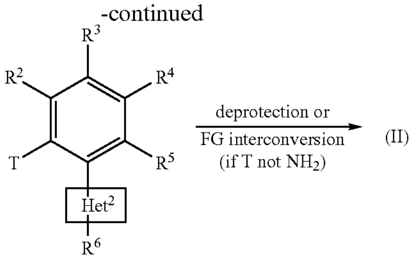

(II) (if T = NHR[1]) (T = NH2)
(III) (if T = NO2)
(IV) (if T = Halogen)
(VII) (if T = T')

A compound of formula (II), (III), (IV) or (VII) may be prepared by a coupling reaction between a compound of formula (VIII) and a compound of formula (IX) [where Ra and Ra' are each, independently, halogen (preferably Cl, Br or I), triflate or a metal-containing functionality containing, for example, B, Sn, Mg, Zn or Cu as the metal; examples are $B(OH)_2$, esters of boronic acid (preferably esters derived from 1,2- or 1,3-diols), trialkyltin (preferably $Sn(CH_3)_3$ or $Sn(nBu)_3$), a halogen salt of Mg, a halogen salt of Zn or Cu. If either Ra or Ra' is a metal containing functionality, the other substituent must be halogen or triflate.

Such coupling reactions are widely known in the literature. Especially suitable are the Pd(0), Ni(0), or copper catalysed couplings which are well known to the person skilled in the art as Stille coupling, Suzuki coupling, Negishi coupling or Ullmann reaction. Comprehensive reviews of these reactions can be found in Metal-Catalysed Cross-Coupling Reactions; F. Diederich and P. Stang (eds.); Wiley-VCH; Weinheim 1998 and in Handb. Organopalladium Chem. Org. Synth (2002).

In a second step a compound of formula (II) [when $R^1$ is other than H], (III) or (VII) can be converted to a compound of formula (II) [where $R^1$ is H] by either applying the methods as generically described above.

Surprisingly, it has now been found that the novel compounds of formula (I) have, for practical purposes, a very advantageous spectrum of activities for protecting plants against diseases that are caused by fungi as well as by bacteria and viruses.

The compounds of formula (I) can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

Therefore the invention relates also to a method of controlling or preventing infestation of useful plants by phytopathogenic microorganisms, wherein a compound of formula I is applied as active ingredient to the plants, to parts thereof or the locus thereof.

It is also possible to use compounds of formula (I) as dressing agents for the treatment of plant propagation material, in particular of seeds (fruit, tubers, grains) and plant cuttings (for example rice), for the protection against fungal infections as well as against phytopathogenic fungi occurring in the soil.

Furthermore the compounds according to present invention may be used for controlling fungi in related areas, for example in the protection of technical materials, including wood and wood related technical products, in food storage, in hygiene management, etc.

The compounds of formula (I) are, for example, effective against the phytopathogenic fungi of the following classes: Fungi imperfecti (e.g. *Botrytis, Pyricularia, Helminthosporium, Fusarium, Septoria, Cercospora* and *Alternaria*) and *Basidiomycetes* (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.) and rust (*Puccinia* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). An example for a truncated toxin is a truncated CryIA(b), which is expressed in the Bt11 maize from Syngenta Seed SAS, as described below. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810)

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (*Coleoptera*), two-winged insects (*Diptera*) and butterflies (*Lepidoptera*).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain *Coleoptera* insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain *Lepidoptera* insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain *Lepidoptera*, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula (I) are used in unmodified form or, preferably, together with the adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula (I), or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation [that is, a composition containing the compound of formula (I)] and, if desired, a solid or liquid adjuvant, is prepared in a known manner, typically by intimately mixing and/or grinding the compound with extenders, for example solvents, solid carriers and, optionally, surface active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha.

When used as seed drenching agent, convenient dosages are from 10 mg to 1 g of active substance per kg of seeds.

The rate of application for the desired action can be determined by experiments. It depends for example on the type of action, the developmental stage of the useful plant, and on the application (location, timing, application method) and can, owing to these parameters, vary within wide limits.

Whereas it is preferred to formulate commercial products as concentrates, the end user will normally use dilute formulations.

Surprisingly, it has now been found that the compounds of formula I, or a pharmaceutical salt thereof, described above have also an advantageous spectrum of activity for the treatment and/or prevention of microbial infection in an animal.

"Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula I in the manufacture of a medicament for use in the treatment and/or prevention of microbial infection in an animal. There is also provided the use of a compound of formula I as a pharmaceutical agent. There is also provided the use of a compound of formula I as an antimicrobial agent in the treatment of an animal. According to the present invention there is also provided a pharmaceutical composition comprising as an active ingredient a compound of formula I, or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula I are effective against various microbial species able to cause a microbial infection in an animal. Examples of such microbial species are those causing Aspergillosis such as *Aspergillus fumigatus, A. flavus, A. terrus, A. nidulans* and *A. niger*; those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in more detail.

EXAMPLE 1

This Example illustrates the preparation of 1-methyl-3-trifluoromethyl-1H-pyrazole-4-carboxylic acid {2-[5-(3,3-dimethyl-but-1-ynyl)-thiophen-2-yl]-phenyl}-amide (Compound No. 1ai.098).

a) Preparation of 2-(2-nitro-phenyl)-thiophene

Bis(triphenylphosphine)palladium(II) chloride (350 mg) and 2-(tributylstannyl)thiophene (57 g, 0.15 mol) were added to a solution of 1-iodo-2-nitrobenzene (35 g, 0.14 mol) in 500 ml of N,N-dimethylformamide. This mixture was heated for 16 h to 100° C. After concentration in vacuo, the residue was taken up in diethyl ether, washed with water and brine, dried over magnesium sulfate and evaporated. The remaining oil was purified by silica gel chromatography using ethyl acetate and hexane as eluents, yielding 23 g of 2-(2-nitro-phenyl)-thiophene.

b) Preparation of 2-iodo-5-(2-nitro-phenyl)-thiophene 2-(2-nitro-phenyl)-thiophene (23 g, 0.11 mol) and N-iodosuccinimide (37 g, 0.165 mol) were dissolved in 110 ml of methanol. To this solution, acetic acid (10 g, 0.165 mol) was added. After stirring the reaction mixture for 4 hours at room temperature, the solvent was evaporated. The remainder was taken up in a mixture of ice and water and extracted with ethyl acetate. The combined organic layer was washed with saturated aqueous sodium hydrogencarbonate solution and brine, dried over magnesium sulfate and evaporated, delivering 2-iodo-5-(2-nitro-phenyl)-thiophene (28 g).

c) Preparation of 2-(3,3-dimethyl-but-1-ynyl)-5-(2-nitro-phenyl)-thiophene (Compound No. 6i.030)

To a solution of 2-iodo-5-(2-nitro-phenyl)-thiophene (28 g, 84 mmol) in piperidine (235 ml) were added successively copper(I) iodide (0.8 g, 4.2 mmol), bis(triphenylphosphine) palladium(II) chloride (2.9 g, 4.2 mmol) and 3,3-dimethyl-1-butyne (14 g, 0.17 mol). This mixture was stirred for 16 hours at room temperature. Subsequently, it was poured into 1 litre of water, stirred for 15 minutes and extracted with tert-butyl methyl ether. The combined organic layer was washed with brine, dried over magnesium sulfate and evaporated. The remaining oil was purified by silica gel chromatography using ethyl acetate and hexane as eluents, giving Compound No. 6.030.i (22 g).

d) Preparation of 2-[5-(3,3-dimethyl-but-1-ynyl)-thiophen-2-yl]-phenylamine (Compound No. 5i.030)

A mixture of 2-(3,3-dimethyl-but-1-ynyl)-5-(2-nitro-phenyl)-thiophene (22 g, 76 mmol), tetrahydrofurane (100 ml) and acetic acid (425 ml of a 5% aqueous solution) was heated to 80° C. Iron powder (66 g, 1.2 mol) was added in small portions at this temperature. The reaction mixture was heated for 5 hours to reflux. After cooling, it was poured on ice and extracted with ethyl acetate. The combined organic layer was washed with brine, dried over magnesium sulfate and evaporated, delivering Compound No. 5.030.i (20 g).

e) 1-methyl-3-trifluoromethyl-1H-pyrazole-4-carboxylic acid (2.5 g, 13 mmol) was dissolved in dichloromethane (25 ml) containing 5 drops of N,N-dimethylformamide. A solution of oxalyl chloride (1.8 g, 14 mmol) in dichloromethane (5 ml) was added dropwise at room temperature. This mixture was stirred for 2 hours at the same temperature and was subsequently slowly added to a mixture of 2-[5-(3,3-dimethyl-but-1-ynyl)-thiophen-2-yl]-phenylamine (3.3 g, 13 mmol) and triethylamine (2.0 g, 20 mmol) in dichloromethane (30 ml). After stirring the reaction mixture for 8 hours at room temperature, it was poured on ice and extracted with dichloromethane. The combined organic layer was washed with brine, dried over magnesium sulfate and evaporated. The remaining oil was purified by silica gel chromatography using ethyl acetate and hexane as eluents, giving Compound No. 1ai.098 (1.2 g).

EXAMPLE 2

This Example illustrates the preparation of 3-difluoromethyl-1-methyl-1H-pyrazole-4-carboxylic acid {2-[4-(3,3-dimethyl-but-1-ynyl)-pyrazol-1-yl]-phenyl}-amide (Compound No. 1ar.099).

a) Preparation of 4-iodo-1-(2-nitro-phenyl)-1H-pyrazole

A mixture of 1-fluoro-2-nitrobenzene (14.5 g, 0.1 mol), 4-iodopyrazole (20 g, 0.1 mol), potassium carbonate anhydrous (14 g, 0.1 mol) and catalytical amounts of copper(II) oxide in pyridine (35 ml) was heated to reflux for 16 hours. After cooling, the mixture was diluted with dichloromethane (1 litre). Activated charcoal (12 g) was then added and the mixture was heated to reflux for 1 hour. After cooling, it was filtered through celite. The filtrate was evaporated and the remaining oil was purified by silica gel chromatography using ethyl acetate and hexane as eluents, giving 4-iodo-1-(2-nitro-phenyl)-1H-pyrazole (24 g).

b) Preparation of 4-(3,3-dimethyl-but-1-ynyl)-1-(2-nitro-phenyl)-1H-pyrazole (Compound No. 6r.030)

To a solution of 4-iodo-1-(2-nitro-phenyl)-1H-pyrazole (24 g, 76 mmol) in piperidine (215 ml) were added successively copper(I) iodide (0.7 g, 3.8 mmol), bis(triphenylphosphine)palladium(II) chloride (2.7 g, 3.8 mmol) and 3,3-dimethyl-1-butyne (12.5 g, 0.15 mol). This mixture was stirred for 16 hours at room temperature. Subsequently, it was poured into 1 litre of water, stirred for 15 minutes and extracted with tert-butyl methyl ether. The combined organic layer was washed with brine, dried over magnesium sulfate and evaporated. The remaining oil was purified by silica gel chromatography using ethyl acetate and hexane as eluents, giving Compound No. 6.030.r (20 g).

c) Preparation of 2-[4-(3,3-dimethyl-but-1-ynyl)-pyrazol-1-yl]-phenylamine (Compound No. 5r.030)

A mixture of 4-(3,3-dimethyl-but-1-ynyl)-1-(2-nitro-phenyl)-1H-pyrazole (20 g, 74 mmol), tetrahydrofurane (100 ml) and acetic acid (425 ml of a 5% aqueous solution) was heated to 80° C. Iron powder (66 g, 1.2 mol) was added in small portions at this temperature. The reaction mixture was heated for 5 hours to reflux. After cooling, it was poured onto ice and extracted with ethyl acetate. The combined organic layer was washed with brine, dried over magnesium sulfate and evaporated, delivering Compound No. 5.030.r (20 g).

d) 3-difluoromethyl-1-methyl-1H-pyrazole-4-carboxylic acid (2.4 g, 14 mmol) was dissolved in dichloromethane (25 ml) containing 5 drops of N,N-dimethylformamide. A solution of oxalyl chloride (1.9 g, 15 mmol) in dichloromethane (5 ml) was added dropwise at room temperature. This mixture was stirred for 2 hours at the same temperature and was subsequently slowly added to a mixture of Compound No. 5.030.r (3.3 g, 14 mmol) and triethylamine (2.0 g, 20 mmol) in dichloromethane (30 ml). After stirring the reaction mixture for 8 hours at room temperature, it was poured on ice and extracted with dichloromethane. The combined organic layer was washed with brine, dried over magnesium sulfate and evaporated. The remaining oil was purified by silica gel chromatography using ethyl acetate and hexane as eluents, giving Compound No. 1ar.099 (2.8 g).

FORMULATION EXAMPLES FOR COMPOUNDS OF FORMULA (I)

In the following formulation examples compounds of Tables 1aa to 1ax, of Tables 2ba to 2bx, of Tables 3ca to 3cx and of Tables 4da to 4dx are referred to as “active ingredient”.

Example F-1.1 to F-1.3

Emulsifiable Concentrates

| Components | F-1.1 | F-1.2 | F-1.3 |
|---|---|---|---|
| active ingredient | 25% | 40% | 50% |
| calcium dodecylbenzenesulfonate | 5% | 8% | 6% |
| castor oil polyethylene glycol ether (36 mol ethylenoxy units) | 5% | — | — |
| tributylphenolpolyethylene glycol ether (30 mol ethylenoxy units) | — | 12% | 4% |

-continued

| Components | F-1.1 | F-1.2 | F-1.3 |
|---|---|---|---|
| cyclohexanone | — | 15% | 20% |
| xylene mixture | 65% | 25% | 20% |

Emulsions of any desired concentration can be prepared by diluting such concentrates with water.

Example F-2

Emulsifiable Concentrate

| Components | F-2 |
|---|---|
| active ingredient | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| active ingredient | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| active ingredient | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| active ingredient | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| active ingredient | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| active ingredient | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

Fungicidal Actions

Example B-1

Action Against *Puccinia recondita*/Wheat (Brown Rust on Wheat)

1 week old wheat plants cv. Arina are treated with the formulated test compound (0.02% active ingredient) in a spray chamber. One day after application, the wheat plants are inoculated by spraying a spore suspension ($1\times10^5$ uredospores/ml) on the test plants. After an incubation period of 2 days at 20° C. and 95% r.h. the plants are kept in a greenhouse for 8 days at 20° C. and 60% r.h. The disease incidence is assessed 10 days after inoculation.

Infestation is prevented virtually completely (0-5% infestation) with each of compounds 1aa.098, 1aa.099, 1ab.098, 1ab.099, 1ai.078, 1ai.081, 1ai.098, 1ai.099, 1ar.099, 3ci.098, 4di.098 and 4dr.098.

Example B-2

Action Against *Podosphaera leucotricha*/Apple (Powdery Mildew on Apple)

5 week old apple seedlings cv. McIntosh are treated with the formulated test compound (0.02% active ingredient) in a spray chamber. One day after, the application apple plants are inoculated by shaking plants infected with apple powdery mildew above the test plants. After an incubation period of 12 days at 22° C. and 60% r.h. under a light regime of 14/10 hours (light/dark) the disease incidence is assessed.

Infestation is prevented virtually completely (0-5% infestation) with each of compounds 1ab.099, 1ai.77, 1ai.098, 1ai.099, 1ar.099, 2br.098, 3ci.098, 3cr.098, 4di.098 and 4dr.098.

Example B-3

Action Against *Venturia inaequalis*/Apple (Scab on Apple)

4 week old apple seedlings cv. McIntosh are treated with the formulated test compound (0.02% active ingredient) in a spray chamber. One day after application, the apple plants are inoculated by spraying a spore suspension ($4\times10^5$ conidia/ml) on the test plants. After an incubation period of 4 days at 21° C. and 95% r.h. the plants are placed for 4 days at 21° C. and 60% r.h. in a greenhouse. After another 4 day incubation period at 21° C. and 95% r.h. the disease incidence is assessed.

Infestation is prevented virtually completely (0-5% infestation) with each of compounds 1aa.099, 1ai.078, 1ai.099 and 3ci.098.

Example B-4

Action Against *Erysiphe graminis*/Barley (Powdery Mildew on Barley)

1 week old barley plants cv. Regina are treated with the formulated test compound (0.02% active ingredient) in a spray chamber. One day after application, the barley plants are inoculated by shaking powdery mildew infected plants above the test plants. After an incubation period of 6 days at 20° C./18° C. (day/night) and 60% r.h. in a greenhouse the disease incidence is assessed.

Infestation is prevented virtually completely (0-5% infestation) with each of compounds 1.aa.099, 1ab.099, 1ai.078, 1ai.098, 1ar.099, 2br.098 and 3cr.098.

Example B-5

Action Against *Botrytis cinerea*/Rape (*Botrytis* on Rapes)

5 week old grape seedlings cv. Gutedel are treated with the formulated test compound (0.02% active ingredient) in a spray chamber. Two days after application, the grape plants are inoculated by spraying a spore suspension ($1\times10^6$ conidia/ml) on the test plants. After an incubation period of 4 days at 21° C. and 95% r.h. in a greenhouse the disease incidence is assessed.

Infestation is prevented virtually completely (0-5% infestation) with each of compounds 1aa.098, 1aa.099, 1ab.098, 1ab.099, 1ai.078, 1ai.081, 1ai.099, 1ar.099, 3ci.098, 4di.098 and 4dr.098.

Example B-6

Action Against *Botrytis cinerea*/Tomato (*Botrytis* on Tomatoes)

4 week old tomato plants cv. Roter Gnom are treated with the formulated test compound (0.02% active ingredient) in a spray chamber. Two days after application, the tomato plants are inoculated by spraying a spore suspension ($1\times10^5$ conidia/ml) on the test plants. After an incubation period of 4 days at 20° C. and 95% r.h. in a growth chamber the disease incidence is assessed.

Infestation is prevented virtually completely (0-5% infestation) with each of compounds 1aa.098, 1aa.099, 1ab.098, 1ab.099, 1ai.078, 1ai.081, 1ai.099, 1ar.099, 3ci.098, 4di.098 and 4dr.098.

Example B-7

Action Against *Septoria nodorum*/Wheat (*Septoria* Leaf Spot on Wheat)

1 week old wheat plants cv. Arina are treated with the formulated test compound (0.02% active ingredient) in a spray chamber. One day after application, the wheat plants are inoculated by spraying a spore suspension ($5\times10^5$ conidia/ml) on the test plants. After an incubation period of 1 day at 20° C. and 95% r.h. the plants are kept for 10 days at 20° C. and 60% r.h. in a greenhouse. The disease incidence is assessed 11 days after inoculation.

Infestation is prevented virtually completely (0-5% infestation) with each of compounds 1ai.078, 1ai.098 and 1ar.099.

Example B-8

Action Against *Helminthosporium teres*/Barley (Net Blotch on Barley)

1 week old barley plants cv. Regina are treated with the formulated test compound (0.02% active ingredient) in a spray chamber. Two days after application, the barley plants are inoculated by spraying a spore suspension ($3\times10^4$ conidia/ml) on the test plants. After an incubation period of 4 days at 20° C. and 95% r.h. in a greenhouse the disease incidence is assessed.

Infestation is prevented virtually completely (0-5% infestation) with each of compounds 1aa.098, 1aa.099, 1ab.098, 1ab.099, 1ai.078, 1ai.081, 1ai.098, 1ai.099, 1ar.099, 2bi.098, 2br.098, 3ci.098, 3cr.098, 4di.098 and 4dr.098.

Example B-9

Action Against *Alternaria solani*/Tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension ($2\times10^5$ conidia/ml) on the test plants. After an incubation period of 3 days at 20° C. and 95% r.h. in a growth chamber the disease incidence is assessed.

Infestation is prevented virtually completely (0-5% infestation) with each of compounds 1aa.098, 1aa.099, 1ab.098, 1ab.099, 1ai.078, 1ai.081, 1ai.098, 1ai.099, 1ar.099, 2br.098, 3ci.098, 3cr.098, 4di.098 and 4dr.098.

Example B-10

Action Against *Uncinula necator*/Grape (Powdery Mildew on Grapes)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed.

Infestation is prevented virtually completely (0-5% infestation) with each of compounds 1aa.099, 1ai078, 1ai.098, 1ai.099, 1ar.099, 2br.098, 3ci.098, 3cr.098, 4di.098 and 4dr.098.

Example B-11

Action Against *Septoria tritici*/Wheat (*Septoria* Leaf Spot on Wheat)

2 week old wheat plants cv. Riband are treated with the formulated test compound (0.2% active ingredient) in a spray chamber. One day after application, wheat plants are inoculated by spraying a spore suspension ($10\times10^5$ conidia/ml) on the test plants. After an incubation period of 1 day at 23° C. and 95% r.h., the plants are kept for 16 days at 23° C. and 60% r.h. in a greenhouse. The disease incidence is assessed 18 days after inoculation. Compounds 1ai.078, 1ai.098, 1ai.099 and 1ar.099 each show good activity in this test (<20% disease incidence).

The invention claimed is:

1. A compound of formula (I):

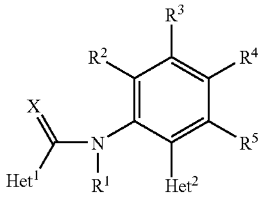

(I)

Wherein:

$Het^1$ is pyrazole, pyrrole, thiazole or pyridine being substituted by one, two or three groups $R^y$;

$Het^2$ is pyrazole, pyrrole, thiophene, furane, thiazole, isothiazole, oxazole, isoxazole, pyridine, pyrazine, pyrimidine, pyridazine, triazine, oxadiazole, thiadiazole or imidazole; $Het^2$ being substituted by $C{\equiv}CCMe_3$;

$R^1$ is hydrogen, formyl, CO—$C_{1-4}$alkyl, COO—$C_{1-4}$ alkyl, $C_{1-4}$ alkoxy($C_{1-4}$)alkylene, CO—$C_{1-4}$ alkylenoxy($C_{1-4}$) alkyl, propargyl or allenyl;

$R^2$, $R^3$, $R^4$ and $R^5$ are each, independently, hydrogen, halogen, methyl or $CF_3$;

each $R^y$ is, independently, halogen, $C_{1-3}$ alkyl, $C_{1-3}$ haloalkyl, $C_{1-3}$ alkoxy($C_{1-3}$)alkylene or cyano; and X is O or S.

2. A composition for controlling and protecting against phytopathogenic microorganisms, comprising a compound of formula I according to claim 1 and an inert carrier.

* * * * *